US012746230B2

(12) United States Patent
Bertels et al.

(10) Patent No.: US 12,746,230 B2
(45) Date of Patent: Sep. 29, 2026

(54) ANTICANCER COMPOSITIONS

(71) Applicant: Aragon Pharmaceuticals, Inc., Los Angeles, CA (US)

(72) Inventors: Johny Bertels, Mol (BE); Matthieu Garin, Wemmel (BE); Florentina Maria Preda, Dessel (BE); Reshema Kemps-Polanco, Titusville, NJ (US)

(73) Assignee: Aragon Pharmaceuticals, Inc., Horsham, PA (US)

( * ) Notice: Subject to any disclaimer, the term of this patent is extended or adjusted under 35 U.S.C. 154(b) by 0 days.

(21) Appl. No.: 19/217,221

(22) Filed: May 23, 2025

(65) Prior Publication Data

US 2025/0345319 A1 Nov. 13, 2025

Related U.S. Application Data

(63) Continuation of application No. PCT/US2024/016037, filed on Feb. 15, 2024.

(51) Int. Cl.

| | |
|---|---|
| ***A61K 31/4439*** | (2006.01) |
| ***A61K 9/20*** | (2006.01) |
| ***A61K 9/28*** | (2006.01) |
| ***A61P 35/00*** | (2006.01) |
| ***A61P 35/04*** | (2006.01) |

(52) U.S. Cl.

CPC ........ *A61K 31/4439* (2013.01); *A61K 9/2009* (2013.01); *A61K 9/2013* (2013.01); *A61K 9/2054* (2013.01); *A61K 9/2095* (2013.01); *A61K 9/2853* (2013.01); *A61P 35/00* (2018.01); *A61P 35/04* (2018.01)

(58) Field of Classification Search

CPC ............ A61K 49/0056; A61K 49/0032; A61K 38/08; A61K 47/6425; A61K 49/0021; A61K 47/64; A61P 29/00; A61P 35/00; A61P 9/10; G01N 33/57492; G01N 33/582; G01N 33/6893; C07K 7/06; C09K 11/06; C09K 2211/1029

See application file for complete search history.

(56) References Cited

U.S. PATENT DOCUMENTS

| | | | | |
|---|---|---|---|---|
| 2019/0216829 A1* | 7/2019 | Bertels | ................. | A61K 9/1652 |
| 2019/0322640 A1 | 10/2019 | Muthusamy et al. | | |
| 2022/0281836 A1 | 9/2022 | Sud et al. | | |
| 2023/0321246 A1* | 10/2023 | Yoon | .................... | A61K 31/365 514/449 |

FOREIGN PATENT DOCUMENTS

| | | | | |
|---|---|---|---|---|
| WO | 2013/184681 A1 | 12/2013 | | |
| WO | 2016/124149 A1 | 8/2016 | | |
| WO | 2019/016747 A1 | 1/2019 | | |
| WO | 2020/049598 A2 | 3/2020 | | |
| WO | 2020/188399 A1 | 9/2020 | | |
| WO | WO-2022060969 A1 * | 3/2022 | ............. | A61K 31/58 |

OTHER PUBLICATIONS

Erleada (apalutamide) 240 mg Approved as the Only Androgen Receptor Inhibitor with a Once-Daily Single-Tablet Option in Canada, Janssen Press Release, Aug. 21, 2023, 1-4.

* cited by examiner

*Primary Examiner* — Robert S Cabral
(74) *Attorney, Agent, or Firm* — BakerHostetler

(57) ABSTRACT

The present invention concerns pharmaceutical formulations of apalutamide, which can be administered to a mammal, in particular a human, suffering from an androgen receptor (AR)-related disease or condition, in particular cancer, more in particular prostate cancer.

24 Claims, 10 Drawing Sheets

Figure 1: Powder XRD. Diffraction patterns of apalutamide Form B.

Figure 2: Infrared spectrometry (microATR) of apalutamide Form B.

Figure 3: Differential scanning calorimetry (DSC) of apalutamide Form B.

Figure 7: Kaplan-Meier Plot of Updated Overall Survival (OS); Intent-to-treat mCSPC Population (TITAN)
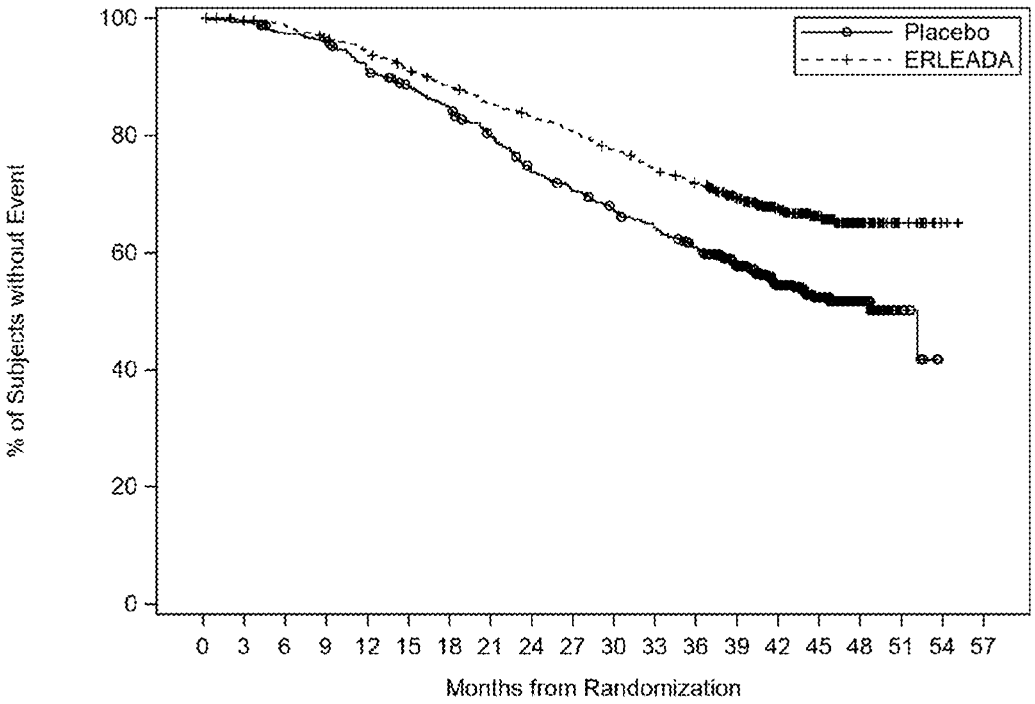
Subjects at risk
| | | | | | | | | | | | | | | | | | | | | |
|---|---|---|---|---|---|---|---|---|---|---|---|---|---|---|---|---|---|---|---|---|
| Placebo | 527 | 524 | 510 | 503 | 474 | 458 | 436 | 408 | 374 | 357 | 339 | 322 | 301 | 248 | 181 | 102 | 43 | 10 | 0 | 0 |
| ERLEADA | 525 | 519 | 513 | 500 | 489 | 469 | 452 | 438 | 425 | 412 | 394 | 376 | 362 | 321 | 227 | 139 | 52 | 15 | 3 | 0 |

Figure 8:Kaplan-Meier Plot of Radiographic Progression-Free Survival (rPFS); Intent-to-treat mCSPC Population (TITAN)
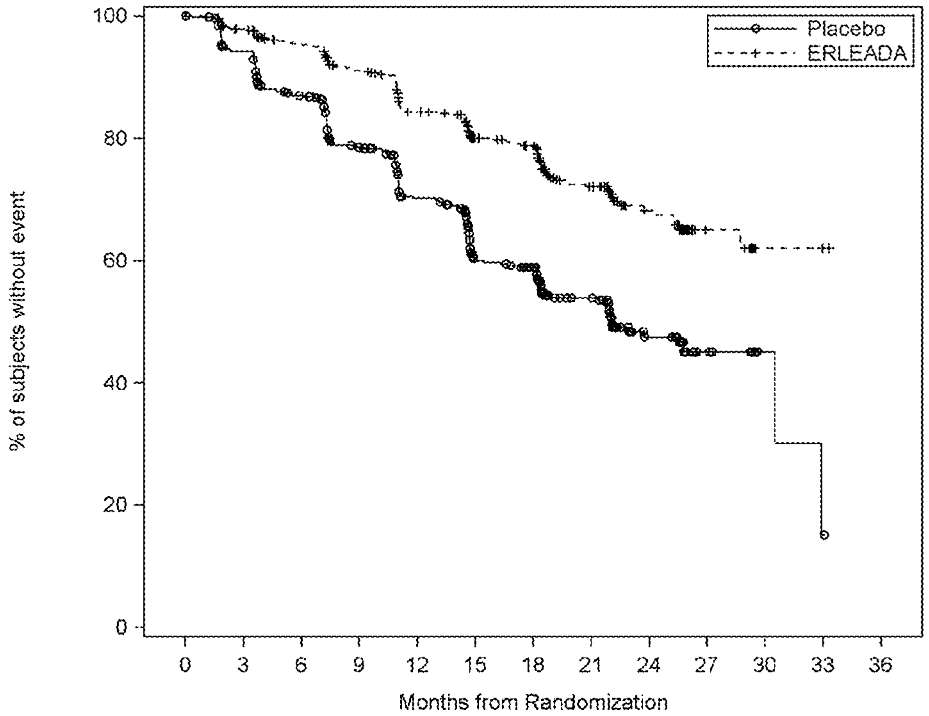
Subjects at risk
| | | | | | | | | | | | | | |
|---|---|---|---|---|---|---|---|---|---|---|---|---|---|
| Placebo | 527 | 488 | 437 | 381 | 325 | 240 | 229 | 140 | 57 | 14 | 3 | 1 | 0 |
| ERLEADA | 525 | 498 | 469 | 434 | 389 | 326 | 315 | 194 | 89 | 21 | 2 | 1 | 0 |

Figure 9: Kaplan-Meier Metastasis-Free Survival (MFS) Curve in SPARTAN (nmCRPC)
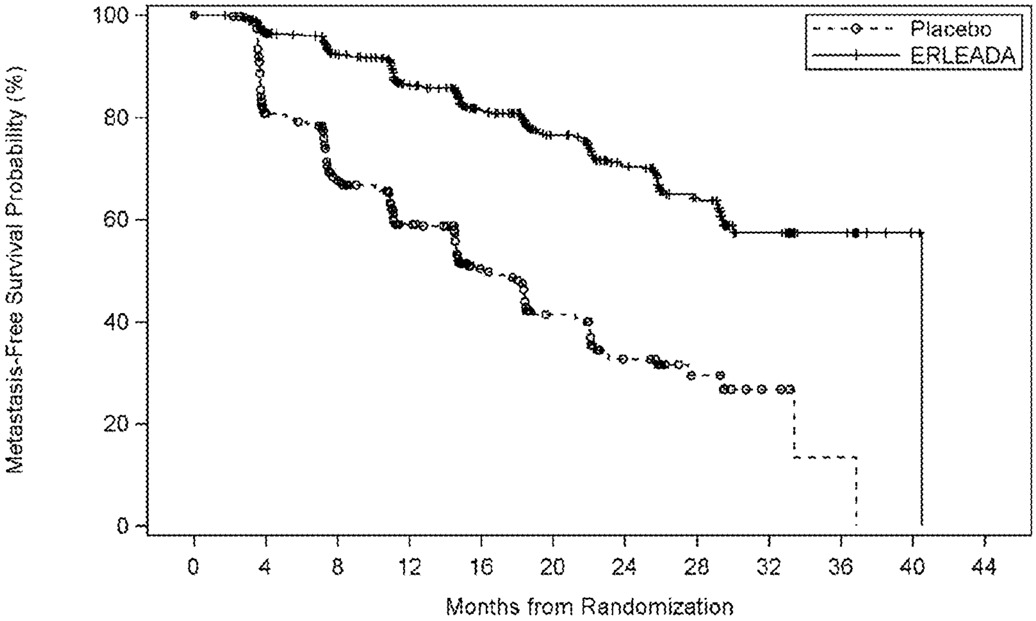
Subjects at risk
| | | | | | | | | | | | | |
|---|---|---|---|---|---|---|---|---|---|---|---|---|
| Placebo | 401 | 291 | 220 | 153 | 91 | 58 | 34 | 13 | 5 | 1 | 0 | 0 |
| ERLEADA | 806 | 713 | 652 | 514 | 398 | 282 | 180 | 96 | 36 | 16 | 3 | 0 |

Figure 10: Kaplan-Meier Overall Survival (OS) Curve in SPARTAN (nmCRPC)
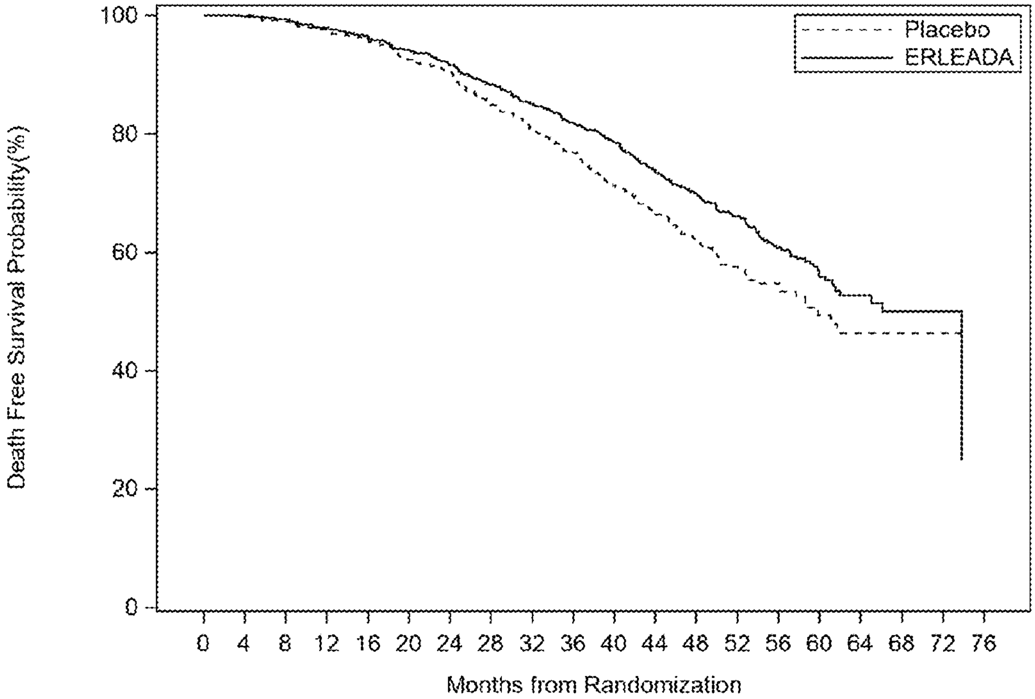
Subjects at risk
| | | | | | | | | | | | | | | | | | | | | |
|---|---|---|---|---|---|---|---|---|---|---|---|---|---|---|---|---|---|---|---|---|
| Placebo | 401 | 392 | 385 | 373 | 357 | 339 | 328 | 306 | 286 | 263 | 240 | 204 | 155 | 114 | 82 | 38 | 21 | 6 | 2 | 0 |
| ERLEADA | 806 | 791 | 774 | 758 | 739 | 717 | 691 | 658 | 625 | 593 | 558 | 499 | 374 | 269 | 181 | 100 | 47 | 19 | 4 | 0 |

ANTICANCER COMPOSITIONS

CROSS-REFERENCE TO RELATED APPLICATIONS

This application is a continuation of International Patent Application No. PCT/US24/16037, filed Feb. 15, 2024, the disclosure of which is incorporated by reference herein.

TECHNICAL FIELD

The present invention concerns pharmaceutical formulations of apalutamide, which can be administered to a mammal, in particular a human, suffering from an androgen receptor (AR)-related disease or condition, in particular cancer, more in particular prostate cancer, including but not limited to castration-resistant prostate cancer, metastatic castration resistant prostate cancer, chemotherapy-naive metastatic castration resistant prostate cancer, biochemically relapsed hormone sensitive prostate cancer, or high-risk, non-metastatic castration-resistant prostate cancer. In one aspect, these formulations comprise at least 60% w/w of a solid dispersion of apalutamide and a polymer selected from HPMCAS, a poly(meth)acrylate copolymer or a mixture of HPMCAS and a poly(meth)acrylate copolymer. In one aspect, these formulations comprise at least 60% w/w of a solid dispersion of apalutamide and a polymer selected from HPMCAS, a poly(meth)acrylate copolymer or a mixture of HPMCAS and a poly(meth)acrylate copolymer wherein the formulation comprises 240 mg of apalutamide. In one aspect, the solid dispersion of apalutamide and a polymer selected from HPMCAS, a poly(meth)acrylate copolymer or a mixture of HPMCAS and a poly(meth)acrylate copolymer is obtainable, in particular is obtained, by melt-extruding a mixture comprising apalutamide and a polymer selected from HPMCAS, a poly(meth)acrylate copolymer or a mixture of HPMCAS and a poly(meth)acrylate copolymer and optionally subsequently milling said melt-extruded mixture. In one aspect, the solid dispersion of apalutamide and a polymer selected from HPMCAS, a poly(meth)acrylate copolymer or a mixture of HPMCAS and a poly(meth) acrylate copolymer is obtainable, in particular is obtained, by spray drying a mixture comprising apalutamide and a polymer selected from HPMCAS, a poly(meth)acrylate copolymer or a mixture of HPMCAS and a poly(meth) acrylate copolymer in a suitable solvent.

The solid dispersion of apalutamide and a polymer selected from HPMCAS, a poly(meth)acrylate copolymer or a mixture of HPMCAS and a poly(meth)acrylate copolymer may be further formulated with a pharmaceutically acceptable carrier into a pharmaceutical formulation. With the formulation of the present invention the pill burden for the patient, in particular the cancer patient, can be reduced, and hence therapy adherence and therapy efficiency can be improved. With the formulation of the present invention the pill burden can be reduced while the dimension of the formulation, e.g. in the form of a tablet, is still acceptable, still allows acceptable swallowability for the patient, in particular the cancer patient.

BRIEF DESCRIPTION OF THE FIGURES

The summary, as well as the detailed description of preferred embodiments of the present application, will be better understood when read in conjunction with the appended figures. It should be understood, however, that the application is not limited to the precise embodiments shown in the figures.

FIG. 7 Kaplan-Meier Plot of Updated Overall Survival (OS); Intent-to-treat mCSPC Population (TITAN)

FIG. 8 Kaplan-Meier Plot of Radiographic Progression-Free Survival (rPFS); Intent-to-treat mCSPC Population (TITAN)

FIG. 9 Kaplan-Meier Metastasis-Free Survival (MFS) Curve in SPARTAN (nmCRPC)

FIG. 10 Kaplan-Meier Overall Survival (OS) Curve in SPARTAN (nmCRPC)

SUMMARY

Figure 1:
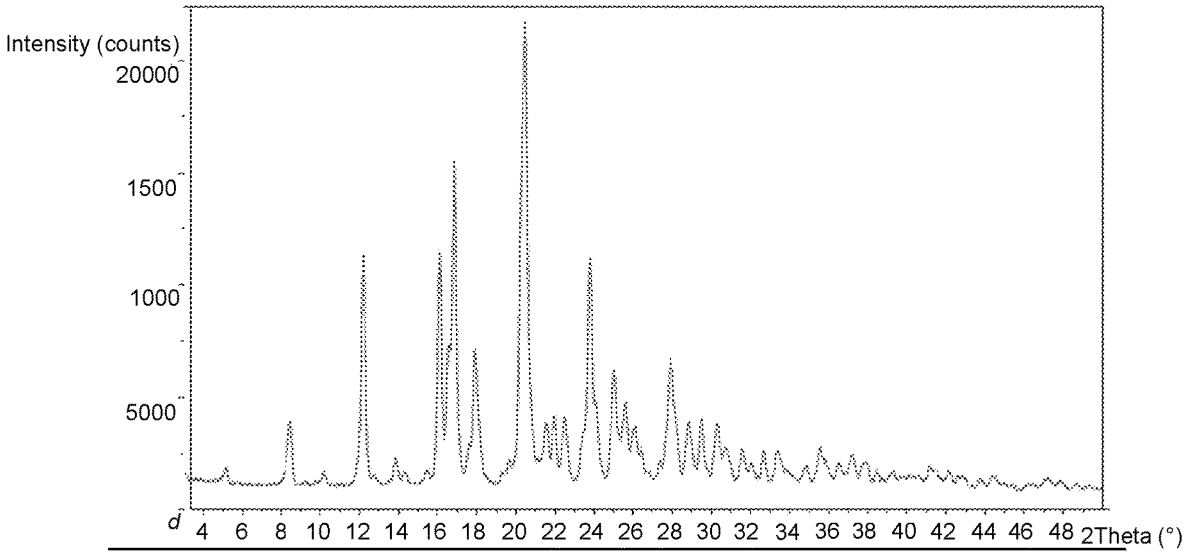
FIG. 1 XRD pattern of apalutamide Form B.

Apalutamide is a potent and specific antagonist of the androgen receptor (AR). Apalutamide's mechanism of action is antagonism of androgen receptor signaling through inhibition of AR nuclear translocation and DNA binding to androgen response elements.

The actions of androgens with androgen receptors have been implicated in a number of diseases or conditions, such as androgen dependent cancers, virilization in women, salivary gland cancer among others. Compounds that act on the adrogen axis find use in the treatment of diseases or conditions in which androgen receptors play a role.

Given the central role of AR in prostate cancer development and progression, apalutamide or the formulation or composition to the present invention is useful for the treatment of cancer, in particular prostate cancer, including but not limited to castration-resistant prostate cancer, metastatic castration resistant prostate cancer, non-metastatic castration resistant prostate cancer, chemotherapy-naive metastatic castration resistant prostate cancer, biochemically relapsed hormone sensitive prostate cancer, high-risk, non-metastatic castration-resistant prostate cancer, or metastatic castration-sensitive prostate cancer, in particular non-metastatic castration resistant prostate cancer or metastatic castration-sensitive prostate cancer.

The chemical structure of apalutamide is:

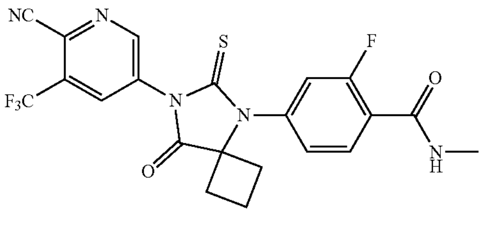 [SMILES: CNC(=O)c1ccc(N2C(=S)N(c3cnc(C#N)c(C(F)(F)F)c3)C(=O)C23CCC3)cc1F]

apalutamide or apalutamide or 4-[7-(6-cyano-5-trifluoromethylpyridin-3-yl)-8-oxo-6-thioxo-5,7-diazaspiro[3.4]oct-5-yl]-2-fluoro-N-methylbenzamide is commercially available as tablets containing 60 mg of apalutamide (Erleada®) and the recommended daily dose is 240 mg (four 60 mg tablets).

Given the daily number of tablets that a patient must take to maintain treatment, there is a need to reduce the number of tablets while maintaining the same dose and the same bioavailability. A reduced pill burden may contribute to improved therapy adherence and therapy efficiency.

An aspect as described herein relates to pharmaceutical formulations, in particular solid pharmaceutical formulations (e.g. tablets), more in particular solid pharmaceutical formulations for oral administration of apalutamide, where such formulations provide for a reduced pill burden for the patient, in particular the cancer patient. The pharmaceutical formulations of the present invention provide a means to increase therapy adherence of a patient, in particular a cancer patient. The pharmaceutical formulations of the present invention provide a means to increase therapy efficiency of a patient, in particular a cancer patient. With the formulation of the present invention the pill burden can be reduced while the dimension of the formulation, e.g. in the form of a tablet, is still acceptable, still allows acceptable swallowability for the patient, in particular the cancer patient.

An aspect as described herein relates to pharmaceutical formulations, in particular solid pharmaceutical formulations (e.g. tablets), more in particular solid pharmaceutical formulations for oral administration of apalutamide, where such formulations provide for a high drug load, i.e. at least more than 60 mg, or >60 mg to 240 mg or comprising 120 mg or comprising 240 mg of apalutamide, in particular provide for 240 mg of apalutamide per formulation, in particular per tablet.

An aspect as described herein relates to pharmaceutical formulations, in particular solid pharmaceutical formulations (e.g. tablets), more in particular solid pharmaceutical formulations for oral administration of apalutamide, where such formulations comprise at least 60% w/w of a solid dispersion of apalutamide and a polymer selected from HPMCAS, a poly(meth)acrylate copolymer or a mixture of HPMCAS and a poly(meth)acrylate copolymer, in particular at least 60% w/w of a solid dispersion of apalutamide and HPMCAS. In a further aspect, these formulations comprise at least 60% w/w of a solid dispersion of apalutamide and a polymer selected from HPMCAS, a poly(meth)acrylate copolymer or a mixture of HPMCAS and a poly(meth) acrylate copolymer, in particular at least 60% w/w of a solid dispersion of apalutamide and HPMCAS, and wherein the formulations comprise 240 mg of apalutamide per formulation.

An aspect as described herein relates to pharmaceutical formulations, in particular solid pharmaceutical formulations (e.g. tablets), more in particular solid pharmaceutical formulations for oral administration of apalutamide having a reduced amount of excipients, in particular comprising, consisting of and/or consisting essentially of at least 60% w/w of a solid dispersion of apalutamide and a polymer selected from HPMCAS, a poly(meth)acrylate copolymer or a mixture of HPMCAS and a poly(meth)acrylate copolymer, in particular at least 60% w/w of a solid dispersion of apalutamide and HPMCAS, and comprising, consisting of and/or consisting essentially of maximum 40% w/w of a pharmaceutically acceptable carrier. In a further aspect, these formulations comprise, consist of and/or consist essentially of at least 60% w/w of a solid dispersion of apalutamide and a polymer selected from HPMCAS, a poly(meth) acrylate copolymer or a mixture of HPMCAS and a poly (meth)acrylate copolymer, in particular at least 60% w/w of a solid dispersion of apalutamide and HPMCAS, and comprising, consisting of and/or consisting essentially of maximum 40% w/w of a pharmaceutically acceptable carrier and wherein the formulations comprise 240 mg of apalutamide per formulation.

An aspect as described herein relates to pharmaceutical formulations, in particular solid pharmaceutical formulations (e.g. tablets), more in particular solid pharmaceutical formulations for oral administration of apalutamide having a reduced amount of excipients, in particular comprising, consisting of and/or consisting essentially of at least 80% w/w of a solid dispersion of apalutamide and a polymer selected from HPMCAS, a poly(meth)acrylate copolymer or a mixture of HPMCAS and a poly(meth)acrylate copolymer, in particular at least 80% w/w of a solid dispersion of apalutamide and HPMCAS, and comprising, consisting of and/or consisting essentially of maximum 20% w/w of a pharmaceutically acceptable carrier. In a further aspect, these formulations comprise, consist of and/or consist essentially of at least 80% w/w of a solid dispersion of apalutamide and a polymer selected from HPMCAS, a poly(meth) acrylate copolymer or a mixture of HPMCAS and a poly (meth)acrylate copolymer, in particular at least 80% w/w of a solid dispersion of apalutamide and HPMCAS, and comprising, consisting of and/or consisting essentially of maximum 20% w/w of a pharmaceutically acceptable carrier and wherein the formulations comprise 240 mg of apalutamide per formulation.

An aspect as described herein relates to pharmaceutical formulations, in particular solid pharmaceutical formulations (e.g. tablets), more in particular solid pharmaceutical formulations for oral administration of apalutamide having a reduced amount of excipients, in particular comprising, consisting of and/or consisting essentially of about 82% w/w of a solid dispersion of apalutamide and a polymer selected from HPMCAS, a poly(meth)acrylate copolymer or a mixture of HPMCAS and a poly(meth)acrylate copolymer, in particular about 82% w/w of a solid dispersion of apalutamide and HPMCAS, and comprising, consisting of and/or consisting essentially of maximum about 18% w/w of a pharmaceutically acceptable carrier. In a further aspect, these formulations comprise, consist of and/or consist essentially of about 82% w/w of a solid dispersion of apalutamide and a polymer selected from HPMCAS, a poly(meth)acrylate copolymer or a mixture of HPMCAS and a poly(meth) acrylate copolymer, in particular about 82% w/w of a solid dispersion of apalutamide and HPMCAS, and comprising, consisting of and/or consisting essentially of maximum about 18% w/w of a pharmaceutically acceptable carrier and wherein the formulations comprise 240 mg of apalutamide per formulation.

An aspect as described herein relates to pharmaceutical formulations, in particular solid pharmaceutical formulations (e.g. tablets), more in particular solid pharmaceutical formulations for oral administration of apalutamide which are bioequivalent with four tablets of 60 mg of apalutamide per formulation, e.g. per tablet, in particular four tablets of Erleada® (apalutamide) 60 mg or 4 units of the commercially available 60 mg apalutamide tablet. In a further aspect, these formulations comprise and/or consist essentially of 240 mg of apalutamide per formulation, e.g. per tablet.

An aspect as described herein relates to pharmaceutical formulations, in particular solid pharmaceutical formulations (e.g. tablets), more in particular solid pharmaceutical formulations for oral administration of apalutamide having a $C_{max}$ that falls within the 80%-125% limit of the $C_{max}$ of four tablets of 60 mg of apalutamide per formulation, e.g. per tablet, in particular four tablets of Erleada® (apalutamide) 60 mg. In a further aspect, these formulations comprise and/or consist essentially of 240 mg of apalutamide per formulation, e.g. per tablet.

An aspect as described herein relates to pharmaceutical formulations, in particular solid pharmaceutical formulations (e.g. tablets), more in particular solid pharmaceutical formulations for oral administration of apalutamide having an AUC that falls within the 80%-125% limit of the AUC of four tablets of 60 mg of apalutamide per formulation, e.g. per tablet, in particular four tablets of Erleada® (apalutamide) 60 mg. In a further aspect, these formulations comprise and/or consist essentially of 240 mg of apalutamide per formulation, e.g. per tablet.

An aspect as described herein relates to pharmaceutical formulations, in particular solid pharmaceutical formulations (e.g. tablets), more in particular solid pharmaceutical formulations for oral administration of apalutamide having a $C_{max}$ and an AUC that falls within the 80%-125% limit of the $C_{m}$ax and of the AUC of four tablets of 60 mg of apalutamide per formulation, e.g. per tablet, in particular four tablets of Erleada® (apalutamide) 60 mg. In a further aspect, these formulations comprise and/or consist essentially of 240 mg of apalutamide per formulation, e.g. per tablet.

An aspect as described herein relates to pharmaceutical formulations, in particular solid pharmaceutical formulations (e.g. tablets), more in particular solid pharmaceutical formulations for oral administration of apalutamide with comparable bioavailability as four tablets of 60 mg of apalutamide per tablet, in particular four tablets of Erleada® (apalutamide) 60 mg. In a further aspect, these formulations comprise 240 mg of apalutamide per formulation.

A high drug load formulation (e.g. tablet), and further such a high drug load formulation wherein the drug is present in the formulation as a solid dispersion can be difficult to be achieved as the amount of excipients present in the formulation, e.g. tablet, is limited while still maintaining an acceptable size of the formulation, e.g. tablet. The present invention surprisingly and unexpectedly provides a high drug load formulation (e.g. tablet), i.e. a formulation comprising at least more than 60 mg, or comprising, consisting of and/or consisting essentially of >60 mg to 240 mg or comprising, consisting of and/or consisting essentially of 120 mg or comprising, consisting of and/or consisting essentially of 240 mg of apalutamide, in particular a 240 mg of apalutamide containing formulation e.g. tablet, and further such a high drug load formulation wherein apalutamide is present in the formulation as a solid dispersion, in particular a 240 mg of apalutamide containing formulation, e.g. tablet, wherein the formulation, e.g. tablet, comprises at least 60% w/w of a solid dispersion of apalutamide and a polymer selected from HPMCAS, a poly(meth)acrylate copolymer or a mixture of HPMCAS and a poly(meth) acrylate copolymer, in particular at least 60% w/w of a solid dispersion of apalutamide and HPMCAS. In an aspect, the present invention surprisingly and unexpectedly provides a high drug load formulation (e.g. tablet), i.e. a formulation comprising at least more than 60 mg, or comprising, consisting of and/or consisting essentially of >60 mg to 240 mg or comprising, consisting of and/or consisting essentially of 120 mg or comprising, consisting of and/or consisting essentially of 240 mg of apalutamide, and a pharmaceutically acceptable carrier, in particular a 240 mg of apalutamide containing formulation e.g. tablet, and further such a high drug load formulation wherein apalutamide is present in the formulation as a solid dispersion, in particular a 240 mg of apalutamide containing formulation, e.g. tablet, wherein the formulation, e.g. tablet, comprises, consist of and/or consists essentially of at least 60% w/w of a solid dispersion of apalutamide and a polymer selected from HPMCAS, a poly(meth)acrylate copolymer or a mixture of HPMCAS and a poly(meth)acrylate copolymer, in particular at least 60% w/w of a solid dispersion of apalutamide and HPMCAS, and a pharmaceutically acceptable carrier.

DETAILED DESCRIPTION

It is to be appreciated that certain features of the invention which are, for clarity, described herein in the context of separate embodiments may also be provided in combination in a single embodiment.

That is, unless obviously incompatible or specifically excluded, each individual embodiment is deemed to be combinable with any other embodiment(s) and such a combination is considered to be another embodiment. Conversely, various features of the invention that are, for brevity, described in the context of a single embodiment, may also be provided separately or in any sub-combination.

Finally, although an embodiment may be described as part of a series of steps or part of a more general structure, each said step may also be considered an independent embodiment in itself, combinable with others.

Certain Terminology

The transitional terms "comprising", "consisting essentially of", and "consisting" are intended to connote their generally accepted meanings in the patent vernacular; that is, (i) "comprising", which is synonymous with "including", "containing", or "characterized by", is inclusive or open-ended and does not exclude additional, unrecited elements or method steps; (ii) "consisting of" excludes any element, step, or ingredient not specified in the claim; and (iii) "consisting essentially of" limits the scope of a claim or embodiment to the specified materials or steps "and those that do not materially affect the basic and novel characteristic(s)" of the invention or the embodiment. More specifically, the basic and novel characteristics relates to the ability of the method or use to provide at least one of the benefits described herein, including but not limited to the ability to improve the survivability of the human population relative to the survivability of the comparative human population described elsewhere herein. Embodiments described in terms of the phrase "comprising" (or its equivalents), also provide, as embodiments, those which are independently described in terms of "consisting of" and "consisting essentially of".

When a value is expressed as an approximation by use of the descriptor "about", it will be understood that the particular value forms another embodiment. If not otherwise specified, the term "about" signifies a variance of ±10% of the associated value, but additional embodiments include those where the variance may be ±1%, ±2%, ±5%, ±15%, ±20%, ±25%, or ±50%, in particular the term "about" signifies a variance of ±5% or ±10% of the associated value, more in particular ±5%.

When a list is presented, unless stated otherwise, it is to be understood that each individual element of that list, and every combination of that list, is a separate embodiment. For example, a list of embodiments presented as "A, B, or C" is to be interpreted as including the embodiments, "A," "B," "C," "A or B," "A or C," "B or C," or "A, B, or C."

As used herein, the singular forms "a," "an," and "the" include the plural.

As used herein, "patient" is intended to mean any animal, in particular, mammals. Thus, the methods or uses are applicable to human and nonhuman animals, although most preferably with humans. The terms "patient" and "subject" and "human" may be used interchangeably.

The terms "treat," "treating," and "treatment" as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, delaying the progression of condition, relieving a condition caused by the disease or condition, or stopping the symptoms of the disease or condition either prophylactically and/or therapeutically, in particular therapeutically.

"Therapeutically effective amount" refers to an amount effective, at doses and for periods of time necessary, to achieve a desired therapeutic result. A therapeutically effective amount may vary depending on factors such as the disease state, age, sex, and weight of the individual, and the ability of a therapeutic or a combination of therapeutics to elicit a desired response in the individual. Exemplary indicators of an effective therapeutic or combination of therapeutics include, for example, improved well-being of the patient.

The terms "excipient" and carrier" are used interchangeably in the present disclosure. The European Pharmacopoeia (Ph. Eur.) defines an excipient as "any component, other than the active substance(s), present in a medicinal product or used in the manufacture of the product. The intended function of an excipient is to act as the carrier (vehicle or basis) or as a component of the carrier of the active substance(s) and, in so doing, to contribute to product attributes such as stability, biopharmaceutical profile, appearance and patient acceptability and to the ease with which the product can be manufactured. Usually, more than one excipient is used in the formulation of a medicinal product." The terms vehicle and basis are further defined in the same pharmacopoeia: "A vehicle is the carrier, composed of one or more excipients, for the active substance(s) in a liquid preparation" and "A basis is the carrier, composed of one or more excipients, for the active substance(s) in semi-solid and solid preparations."

The term "dosage" refers to the information of the amount of the therapeutic to be taken by the subject and the frequency of the number of times the therapeutic is to be taken by the subject.

The term "dose" refers to the amount or quantity of the therapeutic to be taken each time.

HPMCAS or hydroxypropyl methylcellulose acetate succinate or hypromellose acetate succinate (CAS number 71138-97-1) is a mixture of acetic acid and monosuccinic acid esters of hydroxypropylmethyl cellulose (IUPAC name: cellulose, 2-hydroxypropyl methyl ether, acetate, hydrogen butanedioate). Different grades are available differentiated based on degree/ratio of substitution (acetyl content, succinoyl content) and particle size (micronized and granular). In an aspect of the invention, the HPMCAS in the dispersions with apalutamide is HPMCAS LG (granular grade) or HPMCAS LF (micronized grade) (Shin-Etsu Chemical Co., Ltd), in particular HPMCAS LG.

Copolymers derived from esters of acrylic and methacrylic acid (poly(meth)acrylates) are known in the industry as Eudragit©. Eudragit© is the brand name for a diverse range of poly(meth)acrylate-based copolymers. Different grades are available. In an aspect of the invention, the Eudragit® in the dispersions with apalutamide is Eudragit® L 100-55 which contains an anionic copolymer based on methacrylic acid and ethyl acrylate (CAS number 25212-88-8; Chemical/IUPAC name: Poly(methacrylic acid-co-ethyl acrylate) 1:1) (Evonik Industries). In an aspect of the invention, the Eudragit® in the dispersions with apalutamide is Eudragit® E 100 which is a cationic copolymer based on dimethylaminoethyl methacrylate, butyl methacrylate, and methyl methacrylate (CAS number 24938-16-7; Chemical/IUPAC name: Poly(butyl methacrylate-co-(2-dimethylaminoethyl) methacrylate-co-methyl methacrylate) 1:2:1 (Evonik Industries).

An aspect as described herein relates to a pharmaceutical formulation, in particular a solid pharmaceutical formulations (e.g. a tablet), more in particular a solid pharmaceutical formulation, e.g. a tablet, for oral administration of apalutamide, where such formulation, e.g. tablet, comprises a solid dispersion comprising apalutamide and a polymer selected from HPMCAS, a poly(meth)acrylate copolymer or a mixture of HPMCAS and a poly(meth)acrylate copolymer, and a pharmaceutically acceptable carrier, wherein the solid dispersion is present at equal or greater than (≥) 60 w/w % relative to the total weight of the formulation, e.g. the tablet. In an aspect the solid dispersion is present at equal or greater than (≥) 65 w/w % or equal or greater than (≥) 70 w/w % or equal or greater than (≥) 75 w/w % or equal or greater than (≥) 80 w/w % or greater than (>) 80 w/w % relative to the total weight of the formulation, e.g. the tablet. In an aspect, the solid dispersion is present at equal or greater than (2) 82 w/w % relative to the total weight of the formulation, e.g. the tablet. In an aspect the solid dispersion is present at about 82.4 w/w % relative to the total weight of the formulation, e.g. the tablet.

In an aspect the formulation, e.g. tablet, as described herein, comprises a solid dispersion comprising apalutamide and HPMCAS, e.g. HPMCAS granular grade, e.g. HPMCAS LG.

In an aspect the formulation, e.g. tablet, as described herein, comprises a solid dispersion consisting of apalutamide and HPMCAS, e.g. HPMCAS granular grade, e.g. HPMCAS LG.

A preferred grade of HPMCAS in the solid dispersions as described herein is HPMCAS LG, because of its better and safer handling properties.

In an aspect, the weight-by-weight ratio of apalutamide: HPMCAS in the solid dispersion of the formulation, e.g. tablet, as described herein is in the range from 1:1 to 1:10, preferably from 1:1 to 1:5, more preferably from 1:1 to 1:3 or from 1:2 to 1:3. In an aspect, the weight-by-weight ratio of apalutamide:HPMCAS is 1:2. In an aspect, the weight-by-weight ratio of apalutamide:HPMCAS is 1:3. In an aspect, the weight-by-weight ratio of apalutamide: HPMCAS LG is 1:2. In an aspect, the weight-by-weight ratio of apalutamide:HPMCAS LG is 1:3.

In an aspect the formulation, e.g. tablet, as described herein, comprises particles comprising or consisting of, in particular consisting of, a solid dispersion as described herein. In an aspect, the formulation, e.g. tablet, as described herein, comprises particles comprising or consisting of, in particular consisting of, a solid dispersion comprising or consisting of, in particular consisting of, apalutamide and HPMCAS, e.g. HPMCAS granular grade, e.g. HPMCAS LG, wherein the weight-by-weight ratio of apalutamide to HPMCAS, e.g. HPMCAS granular grade, e.g. HPMCAS LG is in the range of 1:1 to 1:5, e.g. is 1:3.

In an aspect, the solid dispersion or the particles comprising or consisting of the solid dispersion as described herein are obtainable, in particular are obtained, by melt-extruding a mixture comprising apalutamide and HPMCAS and subsequently milling said melt-extruded mixture. In an aspect, the solid dispersion or the particles comprising or consisting of the solid dispersion as described herein are obtainable, in particular are obtained, by melt-extruding a mixture consisting of apalutamide and HPMCAS and subsequently milling said melt-extruded mixture. In an aspect, the weight-by-weight ratio of apalutamide:HPMCAS is 1:2 or 1:3, in particular 1:3.

In an aspect of the invention, the solid dispersion or the particles comprising or consisting of the solid dispersion as described herein are obtainable, in particular are obtained, by melt-extruding a mixture comprising apalutamide and HPMCAS LG and subsequently milling said melt-extruded mixture. In an aspect, the solid dispersion or the particles comprising or consisting of the solid dispersion as described herein are obtainable, in particular are obtained, by melt-extruding a mixture consisting of apalutamide and HPMCAS LG and subsequently milling said melt-extruded mixture. In an aspect, the weight-by-weight ratio of apalutamide:HPMCAS LG is 1:2 or 1:3, in particular 1:3.

In an aspect of the invention, the solid dispersion or the particles comprising or consisting of the solid dispersion as described herein are obtainable, in particular are obtained, by spray drying a mixture comprising apalutamide and HPMCAS in a suitable solvent. In an aspect, the solid dispersion or the particles comprising or consisting of the solid dispersion as described herein are obtainable, in particular are obtained, by spray drying a mixture consisting of apalutamide and HPMCAS in a suitable solvent. In an aspect, the weight-by-weight ratio of apalutamide: HPMCAS is 1:2 or 1:3, in particular 1:3.

In an aspect of the invention, the solid dispersion or the particles comprising or consisting of the solid dispersion as described herein are obtainable, in particular are obtained, by spray drying a mixture comprising apalutamide and HPMCAS LG in a suitable solvent. In an aspect, the solid dispersion or the particles comprising or consisting of the solid dispersion as described herein are obtainable, in particular are obtained, by spray drying a mixture consisting of apalutamide and HPMCAS LG in a suitable solvent. In an aspect, the weight-by-weight ratio of apalutamide: HPMCAS LG is 1:2 or 1:3, in particular 1:3.

An aspect as described herein relates to a pharmaceutical formulation, in particular a solid pharmaceutical formulations (e.g. a tablet), more in particular a solid pharmaceutical formulation, e.g. a tablet, for oral administration of apalutamide, where such formulation, e.g. tablet, comprises a pharmaceutically acceptable carrier and a solid dispersion or particles comprising or consisting of a solid dispersion, said solid dispersion comprising, in particular consisting of, apalutamide and HPMCAS, in particular HPMCAS granular grade, e.g. HPMCAS LG. In an aspect, the weight-by-weight ratio of apalutamide:HPMCAS is in the range of 1:1 to 1:5, e.g. is 1:2 or 1:3, in particular is 1:3. In an aspect, the solid dispersion or the particles are obtainable, in particular are obtained, by spray drying as described herein. The solid dispersion is present at equal or greater than (≥) 60 w/w % relative to the total weight of the formulation, e.g. the tablet, in particular is equal or greater than (≥) 80 w/w % or is greater than (>) 80 w/w % relative to the total weight of the formulation, e.g. the tablet, or is present at about 82.4 w/w % relative to the total weight of the formulation, e.g. the tablet.

In an aspect, there is provided a pharmaceutical formulation, e.g. a tablet, as described herein, wherein no surfactant is present.

In an aspect, there is provided a pharmaceutical formulation, e.g. a tablet, as described herein, wherein apalutamide is the only active pharmaceutical ingredient.

In the solid dispersions or particles or pharmaceutical formulations as described herein apalutamide is present in base form.

In an aspect, there is provided a pharmaceutical formulation, e.g. a tablet, as described herein, comprising about 240 mg of apalutamide, in particular comprising 240 mg of apalutamide. In an aspect, the formulation is administered once daily, in particular the formulation is administered orally once daily.

In an aspect, there is provided a pharmaceutical formulation, e.g. a tablet, as described herein, comprising about 960 mg of the solid dispersion as described herein, in particular comprising 960 mg of the solid dispersion. In an aspect, the formulation is administered once daily, in particular the formulation is administered orally once daily.

In an aspect, there is provided a pharmaceutical formulation, e.g. a tablet, as described herein, comprising about 240 mg of apalutamide and comprising about 960 mg of the solid dispersion, in particular comprising 240 mg of apalutamide and comprising 960 mg of the solid dispersion. In an aspect, the formulation is administered once daily, in particular the formulation is administered orally once daily.

An aspect as described herein relates to a pharmaceutical formulation, in particular a solid pharmaceutical formulation (e.g. a tablet), more in particular a solid pharmaceutical formulation, e.g. a tablet, for oral administration of apalutamide, in particular for oral once daily administration, where such formulation, e.g. tablet, comprises a pharmaceutically acceptable carrier and a solid dispersion or particles comprising or consisting of a solid dispersion, said solid dispersion comprising, in particular consisting of, apalutamide and HPMCAS, in particular HPMCAS granular grade, e.g.

HPMCAS LG, wherein the formulation comprises 240 mg of apalutamide. In an aspect, the weight-by-weight ratio of apalutamide:HPMCAS is in the range of 1:1 to 1:5, e.g. is 1:2 or 1:3, in particular is 1:3. In an aspect, the formulation comprises 960 mg of the solid dispersion. In an aspect, the solid dispersion or the particles are obtainable, in particular are obtained, by spray drying as described herein. The solid dispersion is present at equal or greater than (≥) 60 w/w % relative to the total weight of the formulation, e.g. the tablet, in particular is equal or greater than (≥) 80 w/w % or is greater than (>) 80 w/w % relative to the total weight of the formulation, e.g. the tablet, or is present at about 82.4 w/w % relative to the total weight of the formulation, e.g. the tablet.

The term "a solid dispersion" as used herein means a system in a solid state (as opposed to a liquid or gaseous state) having at least two components, wherein one component is distributed more or less evenly throughout the other component or components. When said dispersion of the components is such that the system is chemically and physically uniform or homogenous throughout or is one phase as defined in thermo-dynamics, such a solid dispersion will be called "a solid solution" herein. Solid solutions are preferred physical systems because the components therein are usually readily bioavailable to the organisms to which they are administered. This advantage can probably be explained by the ease with which said solid solutions can form liquid solutions when contacted with a liquid medium such as gastric juice. The ease of dissolution may be attributed at least in part to the fact that the energy required for dissolution of the components from a solid solution is less than that required for the dissolution of components from a crystalline or microcrystalline solid phase.

The term "a solid dispersion" also includes component systems that are less homogenous throughout than solid solutions. Such dispersions are not chemically and physically uniform throughout or, in other words, have more than one phase. For example, the term "a solid dispersion" also relates to a system in a solid state comprising at least two components (a) and (b) and having domains or small regions wherein amorphous, microcrystalline or crystalline (a), or amorphous, microcrystalline or crystalline (b), or both, are dispersed more or less evenly in another phase comprising (b), or (a), or a solid solution comprising (a) and (b). Said domains are regions distinctively marked by some physical feature, small in size compared to the size of the system as a whole, and evenly and randomly distributed throughout the system.

In preferred solid dispersions or particles apalutamide is present in an amourphous form as these have an intrinsically faster (e.g., shorter time) dissolution rate than those wherein part or all of apalutamide is in a microcrystalline or crystalline form.

Alternatively, the solid dispersions may be in the form of a dispersion wherein amorphous or microcrystalline apalutamide or amorphous or microcrystalline polymer selected from HPMCAS, a poly(meth)acrylate copolymer or a mixture of HPMCAS and a poly(meth)acrylate copolymer, in particular HPMCAS, is dispersed more or less evenly in a solid solution comprising apalutamide and a polymer selected from HPMCAS, a poly(meth)acrylate copolymer or a mixture of HPMCAS and a poly(meth)acrylate copolymer, in particular HPMCAS.

In an aspect, apalutamide is present in the pharmaceutical formulations as described herein in amorphous form. In an aspect, apalutamide is present in the solid dispersion of the pharmaceutical formulations as described herein in amorphous form.

In an aspect the solid dispersion in the pharmaceutical formulations as described herein is a solid solution.

Various techniques exist for preparing the solid dispersions of the pharmaceutical formulations as described herein including melt-extrusion (e.g. hot melt extrusion), spray-drying and solution-evaporation, in particular hot melt-extrusion and spray-drying, spray-drying being preferred. The particles comprising or consisting of or consisting essentially of the solid dispersion in the pharmaceutical formulations as described herein may be prepared by first preparing a solid dispersion of the components, and then optionally grinding or milling said dispersion.

The melt-extrusion process includes the following steps:

a) mixing apalutamide and a polymer selected from HPMCAS, a poly(meth)acrylate copolymer or a mixture of HPMCAS and a poly(meth)acrylate copolymer, in particular HPMCAS,
b) optionally blending additives with the thus obtained mixture,
c) heating the thus obtained blend until one obtains a homogenous melt,
d) forcing the thus obtained melt through one or more nozzles; and
e) cooling the melt till it solidifies.

The terms "melt" and "melting" do not only mean the alteration from a solid state to a liquid state, but can also refer to a transition to a glassy state or a rubbery state, and in which it is possible for one component of the mixture to get embedded more or less homogeneously into the other. In particular cases, one component will melt and the other component(s) will dissolve in the melt thus fonning a solution, which upon cooling may form a solid solution having advantageous dissolution properties.

One important parameter of melt extrusion is the temperature at which the melt-extruder is operating. For the melt extrusion process of the present invention, the operating temperature preferably ranges between about 160° C. and about 190° C., more preferably ranges between about 160° C. and 175° C. The lower temperature limit is defined by the point at which apalutamide is still melting during extrusion with a given set of extrusion conditions. When apalutamide is not completely molten, the extrudate may not provide the desired bioavailability. When the viscosity of the mixture is too high, the process of melt extrusion will be difficult. At higher temperatures the components may decompose to an unacceptable level. A person skilled in the art will recognize the most appropriate temperature range to be used.

The throughput rate is also of importance because the components may start to decompose when they remain too long in contact with the heating element.

It will be appreciated that the person skilled in the art will be able to optimize the parameters of the melt extrusion process within the above given ranges. The working temperatures will also be determined by the kind of extruder or the kind of configuration within the extruder that is used. Most of the energy needed to melt, mix and dissolve the components in the extruder can be provided by the heating elements. However, the friction of the material within the extruder may also provide a substantial amount of energy to the mixture and aid in the formation of a homogenous melt of the components.

A person skilled in the art will recognize the most appropriate extruder, such as, for example, a single screw, a twin screw extruder or a multi-screw extruder, for the preparation of the subject-matter of the present invention.

Spray-drying of a mixture of the components in a suitable solvent also yields a solid dispersion of said components or particles comprising or consisting of a solid dispersion of said components and may be a useful alternative to the melt-extrusion process, particularly in those cases where the polymer is not sufficiently stable to withstand the extrusion conditions and where residual solvent can effectively be removed from the solid dispersion.

Yet another possible preparation consists of preparing a mixture of the components in a suitable solvent, pouring said mixture onto a large surface so as to form a thin film, and evaporating the solvent therefrom.

Solvents suitable for spray-drying can be any organic solvent in which apalutamide and a polymer selected from HPMCAS, a poly(meth)acrylate copolymer or a mixture of HPMCAS and a poly(meth)acrylate copolymer, in particular HPMCAS, in particular HPMCAS LG, are miscable. In an aspect of the invention, the boiling point of the solvent is lower than the Tg (glass transition temperature) of the solid dispersion. In addition, the solvent should have relatively low toxicity and be removed from the dispersion to a level that is acceptable according to The International Committee on Harmonization (ICH) guidelines. Removal of solvent to this level may require a post drying step such as for instance tray-drying, subsequent to the spray-drying process. Solvents include alcohols such as methanol, ethanol, n-propanol, iso-propanol, and butanol, in particular methanol; ketones such as acetone, methyl ethyl ketone and methyl iso-butyl ketone; esters such as ethyl acetate and propylacetate; and various other solvents such as acetonitrile, dichloromethane, toluene, and 1,1,1-trichloroethane. Lower volatility solvents such as dimethyl acetamide or dimethylsulfoxide can also be used. In an aspect of the invention, the solvent suitable for spray drying is a mixture of solvents. In an aspect of the invention the solvent for spray drying is a mixture of an alcohol and dichloromethane, in particular a mixture of methanol and dichloromethane (methylene chloride), more in particular a mixture of methanol and dichloromethane 6:4 (w:w) or 5:5 (w/w), 6:4 (w:w) being preferred. In an aspect, the concentration of apalutamide and HPMCAS in the solvent mixture is 5% w/w.

In an aspect, the mixture to be spray-dried has the following composition:

Apalutamide: 250 mg
HPMCAS granular grade: 750 mg
Methanol* : 11400 mg
Methylene chloride* : 7600 mg
This material is a process aid and is removed during processing The particles as described herein have a $d^{50}$ of about 1500 μm, of about 1000 μm, of about 500 μm, of about 400 μm, of about 250 μm, of about 200 μm, of about 150 μm, of about 125 μm, of about 100 μm, of about 70 μm, of about 65 μm, of about 60 μm, of about 55 μm, of about 50 μm, of about 45 μm, of about 40 μm, of about 35 μm, of about 30 μm, of about 25 μm, or of about 20 μm. Particles obtained by spray drying have preferably a $d^{50}$-value falling in the range from about 20 μm to about 100 μm, in particular a $d^{50}$-value falling in the range from about 20 μm to about 70 μm, more in particular a $d^{50}$-value of about 20 μm, of about 25 μm, of about 30 μm, of about 35 μm, of about 40 μm, of about 45 μm, of about 50 μm, of about 55 μm, of about 60 μm, of about 65 μm, or of about 70 μm.

As used herein, the term $d^{50}$ has its conventional meaning as known to the person skilled in the art and can be measured by art-known particle size measuring techniques such as, for example, sedimentation field flow fractionation, photon correlation spectroscopy, laser diffraction or disk centrifugation. The $d^{50}$ mentioned herein may be related to volume distributions of the particles. In that instance, by "a $d^{50}$ of 50 μm" it is meant that at least 50% of the volume of the particles has a particle size of less than 50 μm. The same applies to the other particle sizes mentioned. In a similar manner, the $d^{50}$ particle size may be related to weight distributions of the particles. In that instance, by "$d^{50}$ of 50 μm" it is meant that at least 50% of the weight of the particles has a particle size of less than 50 μm. The same applies to the other particle sizes mentioned. Usually volume and weight distribution result in the same or about the same value for the average particle size.

The particle size can be an important factor determining the tabletting speed, in particular the flowability and therefore the manufacturability on a large scale of a particular dosage form or formulation, and the quality of the final product. For instance, for capsules, the particle size may range preferably from about 100 to about 1500 μm ($d^{50}$); for tablets the particle size is preferably less than 250 μm, more preferably less than 100 μm ($d^{50}$). Too small particles (<10-20 μm) often cause sticking on the tablet punches and manufacturability issues.

The particles or solid dispersions as described herein may further comprise one or more pharmaceutically acceptable excipients such as, for example, plasticizers, flavors, colorants, preservatives and the like. Especially in case of preparation by hot melt extrusion, said excipients should not be heat-sensitive, in other words, they should not show any appreciable degradation or decomposition at the working temperature of the melt-extruder.

Suitable plasticizers are pharmaceutically acceptable and include low molecular weight polyalcohols such as ethylene glycol, propylene glycol, 1,2 butylene glycol, 2,3-butylene glycol, styrene glycol; polyethylene glycols such as diethylene glycol, triethylene glycol, tetraethylene glycol; other polyethylene glycols having a molecular weight lower than 1,000 g/mol; polypropylene glycols having a molecular weight lower than 200 g/mol; glycol ethers such as monopropylene glycol monoisopropyl ether; propylene glycol monoethyl ether; diethylene glycol monoethyl ether; ester type plasticizers such as triethyl citrate, sorbitol lactate, ethyl lactate, butyl lactate, ethyl glycolate, allyl glycollate; and amines such as monoethanolamine, diethanolamine, triethanolamine, monoisopropanolamine; triethylenetetramine, 2-amino-2-methyl-1,3-propanediol and the like. Of these, the low molecular weight polyethylene glycols, ethylene glycol, low molecular weight polypropylene glycols and especially propylene glycol are preferred.

In an aspect, the particles or solid dispersions as described herein do not contain a plasticizer. In an aspect, the particles or solid dispersions as described herein do not contain further pharmaceutically acceptable excipients.

In an aspect, the pharmaceutical acceptable carrier of the pharmaceutical formulations as described herein may include one or more excipients such as disintegrants, diluents, fillers, binders, buffering agents, lubricants, glidants, thickening agents, sweetening agents, flavors, and colors. Some excipients can serve multiple purposes. In an aspect, the pharmaceutical formulations as described herein include a disintegrant, a diluent or filler, a lubricant and a glidant.

An aspect as described herein relates to a pharmaceutical formulation, in particular a solid pharmaceutical formulation (e.g. a tablet), more in particular a solid pharmaceutical formulation, e.g. a tablet, for oral administration of apalutamide, in particular for oral once daily administration, where such formulation, e.g. tablet, comprises a pharmaceutically acceptable carrier and a solid dispersion or particles comprising or consisting of a solid dispersion, said solid dispersion comprising, in particular consisting of, apalutamide and HPMCAS, in particular HPMCAS granular grade, e.g. HPMCAS LG, wherein the formulation comprises 240 mg of apalutamide and wherein the pharmaceutically acceptable carrier comprises, in particular consists of, a disintegrant, a diluent or filler, a lubricant and a glidant. In an aspect, the weight-by-weight ratio of apalutamide: HPMCAS is in the range of 1:1 to 1:5, e.g. is 1:2 or 1:3, in particular is 1:3. In an aspect, the formulation comprises 960 mg of the solid dispersion. In an aspect, the solid dispersion or the particles are obtainable, in particular are obtained, by spray drying as described herein. The solid dispersion is present at equal or greater than (≥) 60 w/w % relative to the total weight of the formulation, e.g. the tablet, in particular is equal or greater than (≥) 80 w/w % or is greater than (≥) 80 w/w % relative to the total weight of the formulation, e.g. the tablet, or is present at about 82.4 w/w % relative to the total weight of the formulation, e.g. the tablet. In an aspect the pharmaceutically acceptable carrier, in particular the disintegrant, diluent or filler, lubricant and glidant, is present at equal or less than (≥) 40 w/w % relative to the total weight of the formulation, e.g. the tablet, in particular is equal or less than (≤) 20 w/w % or is less than (≤) 20 w/w % relative to the total weight of the formulation, e.g. the tablet, or is present at about 17.6 w/w % relative to the total weight of the formulation, e.g. the tablet.

Suitable disintegrants are those that have a large coefficient of expansion. Examples thereof are hydrophilic, insoluble or poorly water-soluble crosslinked polymers such as crospovidone (crosslinked polyvinylpyrrolidone) and croscarmellose sodium (crosslinked sodium carboxymethylcellulose). The amount of disintegrant in the tablets according to the present invention may conveniently range from about 3 to about 12% (w/w) or range from about 3 to about 10% (w/w) and preferably range from about 3 to about 7%, in particular is about 6% (w/w). In an aspect, the disintegrant is croscarmellose sodium.

Examples of diluents or fillers are lactose monohydrate, anhydrous lactose, sucrose, dextrose, mannitol, sorbitol, starch, cellulose (e.g. micro-crystalline cellulose (Avicel™), silicified microcrystalline cellulose), dihydrated or anhydrous dibasic calcium phosphate, and others known in the art, and mixtures thereof (e.g. spray-dried mixture of lactose monohydrate (75%) with microcrystalline cellulose (25%) which is commercially available as Microcelac™). In an aspect, the filler or diluent is microcrystalline cellulose and silicified microcrystalline cellulose, in particular silicified microcrystalline cellulose. The amount of diluent or filler in the tablets may range from about 5% to about 20% (w/w) or may range from about 5% to about 15% (w/w). In an aspect, the amount of diluent or filler in the pharmaceutical formulation, e.g. the tablet, as described herein ranges from about 9.5 w/w % to about 10.5 w/w % relative to the total weight of the formulation, e.g. tablet. In an aspect, the amount of diluent or filler in the pharmaceutical formulation, e.g. the tablet, as described herein is about 10.3 w/w % relative to the total weight of the formulation, e.g. tablet. In an aspect, the amount of diluent or filler in the pharmaceutical formulation, e.g. the tablet, as described herein is about 9.9 w/w % relative to the total weight of the formulation, e.g. tablet.

Lubricants and glidants can be employed in the manufacture of certain dosage forms, and will usually be employed when producing tablets. Examples of lubricants and glidants are hydrogenated vegetable oils, e.g hydrogenated Cottonseed oil, magnesium stearate, stearic acid, sodium lauryl sulfate, magnesium lauryl sulfate, colloidal silica, colloidal anhydrous silica talc, mixtures thereof, and others known in the art. In an aspect the lubricant is magnesium stearate, or a mixtures of magnesium stearate with colloidal silica. In an aspect, the lubricant is magnesium stearate.

In an aspect, the glidant is colloidal anhydrous silica.

In an aspect, the amount of glidant, in particular colloidal anhydrous silica, in the pharmaceutical formulation, e.g. the tablet, as described herein ranges from about 0.2 w/w % to about 4.0 w/w % or ranges from about 0.2 w/w % to about 3.0 w/w % relative to the total weight of the formulation, e.g. tablet, in particular ranges from about 0.5 w/w % to about 1.5 w/w %, more in particular from about 0.5 w/w % to about 1 w/w %. relative to the total weight of the formulation, e.g. tablet. In an aspect, the amount of glidant, in particular colloidal anhydrous silica, in the pharmaceutical formulation, e.g. the tablet, as described herein is about 0.8 w/w % relative to the total weight of the formulation, e.g. tablet.

In an aspect, the amount of lubricant, in particular magnesium stearate, in the pharmaceutical formulation, e.g. the tablet, as described herein ranges from about 0.2 w/w % to about 4.0 w/w % or ranges from about 0.2 w/w % to about 3.0 w/w % relative to the total weight of the formulation, e.g. tablet, in particular ranges from about 0.2 w/w % to about 1.5 w/w %, or ranges from about 0.3 w/w % to about 1 w/w % or ranges from about 0.5 w/w % to about 1 w/w % relative to the total weight of the formulation, e.g. tablet. In an aspect, the amount of lubricant, in particular magnesium stearate, in the pharmaceutical formulation, e.g. the tablet, as described herein is about 0.5 w/w % relative to the total weight of the formulation, e.g. tablet.

An aspect as described herein relates to a pharmaceutical formulation, in particular a solid pharmaceutical formulation (e.g. a tablet), more in particular a solid pharmaceutical formulation, e.g. a tablet, for oral administration of apalutamide, in particular for oral once daily administration, where such formulation, e.g. tablet, comprises a pharmaceutically acceptable carrier and a solid dispersion or particles comprising or consisting of a solid dispersion, said solid dispersion comprising, in particular consisting of, apalutamide and HPMCAS, in particular HPMCAS granular grade, e.g. HPMCAS LG, wherein the formulation comprises 240 mg of apalutamide and wherein the pharmaceutically acceptable carrier comprises, in particular consists of, a disintegrant, in particular croscarmellose sodium, a diluent or filler, in particular silicified microcrystalline cellulose, a lubricant, in particular magnesium stearate, and a glidant, in particular colloidal anhydrous silica. In an aspect, the weight-by-weight ratio of apalutamide:HPMCAS is in the range of 1:1 to 1:5, e.g. is 1:2 or 1:3, in particular is 1:3. In an aspect, the formulation comprises 960 mg of the solid dispersion.

In an aspect, the solid dispersion or the particles are obtainable, in particular are obtained, by spray drying as described herein. The solid dispersion is present at equal or greater than (≥) 60 w/w % relative to the total weight of the formulation, e.g. the tablet, in particular is equal or greater than (≥) 80 w/w % or is greater than (≥) 80 w/w % relative to the total weight of the formulation, e.g. the tablet, or is present at about 82.4 w/w % relative to the total weight of the formulation, e.g. the tablet.

In an aspect the pharmaceutically acceptable carrier, in particular the disintegrant, in particular croscarmellose sodium, the diluent or filler, in particular silicified microcrystalline cellulose, the lubricant, in particular magnesium stearate, and the glidant, in particular colloidal anhydrous silica, is present at equal or less than (≤) 40 w/w % relative to the total weight of the formulation, e.g. the tablet, in particular is equal or less than (5) 20 w/w % relative to the total weight of the formulation, e.g. the tablet, or is present at about 17.6 w/w % relative to the total weight of the formulation, e.g. the tablet. In an aspect, the disintegrant, in particular croscarmellose sodium, is present at about 6 w/w % relative to the total weight of the pharmaceutical formulation, e.g. the tablet. In an aspect, the diluent or filler, in particular silicified microcrystalline cellulose, is present at about 10 w/w %, e.g. 10.3 w/w %, relative to the total weight of the pharmaceutical formulation, e.g. the tablet. In an aspect, the lubricant, in particular magnesium stearate, is present at about 0.5 w/w % relative to the total weight of the pharmaceutical formulation, e.g. the tablet. In an aspect, the glidant, in particular colloidal anhydrous silica, is present at about 0.8 w/w % relative to the total weight of the pharmaceutical formulation, e.g. the tablet.

Other excipients such as coloring agents and pigments may also be added to the formulations of the invention. Coloring agents and pigments include titanium dioxide and dyes suitable for food. A coloring agent is an optional ingredient in the formulation of the invention, but when used the coloring agent can be present in an amount up to 4% based on the total tablet weight.

Flavors are optional in the formulation and may be chosen from synthetic flavor oils and flavoring aromatics or natural oils, extracts from plants leaves, flowers, fruits and so forth and combinations thereof. These may include cinnamon oil, oil of wintergreen, peppermint oils, bay oil, anise oil, *eucalyptus*, thyme oil. Also useful as flavors are vanilla, citrus oil, including lemon, orange, grape, lime and grapefruit, and fruit essences, including apple, banana, pear, peach, strawberry, raspberry, cherry, plum, pineapple, apricot and so forth. The amount of flavor may depend on a number of factors including the organoleptic effect desired. Generally the flavor will be present in an amount from about 0% to about 3% (w/w).

In an aspect, the pharmaceutical formulation, e.g. tablet, as described herein does not contain a coloring agent, a pigment or a flavor. In an aspect, the pharmaceutical formulation, e.g. tablet, as described herein does not contain a coloring agent, a pigment and a flavor.

Formulation blends, e.g. tablet blends, or parts of formulation blends, e.g. parts of tablet blends, may be granulated, e.g. dry-granulated or wet-granulated before tabletting. In an aspect, the pharmaceutical formulation, e.g. the tablet, as described herein comprises an intragranular phase and an extragranular phase.

In an aspect, the intragranular phase of the pharmaceutical formulation, e.g. tablet, as described herein comprises a solid dispersion comprising apalutamide and a polymer selected from HPMCAS, a poly(meth)acrylate copolymer or a mixture of HPMCAS and a poly(meth)acrylate copolymer, in particular HPMCAS, as described herein, and a glidant, in particular colloidal anhydrous silica. In an aspect, the intragranular phase of the pharmaceutical formulation, e.g. tablet, as described herein comprises a solid dispersion comprising apalutamide and a polymer selected from HPMCAS, a poly(meth)acrylate copolymer or a mixture of HPMCAS and a poly(meth)acrylate copolymer, in particular HPMCAS, as described herein, and a glidant, in particular colloidal anhydrous silica, wherein the amount of the glidant, in particular colloidal anhydrous silica, ranges from about 0.1 w/w % to about 1.5 w/w % or ranges from about 0.2 w/w % to about 1 w/w % or ranges from about 0.3 w/w % to about 0.5 w/w % or is about 0.5 w/w % or about 0.47 w/w % relative to the total weight of the intragranular phase.

In an aspect, the intragranular phase of the pharmaceutical formulation, e.g. tablet, as described herein comprises a solid dispersion comprising apalutamide and a polymer selected from HPMCAS, a poly(meth)acrylate copolymer or a mixture of HPMCAS and a poly(meth)acrylate copolymer, in particular HPMCAS, as described herein, and a disintegrant, in particular croscarmellose sodium. In an aspect, the intragranular phase of the pharmaceutical formulation, e.g. tablet, as described herein comprises a solid dispersion comprising apalutamide and a polymer selected from HPMCAS, a poly(meth)acrylate copolymer or a mixture of HPMCAS and a poly(meth)acrylate copolymer, in particular HPMCAS, as described herein, and a disintegrant, in particular croscarmellose sodium, wherein the amount of the disintegrant, in particular croscarmellose sodium, ranges from about 1 w/w % to about 5 w/w % or ranges from about 2 w/w % to about 4 w/w % or ranges from about 3 w/w % to about 4 w/w % or is about 3.5 w/w % relative to the total weight of the intragranular phase.

In an aspect, the intragranular phase of the pharmaceutical formulation, e.g. tablet, as described herein comprises, consists of or consists essentially of a solid dispersion comprising apalutamide and a polymer selected from HPMCAS, a poly(meth)acrylate copolymer or a mixture of HPMCAS and a poly(meth)acrylate copolymer, in particular HPMCAS, as described herein, a glidant, in particular colloidal anhydrous silica, and a disintegrant, in particular croscarmellose sodium. In an aspect, the intragranular phase of the pharmaceutical formulation, e.g. tablet, as described herein comprises, consists of or consists essentially of a solid dispersion comprising apalutamide and a polymer selected from HPMCAS, a poly(meth)acrylate copolymer or a mixture of HPMCAS and a poly(meth)acrylate copolymer, in particular HPMCAS, as described herein, a glidant, in particular colloidal anhydrous silica, and a disintegrant, in particular croscarmellose sodium, wherein the amount of the glidant, in particular colloidal anhydrous silica, ranges from about 0.1 w/w % to about 1.5 w/w % or ranges from about 0.2 w/w % to about 1 w/w % or ranges from about 0.3 w/w % to about 0.5 w/w % or is about 0.5 w/w % or about 0.47 w/w % relative to the total weight of the intragranular phase, and wherein the amount of the disintegrant, in particular croscarmellose sodium, ranges from about 1 w/w % to about 5 w/w % or ranges from about 2 w/w % to about 4 w/w % or ranges from about 3 w/w % to about 4 w/w % or is about 3.5 w/w % relative to the total weight of the intragranular phase.

In an aspect, the intragranular phase of the pharmaceutical formulation, e.g. tablet, as described herein comprises a solid dispersion comprising apalutamide and a polymer selected from HPMCAS, a poly(meth)acrylate copolymer or a mixture of HPMCAS and a poly(meth)acrylate copolymer, in particular HPMCAS, as described herein, a glidant, in particular colloidal anhydrous silica, and a disintegrant, in particular croscarmellose sodium. In an aspect, the intragranular phase of the pharmaceutical formulation, e.g. tablet, as described herein does not comprises a (dry) binder. In an aspect, the intragranular phase of the pharmaceutical formulation, e.g. tablet, as described herein consists of a solid dispersion comprising apalutamide and a polymer selected from HPMCAS, a poly(meth)acrylate copolymer or a mixture of HPMCAS and a poly(meth)acrylate copolymer, in particular HPMCAS, as described herein, a glidant, in particular colloidal anhydrous silica, and a disintegrant, in particular croscarmellose sodium. In an aspect, the intragranular phase of the pharmaceutical formulation, e.g. tablet, as described herein comprises a solid dispersion comprising apalutamide and a polymer selected from HPMCAS, a poly(meth)acrylate copolymer or a mixture of HPMCAS and a poly(meth)acrylate copolymer, in particular HPMCAS, as described herein, a glidant, in particular colloidal anhydrous silica, and a disintegrant, in particular croscarmellose sodium, wherein the amount of the glidant in the intragranular phase ranges from about 0.0085 w/w % to about 1.3 w/w % or ranges from about 0.17 w/w % to about 0.85 w/w % or ranges from about 0.26 w/w % to about 0.43% or is about 0.4 w/w % relative to the total weight of the pharmaceutical formulation, e.g. the tablet, and wherein the amount of the disintegrant in the intragranular phase ranges from about 0.85 w/w % to about 4.29 w/w % or ranges from about 1.72 w/w % to about 3.43 w/w % or ranges from about 2.58 w/w % to about 3.43 w/w % or is about 3 w/w % relative to the total weight of the pharmaceutical formulation, e.g. the tablet. In an aspect, the intragranular phase of the pharmaceutical formulation, e.g. tablet, as described herein does not comprises a (dry) binder. In an aspect, the intragranular phase of the pharmaceutical formulation, e.g. tablet, as described herein consists of a solid dispersion comprising apalutamide and a polymer selected from HPMCAS, a poly(meth)acrylate copolymer or a mixture of HPMCAS and a poly(meth)acrylate copolymer, in particular HPMCAS, as described herein, a glidant, in particular colloidal anhydrous silica, and a disintegrant, in particular croscarmellose sodium, wherein the amount of the glidant in the intragranular phase is about 0.4 w/w % relative to the total weight of the pharmaceutical formulation, e.g. the tablet, and wherein the amount of the disintegrant in the intragranular phase is about 3 w/w % relative to the total weight of the pharmaceutical formulation, e.g. the tablet.

In an aspect, the intragranular phase is granulated by roller compaction. Roller compaction may exhibit enhanced formulation robustness.

In an aspect, the extragranular phase of the pharmaceutical formulation, e.g. tablet, as described herein comprises a filler, in particular silicified microcrystalline cellulose, a glidant, in particular colloidal anhydrous silica, a disintegrant, in particular croscarmellose sodium, and a lubricant, in particular magnesium stearate. In an aspect, the extragranular phase of the pharmaceutical formulation, e.g. tablet, as described herein consists of a filler, in particular silicified microcrystalline cellulose, a glidant, in particular colloidal anhydrous silica, a disintegrant, in particular croscarmellose sodium, and a lubricant, in particular magnesium stearate. In an aspect, the extragranular phase of the pharmaceutical formulation, e.g. tablet, as described herein comprises a filler, in particular silicified microcrystalline cellulose, a glidant, in particular colloidal anhydrous silica, a disintegrant, in particular croscarmellose sodium, and a lubricant, in particular magnesium stearate, wherein the amount of the filler is about 10.3 w/w % relative to the total weight of the pharmaceutical formulation, e.g. the tablet, wherein the amount of the glidant is about 0.4 w/w % relative to the total weight of the pharmaceutical formulation, e.g. the tablet, wherein the amount of the disintegrant is about 3 w/w % relative to the total weight of the pharmaceutical formulation, e.g. the tablet, and wherein the lubricant is about 0.5 w/w % relative to the total weight of the pharmaceutical formulation, e.g. the tablet. In an aspect, the extragranular phase of the pharmaceutical formulation, e.g. tablet, as described herein consists of a filler, in particular silicified microcrystalline cellulose, a glidant, in particular colloidal anhydrous silica, a disintegrant, in particular croscarmellose sodium, and a lubricant, in particular magnesium stearate, wherein the amount of the filler is about 10.3 w/w % relative to the total weight of the pharmaceutical formulation, e.g. the tablet, wherein the amount of the glidant is about 0.4 w/w % relative to the total weight of the pharmaceutical formulation, e.g. the tablet, wherein the amount of the disintegrant is about 3 w/w % relative to the total weight of the pharmaceutical formulation, e.g. the tablet, and wherein the lubricant is about 0.5 w/w % relative to the total weight of the pharmaceutical formulation, e.g. the tablet.

In an aspect there is provided a pharmaceutical formulation, e.g. a tablet, comprising an intragranular phase and an extragranular phase, wherein the intragranular phase comprises:

a solid dispersion comprising

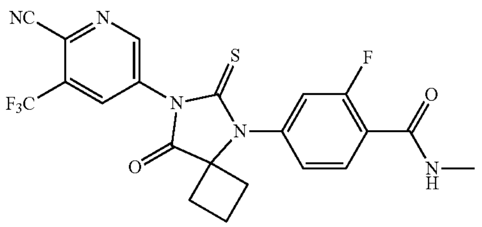 [SMILES: CNC(=O)c1ccc(N2C(=S)N(c3cnc(C#N)c(C(F)(F)F)c3)C(=O)C23CCC3)cc1F]

(apalutamide) and hydroxypropyl methylcellulose acetate succinate (HPMCAS), colloidal anhydrous silica, and croscarmellose sodium, and wherein the extragranular phase comprises:

silicified microcrystalline cellulose colloidal anhydrous silica, croscarmellose sodium, and magnesium stearate, and wherein the solid dispersion is present at equal or greater than 80 w/w % or is greater than (>) 80 w/w % relative to the total weight of the pharmaceutical formulation, e.g. the tablet.

In an aspect there is provided a pharmaceutical formulation, e.g. a tablet, wherein the pharmaceutical formulation, e.g. the tablet, has the following composition:

| Component | w/w (%) |
|---|---|
| Intragranular phase | |
| Spray Dried Powder comprising apalutamide and HPMCAS at a 1:3 ratio by weight | 82.40 |
| Colloidal Anhydrous Silica | 0.40 |
| Croscarmellose Sodium | 3.00 |
| Extragranular phase | |
| Silicified Microcrystalline Cellulose | 10.28 |
| Colloidal Anhydrous Silica | 0.40 |
| Croscarmellose Sodium | 3.00 |
| Magnesium Stearate | 0.50 |

wherein the tablet optionally further comprises a coating.

In an aspect there is provided a pharmaceutical formulation, e.g. a tablet, wherein the pharmaceutical formulation, e.g. the tablet, has the following composition:

| Component | w/w (%) |
|---|---|
| Intragranular phase | |
| Spray Dried Powder consisting of apalutamide and HPMCAS at a 1:3 ratio by weight | 82.40 |
| Colloidal Anhydrous Silica | 0.40 |
| Croscarmellose Sodium | 3.00 |
| Extragranular phase | |
| Silicified Microcrystalline Cellulose | 10.28 |
| Colloidal Anhydrous Silica | 0.40 |
| Croscarmellose Sodium | 3.00 |
| Magnesium Stearate | 0.50 |

wherein the tablet optionally further comprises a coating.

The tabletting process itself is otherwise standard and readily practised by forming a tablet from desired blend or mixture of ingredients into the appropriate shape using a conventional tablet press. Tablets as described herein may further be film-coated e.g. to improve taste, to provide ease of swallowing and an elegant appearance. Many suitable polymeric film-coating materials are known in the art. In an aspect, the film-coating material is contains a polyvinyl alcohol-polyethylene glycol (PVA-PEG) copolymer. Other suitable film-forming polymers also may be used herein, including, hydroxypropylcellulose, hydroxypropyl methylcellulose (HPMC), especially HPMC 2910 5 mPa·s, and acrylate-methacrylate copolymers. Besides a film-forming polymer, the film coat may further comprise a plasticizer (e.g. glyceryl monocaprylocaprate or propylene glycol) and optionally a pigment (e.g. titanium dioxide). The film-coating suspension also may contain talc as an anti-adhesive. In an aspect, in tablets as described herein, the film coat in terms of weight is about 3 w/w %) of the tablet weight. In an aspect, the weight of the uncoated tablet represents 100%, and the weight of the coated tablet represents 103%. In an aspect, coating of the tablet provides for a weight gain of 3 w/w %.

In an aspect, the tablet as described herein is an oval-shaped tablet.

In an aspect the tablet as described herein, in particular the uncoated tablet, is oval and has a length that is smaller than 22 mm, in particular smaller than 21 mm, in particular has a length of 20.50 mm.

In an aspect the tablet as described herein, in particular the uncoated tablet, is oval and has a width that is smaller than 12 mm, in particular smaller than 11 mm, in particular has a width of 10.25 mm.

In an aspect the tablet as described herein, in particular the uncoated tablet, is oval and has a length that is smaller than 22 mm and a width that is smaller than 12 mm, in particular a length that is smaller than 21 mm and a width that is smaller than 11 mm, in particular has a length of 20.50 mm and a width of 10.25 mm.

In an aspect the tablet as described herein, in particular the uncoated tablet, has the following dimensions: 20.50 mm×10.25 mm.

In an aspect, there is provided a process for preparing a tablet as described herein, comprising the steps of mixing apalutamide and a polymer selected from HPMCAS, a poly(meth)acrylate copolymer or a mixture of HPMCAS and a poly(meth)acrylate copolymer, in particular HPMCAS, in a suitable solvent and spray drying or melt extruding, in particular spray-drying, said mixture to produce the solid dispersion, blending the solid dispersion and a pharmaceutically acceptable carrier, and compressing said blend into a tablet.

In an aspect, the process of preparing solid dispersions as described herein, comprises blending apalutamide and a polymer selected from HPMCAS, a poly(meth)acrylate copolymer or a mixture of HPMCAS and a poly(meth) acrylate copolymer, in particular HPMCAS, and extruding said blend at a temperature in the range from about 160° C. to about 190° C.

In an aspect, the process of preparing particles as described herein, comprises blending apalutamide and a polymer selected from HPMCAS, a poly(meth)acrylate copolymer or a mixture of HPMCAS and a poly(meth) acrylate copolymer, in particular HPMCAS, extruding said blend at a temperature in the range from about 160° C. to about 190° C., grinding the extrudate, and optionally sieving the particles.

Suitable extruders that may be used are the Haake mini-extruder, Leistritz 18 mm extruder, and the Leistritz 27 mm extruder.

In an aspect, the process of preparing particles or solid dispersions as described herein comprises mixing apalutamide and a polymer selected from HPMCAS, a poly(meth) acrylate copolymer or a mixture of HPMCAS and a poly (meth)acrylate copolymer, in particular HPMCAS, in a suitable solvent and spray drying said mixture. In an aspect, the suitable solvent is a mixture of dichloromethane (methylene chloride) and methanol. In an aspect, the suitable solvent is a mixture of dichloromethane and methanol wherein the weight:weight ratio of dichloromethane to methanol in the mixture is 4:6 or 5:5, 4:6 being preferred.

Any crystalline form of apalutamide e.g. the crystalline forms as described in WO2013/184681, can be used for preparing the solid dispersions or particles as described herein. A preferred crystalline form of apalutamide for preparing the solid dispersions or particles are those described in WO2013/184681, which is incorporated herein by reference, including Form A, Form B, Form C, Form D, Form E, Form F, Form G, Form H, Form I, and Form J. In an aspect, Form B is used. Form B is an anhydrous crystalline form. In an aspect, Form A is used. Other crystalline forms include those described in WO2016/124149, WO2020/049598, WO2020/188,399, WO2019/016747, and United States Patent Applications 20190322640 and 20220281836 each of which is incorporated herein by reference.

In an aspect, there is provided a process of preparing a pharmaceutical formulation as described herein, in particular in the form of a tablet or a capsule, characterized by blending a therapeutically effective amount of a solid dispersion or particles as described herein, with a pharmaceutically acceptable carrier and compressing said blend into tablets or filling said blend in capsules.

Further, provided herein is a pharmaceutical formulation, e.g. a tablet, as described herein, for use in the treatment of an androgen receptor (AR)-related disease or condition, in particular cancer, more in particular for use in the treatment of prostate cancer, including but not limited to castration-resistant prostate cancer, metastatic castration resistant prostate cancer, metastatic castration-sensitive prostate cancer, chemotherapy-naive metastatic castration resistant prostate cancer, biochemically relapsed hormone sensitive prostate cancer, high-risk, non-metastatic castration-resistant prostate cancer or non-metastatic castration resistant prostate cancer. In an aspect, provided herein is a pharmaceutical formulation, e.g. a tablet, as described herein, for use in the treatment of non-metastatic castration resistant prostate cancer or metastatic castration-sensitive prostate cancer. In an aspect, the pharmaceutical formulation, e.g. the tablet, is administered orally, in particular orally once daily, to a subject, in particular a mammal, in particular a human, in need thereof, e.g. a cancer patient, in particular a prostate cancer patient.

In an aspect, provided herein is the use of a pharmaceutical formulation, e.g. a tablet, as described herein for the manufacture of a medicament for the treatment of an androgen receptor (AR)-related disease or condition, in particular cancer, more in particular for the treatment of prostate cancer, including but not limited to castration-resistant prostate cancer, metastatic castration resistant prostate cancer, metastatic castration-sensitive prostate cancer, chemotherapy-naive metastatic castration resistant prostate cancer, biochemically relapsed hormone sensitive prostate cancer, high-risk, non-metastatic castration-resistant prostate cancer or non-metastatic castration resistant prostate cancer. In an aspect, provided herein is the use of a pharmaceutical formulation, e.g. a tablet, as described herein, for the manufacture of a medicament for the treatment of non-metastatic castration resistant prostate cancer or metastatic castration-sensitive prostate cancer. In an aspect, the pharmaceutical formulation, e.g. the tablet, is administered orally, in particular orally once daily, to a subject, in particular a mammal, in particular a human, in need thereof, e.g. a cancer patient, in particular a prostate cancer patient.

In an aspect, provided herein is a method of treating an androgen receptor (AR)-related disease or condition, in particular cancer, more in particular prostate cancer, including but not limited to castration-resistant prostate cancer, metastatic castration resistant prostate cancer, metastatic castration-sensitive prostate cancer, chemotherapy-naive metastatic castration resistant prostate cancer, biochemically relapsed hormone sensitive prostate cancer, high-risk, non-metastatic castration-resistant prostate cancer, or non-metastatic castration resistant prostate cancer, in a mammal, in particular a human, which comprises administering, in particular orally, in particular orally once daily, to said mammal, in particular human, in need thereof, e.g. a cancer patient, in particular a prostate cancer patient, a pharmaceutical formulation as described herein.

In an aspect the pharmaceutical formulations, e.g. the tablets, as described herein are administered in non-carbonated water, or in orange juice, green tea, yoghurt or applesauce.

In an aspect, for patients who cannot swallow tablets whole, the tablets, as described herein, in particular the tablet containing 240 mg of apalutamide, may be dispersed in water (non-carbonated water) and then mixed with additional water (non-carbonated water), orange juice, green tea, yoghurt or applesauce. In an aspect, for patients who cannot swallow tablets whole, the tablets, as described herein, in particular the tablet containing 240 mg of apalutamide, may be mixed with orange juice before administration, in particular the tablets may be dispersed in water (non-carbonated water) and then mixed with orange juice. In an aspect, for patients who cannot swallow tablets whole, the tablets, as described herein, in particular the tablet containing 240 mg of apalutamide, may be mixed with applesauce before administration, in particular the tablets may be dispersed in water (non-carbonated water) and then mixed with apple sauce. In an aspect, for patients who cannot swallow tablets whole, the tablets, as described herein, in particular the tablet containing 240 mg of apalutamide, may be mixed with green tea before administration, in particular the tablets may be dispersed in water (non-carbonated water) and then mixed with green tea. In an aspect, for patients who cannot swallow tablets whole, the tablets, as described herein, in particular the tablet containing 240 mg of apalutamide, may be mixed with yoghurt before administration, in particular the tablets may be dispersed in water (non-carbonated water) and then mixed with yoghurt. In an aspect, for patients who cannot swallow tablets whole, the tablets, as described herein, in particular the tablet containing 240 mg of apalutamide, may be mixed with water (non-carbonated water) before administration, in particular the tablets may be dispersed in water (non-carbonated water) and then mixed with additional water.

In an aspect, for patients who cannot swallow tablets whole, the tablets, as described herein, in particular the tablet containing 240 mg of apalutamide, may be mixed with water (non-carbonated water) before administration, in particular the tablets may be dispersed in water (non-carbonated water) and then mixed with orange juice or apple sauce.

In an aspect, for patients who cannot swallow the tablet whole, the recommended dose of one 240 mg tablet can be dispersed in non-carbonated water and then administered with a liquid or soft food selected from either orange juice, green tea, yoghurt, apple sauce or additional water as follows:

1. Place the whole 240 mg apalutamide tablet as described herein in a cup. Do not crush or split the tablet.
2. Add about 2 teaspoons (10 mL) of non-carbonated water to make sure that the tablet is completely immersed in water.
3. Wait 2 minutes until the tablet is broken up and spread out, then stir the mixture.
4. Add 2 tablespoons (30 mL) of either orange juice, green tea, yoghurt, applesauce or additional water, in particular orange juice, applesauce or additional water, and stir the mixture.
5. Swallow the mixture immediately.
6. Rinse the cup with enough water to make sure the whole dose is taken and drink it immediately.

In an aspect, there is provided a pharmaceutical package suitable for commercial sale comprising a container, a pharmaceutical formulation as described herein, and associated with said package written matter.

In an aspect, the pharmaceutical formulations, e.g. the tablets, as described herein, are contained in a high-density polyethylene (HDPE) bottle (white) with child-resistant (CR) polypropylene (PP) closure and induction seal liner. In an aspect, each such bottle contains a desiccant (Silica gel 2 gram (silicon dioxide) e.g. in HDPE pouch). In an aspect, the liner is a multilayer structure. In an aspect, the heat seal layer which is in contact with the tablets consists of polyethylene. In an aspect, the materials of construction of the container closure system, including the heat seal liner comply with the applicable active European Directives and/or Regulations related to articles and materials intended to be in contact with foodstuffs or drugs and their amendments (EU/10/2011 and EC 1935/2004). In an aspect, the materials of construction of the container closure system, including the heat seal liner comply with the applicable active directives and/or regulations for materials in contact with foodstuffs or drugs and meets the requirements of FDA title 21 CFR 177.1520 on Olefin polymers and the requirements of FDA title 21 CFR 178.3297 on colorants for polymers. In an aspect, the bottle is a 75 mL bottle. In an aspect, each such bottle contains 30 tablets.

In an aspect, the pharmaceutical formulations, e.g. the tablets, as described herein, are contained in a transparent polyvinylchloride (PVC)/polychlorotrifluoroethylene (PCTFE) film blister with an aluminum (Alu) push-through foil. In an aspect, the blister consists of following materials:

*PVC-PCTFE film (food-approved):

Polyvinyl chloride (inner layer, product contact)

Polychlorotrifluoroethylene (outer layer)

Alu foil:

Aluminium

Heat-seal coating: food-approved (product contact layer).

In an aspect, the PVC/PCTFE film is compliant with the European Regulation for materials intended to come into contact with food EC 1935/2004, including Regulation (EU) No 10/2011 on Plastic Materials and Articles Intended to Come into Contact with Food.

In an aspect, the PVC/PCTFE film is compliant with the applicable directives and/or regulations for materials in contact with foodstuffs or drugs and meets the requirements of FDA title 21 CFR 174 through 178.

Provided herein are methods of selling an approved drug product, said method comprising selling such approved drug product, wherein an approved drug product label for a reference listed drug (RLD) for such approved drug product includes instructions for the treatment of patients with metastatic castration-sensitive prostate cancer (mCSPC) or non-metastatic castration-resistant prostate cancer (nm-CRPC). In certain embodiments, the approved drug product is an ANDA approved drug product, a supplemental New Drug Application approved drug product or a 505(b)(2) approved drug product.

The term "approved drug product" or "drug product" is a pharmaceutical formulation that contains 240 mg apalutamide in a single oral dosage form, which has been approved for marketing for at least one indication by a governmental authority, e.g., the Food and Drug Administration or the similar authority in other countries.

The term "reference listed drug (RLD)" is an approved drug product to which new generic versions are compared to show that they are bioequivalent. (21 CFR 314.3(b)) It is also a medicinal product that has been granted marketing authorization by a member state of the European Union or by the EU Commission on the basis of a completed dossier, i.e., with the submission of quality, pre-clinical and clinical data in accordance with Articles 8(3), 10a, 10b or 10c of Directive 2001/83/EC and to which the application for marketing authorization for a generic/hybrid medicinal product refers, by demonstration of bioequivalence, usually through the submission of the appropriate bioavailability studies.

In the United States, a company seeking approval to market a generic equivalent must refer to the RLD in its Abbreviated New Drug Application (ANDA). For example, an ANDA applicant relies on the FDA's finding that a previously approved drug product, i.e., the RLD, is safe and effective, and must demonstrate, among other things, that the proposed generic approved drug product is the same as the RLD in certain ways. Specifically, with limited exceptions, an approved drug product for which an ANDA is submitted must have, among other things, the same active ingredient(s), conditions of use, route of administration, dosage form, strength, and (with certain permissible differences) labeling as the RLD. The RLD is the listed drug to which the ANDA applicant must show its proposed ANDA approved drug product is the same with respect to active ingredient(s), dosage form, route of administration, strength, labeling, and conditions of use, among other characteristics. In the electronic Orange Book, there is a column for RLDs and a column for reference standards. In the printed version of the Orange Book, the RLDs and reference standards are identified by specific symbol. For an ANDA based on an approved suitability petition (a petitioned ANDA), the reference listed drug generally is the listed drug referenced in the approved suitability petition.

A reference standard is the approved drug product selected by FDA that an applicant seeking approval of an ANDA must use in conducting an in vivo bioequivalence study required for approval. FDA generally selects a single reference standard that ANDA applicants must use in in vivo bioequivalence testing. Ordinarily, FDA will select the reference listed drug as the reference standard. However, in some instances (e.g., where the reference listed drug has been withdrawn from sale and FDA has determined it was not withdrawn for reasons of safety or effectiveness, and FDA selects an ANDA as the reference standard), the reference listed drug and the reference standard may be different.

FDA identifies reference listed drugs in the Prescription Approved drug product, OTC Approved drug product, and Discontinued Approved drug product Lists. Listed drugs identified as reference listed drugs represent approved drug products upon which an applicant can rely in seeking approval of an ANDA. FDA intends to update periodically the reference listed drugs identified in the Prescription Approved drug product, OTC Approved drug product, and Discontinued Approved drug product Lists, as appropriate.

FDA also identifies reference standards in the Prescription Approved drug product and OTC Approved drug product Lists. Listed drugs identified as reference standards represent the FDA's best judgment at this time as to the appropriate comparator for purposes of conducting any in vivo bioequivalence studies required for approval.

In some instances when FDA has not designated a listed drug as a reference listed drug, such listed drug may be shielded from generic competition. If FDA has not designated a reference listed drug for an approved drug product the applicant intends to duplicate, the potential applicant may ask FDA to designate a reference listed drug for that approved drug product.

FDA may, on its own initiative, select a new reference standard when doing so will help to ensure that applications for generic drugs may be submitted and evaluated, e.g., in the event that the listed drug currently selected as the reference standard has been withdrawn from sale for other than safety and efficacy reasons.

The different abbreviated approval pathways for approved drug products under the FD&C Act include the abbreviated approval pathways described in section 505( ) and 505(b)(2) of the FD&C Act (21 U.S.C. 355( ) and 21 U.S.C. 23 355(b)(2), respectively).

According to the FDA (https://www.fda.gov/downloads/Drugs/GuidanceComplianceRegulatoryInformation/Guid ances/UCM579751.pdf), the contents of which is incorporated herein by reference, NDAs and ANDAs can be divided into the following four categories:

(1) A "stand-alone NDA" is an application submitted under section 505(b)(1) and approved under section 505(c) of the FD&C Act that contains full reports of investigations of safety and effectiveness that were conducted by or for the applicant or for which the applicant has a right of reference or use.

(2) A 505(b)(2) application is an NDA submitted under section 505(b)(1) and approved under section 505(c) of the FD&C Act that contains full reports of investigations of safety and effectiveness, where at least some of the information required for approval comes from studies not conducted by or for the applicant and for which the applicant has not obtained a right of reference or use.

(3) An ANDA is an application for a duplicate of a previously approved drug product that was submitted and approved under section 505(j) of the FD&C Act. An ANDA relies on FDA's finding that the previously approved drug product, i.e., the reference listed drug (RLD), is safe and effective. An ANDA generally must contain information to show that the proposed generic product (a) is the same as the RLD with respect to the active ingredient(s), conditions of use, route of administration, dosage form, strength, and labeling (with certain permissible differences) and (b) is bioequivalent to the RLD. An ANDA may not be submitted if studies are necessary to establish the safety and effectiveness of the proposed product.

(4) A petitioned ANDA is a type of ANDA for an approved drug product that differs from the RLD in its dosage form, route of administration, strength, or active ingredient (in a product with more than one active ingredient) and for which FDA has determined, in response to a petition submitted under section 505(j)(2)(C) of the FD&C Act (suitability petition), that studies are not necessary to establish the safety and effectiveness of the proposed approved drug product.

A scientific premise underlying the Hatch-Waxman Amendments is that an approved drug product approved in an ANDA under section 505(j) of the FD&C Act is presumed to be therapeutically equivalent to its RLD. Products classified as therapeutically equivalent can be substituted with the full expectation that the substituted product will produce the same clinical effect and safety profile as the prescribed product when administered to patients under the conditions specified in the labeling. In contrast to an ANDA, a 505(b)(2) application allows greater flexibility as to the characteristics of the proposed product. A 505(b)(2) application will not necessarily be rated therapeutically equivalent to the listed drug it references upon approval.

In Europe, Applicants identify in the application form for its generic/hybrid medicinal product, which is the same as a ANDA or sNDA approved drug product, the reference medicinal product (product name, strength, pharmaceutical form, Marketing Authorisation Holder (MAH), first authorization, Member State/Community), which is synonymous with a RLD, as follows:

1. The medicinal product that is or has been authorized in the EEA, used as the basis for demonstrating that the data protection period defined in the European pharmaceutical legislation has expired. This reference medicinal product, identified for the purpose of calculating expiry of the period of data protection, may be for a different strength, pharmaceutical form, administration route or presentation than the generic/hybrid medicinal product.

2. The medicinal product, the dossier of which is cross-referred to in the generic/hybrid application (product name, strength, pharmaceutical form, MAH, marketing authorization number). This reference medicinal product may have been authorized through separate procedures and under a different name than the reference medicinal product identified for the purpose of calculating expiry of the period of data protection. The product information of this reference medicinal product will, in principle, serve as the basis for the product information claimed for the generic/hybrid medicinal product.

3. The medicinal product (product name, strength, pharmaceutical form, MAH, Member State of source) used for the bioequivalence study(ies) (where applicable).

The term "therapeutically equivalent to a reference listed drug" means that the approved drug product is a generic equivalent, i.e., pharmaceutical equivalents, of the reference listed approved drug product and, as such, is rated an AB therapeutic equivalent to the reference listed approved drug product by the FDA whereby actual or potential bioequivalence problems have been resolved with adequate in vivo and/or in vitro evidence supporting bioequivalence.

"Pharmaceutical equivalents" means approved drug products in identical dosage forms and route(s) of administration that contain identical amounts of the identical active drug ingredient as the reference listed drug.

FDA classifies as therapeutically equivalent those products that meet the following general criteria: (1) they are approved as safe and effective; (2) they are pharmaceutical equivalents in that they (a) contain identical amounts of the same active drug ingredient in the same dosage form and route of administration, and (b) meet compendial or other applicable standards of strength, quality, purity, and identity; (3) they are bioequivalent in that (a) they do not present a known or potential bioequivalence problem, and they meet an acceptable in vitro standard, or (b) if they do present such a known or potential problem, they are shown to meet an appropriate bioequivalence standard; (4) they are adequately labeled; and (5) they are manufactured in compliance with Current Good Manufacturing Practice regulations The term "bioequivalent" or "bioequivalence" is the absence of a significant difference in the rate and extent to which the active ingredient or active moiety in pharmaceutical equivalents or pharmaceutical alternatives becomes available at the site of drug action when administered at the same molar dose under similar conditions in an appropriately designed study. Section 505 (j)(8)(B) of the FD&C Act describes one set of conditions under which a test and reference listed drug shall be considered bioequivalent:

the rate and extent of absorption of the [test] drug do not show a significant difference from the rate and extent of absorption of the [reference] drug when administered at the same molar dose of the therapeutic ingredient under similar experimental conditions in either a single dose or multiple doses; or the extent of absorption of the [test] drug does not show a significant difference from the extent of absorption of the [reference] drug when administered at the same molar dose of the therapeutic ingredient under similar experimental conditions in either a single dose or multiple doses and the difference from the [reference] drug in the rate of absorption of the drug is intentional, is reflected in its proposed labeling, is not essential to the attainment of effective body drug concentrations on chronic use, and is considered medically insignificant for the drug.

Where these above methods are not applicable (e.g., for approved drug products that are not intended to be absorbed into the bloodstream), other scientifically valid in vivo or in vitro test methods to demonstrate bioequivalence may be appropriate.

For example, bioequivalence may sometimes be demonstrated using an in vitro bioequivalence standard, especially when such an in vitro test has been correlated with human in vivo bioavailability data. In other situations, bioequivalence may sometimes be demonstrated through comparative clinical trials or pharmacodynamic studies.

The terms "sale" or "selling" means transferring an approved drug product, e.g., a pharmaceutical composition or an oral dosage form, from a seller to a buyer.

The term "offering for sale" means the proposal of a sale by a seller to a buyer for an approved drug product, e.g., a pharmaceutical composition and an oral dosage form.

Further provided herein are methods of offering for sale an approved drug product, said method comprising offering for sale such approved drug product, wherein an approved drug product label for a reference listed drug for such approved drug product includes instructions for treating the treatment of patients with metastatic castration-sensitive prostate cancer (mCSPC) or non-metastatic castration-resistant prostate cancer (nmCRPC). In certain embodiments, the approved drug product is an ANDA approved drug product, a supplemental New Drug Application approved drug product or a 505(b)(2) approved drug product.

Also described herein are methods comprising selling an approved drug product wherein the approved drug product label for a reference listed drug for such approved drug product comprises: TITAN (NCT02489318): Metastatic Castration-sensitive Prostate Cancer (mCSPC) TITAN was a randomized, double-blind, placebo-controlled, multinational, clinical trial in which 1052 patients with mCSPC were randomized (1:1) to receive either ERLEADA orally at a dose of 240 mg once daily (N=525) or placebo once daily (N=527). All patients in the TITAN trial received concomitant GnRH analog or had prior bilateral orchiectomy. Patients were stratified by Gleason score at diagnosis, prior docetaxel use, and region of the world. Patients with both high- and low-volume mCSPC were eligible for the study. High volume of disease was defined as metastases involving the viscera with 1 bone lesion or the presence of 4 or more bone lesions, at least 1 of which must be in a bony structure beyond the vertebral column and pelvic bones.

The following patient demographics and baseline disease characteristics were balanced between the treatment arms. The median age was 68 years (range 43-94) and 23% of patients were 75 years of age or older. The racial distribution was 68% Caucasian, 22% Asian, and 2% Black. Sixty-three percent (63%) of patients had high-volume disease and 37% had low-volume disease. Sixteen percent (16%) of patients had prior surgery, radiotherapy of the prostate or both. A majority of patients had a Gleason score of 8 or higher (67%). Sixty-eight percent (68%) of patients received prior treatment with an anti-androgen (bicalutamide, flutamide, or nilutamide). All patients except one in the placebo group, had an Eastern Cooperative Oncology Group Performance Status (ECOG PS) score of 0 or 1 at study entry.

The major efficacy outcome measures of the study were overall survival (OS) and radiographic progression-free survival (rPFS). Radiographic progression-free survival was based on investigator assessment and was defined as time from randomization to radiographic disease progression or death. Radiographic disease progression was defined by identification of 2 or more new bone lesions on a bone scan with confirmation (Prostate Cancer Working Group 2 criteria) and/or progression in soft tissue disease.

A statistically significant improvement in OS and rPFS was demonstrated in patients randomized to receive ERLEADA compared with patients randomized to receive placebo. The results for OS are based upon a prespecified interim efficacy analysis. An updated OS analysis was conducted at the time of final study analysis when 405 deaths were observed. The median follow-up time was 44 months. Thirty-nine percent of patients in the placebo arm crossed over to receive ERLEADA. Efficacy results of TITAN are summarized in the below Table 1A and FIGS. 7 and 8.

TABLE 1A

Efficacy Results from the TITAN Study

| Endpoint | ERLEADA (N = 525) | Placebo (N = 527) |
|---|---|---|
| Primary Overall Survival[a] | | |
| Deaths (%) | 83 (16%) | 117 (22%) |
| Median, months (95% CI)[b] | NE (NE, NE) | NE (NE, NE) |
| Hazard Ratio (95% CI)[c] | 0.67 (0.51, 0.89) | |
| p-value[d] | 0.0053 | |
| Updated Overall Survival | | |
| Deaths (%) | 170 (32%) | 235 (45%) |
| Median, months (95% CI)[b] | NE (NE, NE) | 52 (42, NE) |
| Hazard Ratio (95% CI)[c] | 0.65 (0.53, 0.79) | |
| Radiographic Progression-free Survival | | |
| Disease progression or death (%) | 134 (26%) | 231 (44%) |
| Median, months (95% CI)[b] | NE (NE, NE) | 22.1 (18, 33) |
| Hazard Ratio (95% CI)[c] | 0.48 (0.39, 0.60) | |
| p-value[d] | <0.0001 | |

[a]Interim analysis is based on 50% of the number of events planned for the final analysis. Allocated alpha = 0.01.
[b]NE = Not Estimable
[c]Hazard ratio is from stratified proportional hazards model. Hazard ratio <1 favors ERLEADA.
[d]p-value is from the log-rank test stratified by Gleason score at diagnosis (≤7 vs. >7), Region (NA/EU vs. Other Countries) and Prior docetaxel use (Yes vs. No).

Consistent improvement in rPFS was observed across the following patient subgroups: disease volume (high vs low), prior docetaxel use (yes or no), and Gleason score at diagnosis (<7 vs. >7).

Consistent improvement in OS was observed across the following patient subgroups: disease volume (high vs low) and Gleason score at diagnosis (57 vs. >7).

Treatment with ERLEADA resulted in a statistically significant delay in the initiation of cytotoxic chemotherapy (HR=0.39, 95% CI=0.27, 0.56; p<0.0001).

SPARTAN (NCTO01946204): Non-metastatic, Castration-resistant Prostate Cancer (nmCRPC) SPARTAN was a multicenter, double-blind, randomized (2:1), placebo-controlled clinical trial in which 1207 patients with nmCRPC were randomized (2:1) to receive either ERLEADA orally at a dose of 240 mg once daily (N=806) or placebo once daily (N=401). All patients in the SPARTAN trial received a concomitant GnRH analog or had a bilateral orchiectomy. Patients were stratified by Prostate Specific Antigen (PSA) Doubling Time (PSADT), the use of bone-sparing agents, and locoregional disease. Patients were required to have a PSADT <10 months and confirmation of non-metastatic disease by blinded independent central review (BICR). PSA results were blinded and were not used for treatment discontinuation. Patients randomized to either arm discontinued treatment for radiographic disease progression confirmed by BICR, locoregional-only progression, initiation of new treatment, unacceptable toxicity, or withdrawal.

The following patient demographics and baseline disease characteristics were balanced between the treatment arms. The median age was 74 years (range 48-97) and 26% of patients were 80 years of age or older. The racial distribution was 66% Caucasian, 12% Asian, and 6% Black. Seventy-seven percent (77%) of patients in both treatment arms had prior surgery or radiotherapy of the prostate. A majority of patients had a Gleason score of 7 or higher (78%). Fifteen percent (15%) of patients had <2 cm pelvic lymph nodes at study entry. Seventy-three percent (73%) of patients received prior treatment with an anti-androgen; 69% of patients received bicalutamide and 10% of patients received flutamide.

All patients had an Eastern Cooperative Oncology Group Performance Status (ECOG PS) score of 0 or 1 at study entry.

The major efficacy outcome measure of the study was metastasis-free survival (MFS), defined as the time from randomization to the time of first evidence of BICR-confirmed distant metastasis, defined as new bone or soft tissue lesions or enlarged lymph nodes above the iliac bifurcation, or death due to any cause, whichever occurred first. Additional efficacy endpoints were time to metastasis (TTM), progression-free survival (PFS) which also includes locoregional progression, time to symptomatic progression, overall survival (OS), and time to initiation of cytotoxic chemotherapy.

A statistically significant improvement in MFS and OS was demonstrated in patients randomized to receive ERLEADA compared with patients randomized to receive placebo. The major efficacy outcome (MFS) was supported by improvements in TTM and PFS. The final analysis of OS and time to initiation of cytotoxic chemotherapy was conducted 32 months after the analysis of MFS, TTM and PFS. The efficacy results from SPARTAN are summarized in the below Table 1B and FIGS. 9 and 10.

TABLE 1B

Efficacy Results from the SPARTAN Study

| Endpoint | ERLEADA (N = 806) | Placebo (N = 401) |
|---|---|---|
| Metastasis Free Survival[a, b, c] | | |
| Number of Events (%) | 184 (23%) | 194 (48%) |
| Median, months (95% CI)[d] | 40.5 (NE, NE) | 16.2 (15, 18) |
| Hazard Ratio (95% CI) | 0.28 (0.23, 0.35) | |
| p-value[a] | <0.0001 | |

TABLE 1B-continued

| Efficacy Results from the SPARTAN Study | | |
|---|---|---|
| Endpoint | ERLEADA (N = 806) | Placebo (N = 401) |
| Time to Metastasis[a, b] | | |
| Number of Events (%) | 175 (22%) | 191 (48%) |
| Median, months (95% CI)[d] | 40.5 (NE, NE) | 16.6 (15, 18) |
| Hazard Ratio (95% CI) | 0.27 (0.22, 0.34) | |
| p-value[a] | <0.0001 | |
| Progression-Free Survival[a, b] | | |
| Number of Events (%) | 200 (25%) | 204 (51%) |
| Median, months (95% CI)[d] | 40.5 (NE, NE) | 14.7 (14, 18) |
| Hazard Ratio (95% CI) | 0.29 (0.24, 0.36) | |
| p-value[a] | <0.0001 | |
| Overall Survival | | |
| Number of Events (%) | 274 (34%) | 154 (38%) |
| Median, months (95% CI)[d] | 73.9 (61, NE) | 59.9 (53, NE) |
| Hazard Ratio (95% CI) | 0.78 (0.64, 0.96) | |
| p-value[a] | 0.0161 | |

[a]All analyses stratified by PSA doubling time, bone-sparing agent use, and locoregional disease status.
[b]Confirmed responses assessed by BICR.
[c]Locoregional-only progression is observed in 2.4% of patients overall.
[d]NE = Not Estimable Consistent results for MFS were observed across patient subgroups including PSADT (≤6 months or >6 months), use of a prior bone-sparing agent (yes or no), and locoregional disease (N0 or N1).

Treatment with ERLEADA resulted in a statistically significant delay in the initiation of cytotoxic chemotherapy [HR=0.63 (95% CI:0.49, 0.81), p=0.0002].

In certain embodiments, the approved drug product label for a reference listed drug for such approved drug product comprises metastasis-free survival data.

The following examples are intended to illustrate the present invention.

Example 1: Apalutamide Forms

For the preparation of different (crystalline) forms of apalutamide, reference is made to WO2013/184681, which is incorporated herein by reference. Different (crystalline or amorphous) forms of apalutamide can be used to prepare the solid dispersions, particles or formulations described herein.

A preferred form of apalutamide for use in the preparation of the solid dispersions, particles or formulations described herein is apalutamide Form B, which is an anhydrous crystal. It was prepared by suspending apalutamide Form A (reference is made to WO2013/184681, including for the diffraction data) in USP water and heating the slurry to 55±5° C., holding at said temperature for at least 24 hours, followed by cooling the slurry to 25±5° C. The resulting slurry was filtered, and the wet cake washed once with USP water. The wet cake was unloaded from the filter and dried under vacuum to afford apalutamide Form B. Reference is also made to Example 2 below.

Solubility of Form A: 0.01 mg/ml in water.

Solubility of Form B: 0.004 mg/ml in water.

Example 2

Characterisation of Apalutamide Form B

Powder XRD

X-ray powder diffraction (XRPD) analyses were carried out on a PANalytical (Philips) X'PertPRO MPD diffractometer. The instrument is equipped with a Cu LFF X-ray tube. The compound was spread on a zero background sample holder.

Instrument Parameters
- generator voltage: 45 kV
- generator amperage: 40 mA
- geometry: Bragg-Brentano
- stage: spinner stage Measurement Conditions
- scan mode: continuous
- scan range: 3 to 50° 2θ
- step size: 0.02°/step
- counting time: 30 sec/step
- spinner revolution time: 1 sec
- radiation type: CuKα

| Incident beam path | | Diffracted beam path | |
|---|---|---|---|
| program. divergence slit: | 15 mm | long anti scatter shield: | + |
| Soller slit: | 0.04 rad | Soller slit: | 0.04 rad |
| beam mask: | 15 mm | Ni filter: | + |
| anti scatter slit: | 1° | detector: | X'Celerator |
| beam knife: | + | | |

The X-ray powder diffraction pattern of apalutamide Form B shows diffraction peaks without the presence of a halo, indicating that this compound is present as a crystalline product. The XRD pattern of apalutamide Form B is shown in FIG. 1.

Infrared Spectrometry (Micro ATR-IR)

Figure 2:
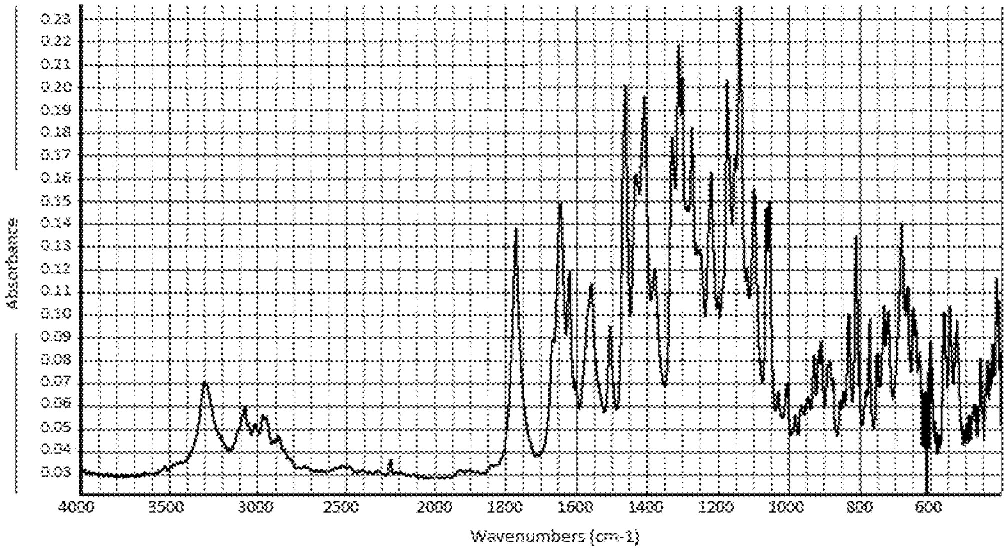
FIG. 2 IR spectrum of apalutamide Form B.

The samples were analyzed using a suitable microATR accessory.
- apparatus: Thermo *Nexus* 670 FTIR spectrometer
- number of scans: 32
- resolution: 1 $cm^{-1}$
- wavelength range: 4000 to 400 $cm^{-1}$
- detector: DTGS with KBr windows
- beamsplitter: Ge on KBr
- micro ATR accessory: Harrick Split Pea with Si crystal The spectrum of apalutamide Form B is shown in FIG. 2.

Differential Scanning Calorimetry (DSC)

The compound was transferred into a standard aluminum TA-Instrument sample pan. The sample pan was closed with the appropriate cover and the DSC curve was recorded on a TA-Instruments Q1000 MTDSC equipped with a RCS cooling unit, using the following parameters:
- initial temperature: 25° C.
- heating rate: 10° C./min
- final temperature: 250° C.

Figure 3:
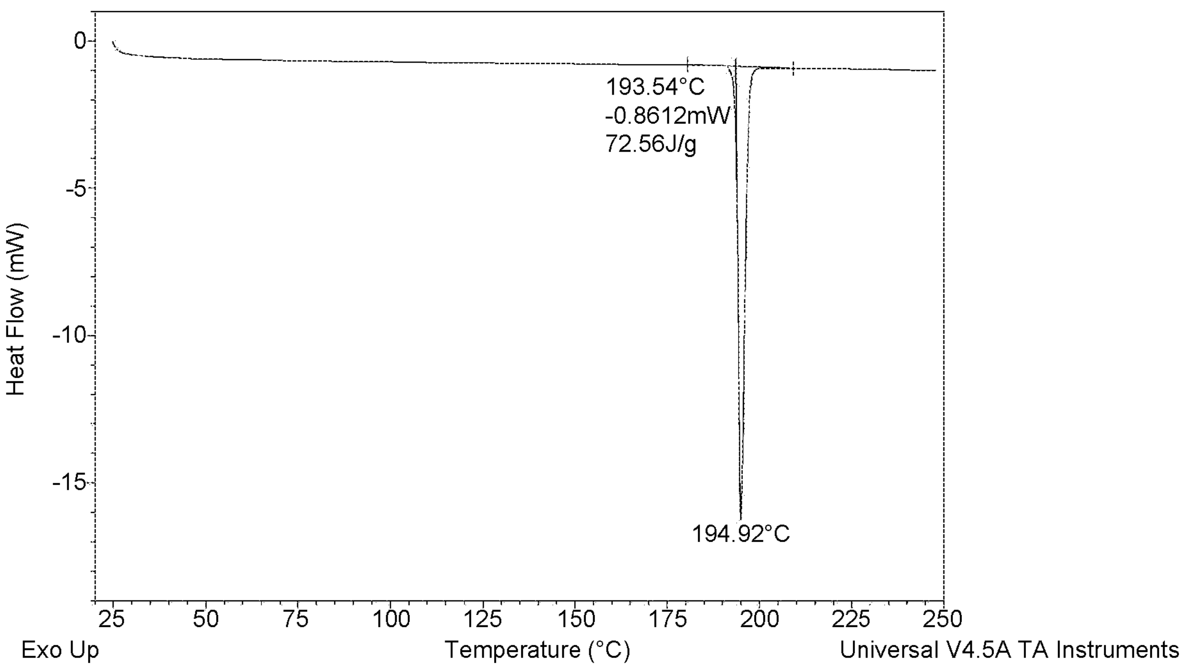
FIG. 3 DSC curve of apalutamide Form B.

The DSC curve of apalutamide Form B shows the melting of the product at 194.9° C. with a heat of fusion of 73 J/g. See FIG. 3.

Example 3.1: Preparation of a Solid Dispersion of Apalutamide:HPMCAS LG 1:3

| | |
|---|---|
| Apalutamide | 2,500 g |
| HPMC-AS LG | 7,500 g |
| Dichloromethane, [a] | 76,000 g |
| Methanol [a] | 114,000 g |

[a] Removed during processing

The dichloromethane and methanol were transferred into a suitable container and stirring was started. Under continuous stirring apalutamide Form B was added to the solvent mixture and stirred until dissolved. HPMCAS was added to the solution and stirred overnight. A yellowish viscous turbid mixture was obtained. The mixture was filtered inline through a GRID filter. The mixture was spray dried using a suitable spray dryer, e.g. Niro A/S PSD3 with a high pressure nozzle with the following parameters: feed flow of 75 kg/hour, outlet temperature of 46° C. and a condenser temperature of −9° C.

The spray dried product (SDP) was dried in a suitable dryer, e.g. tray dryer using vacuum, nitrogen flow and a drying temperature of 40° C.

This SDP is referred to hereinafter as the SDP intermediate or as 250 mg/g SDP.

Example 3.2: Preparation of Tablets Comprising the Solid Dispersion of Apalutamide:HPMCAS 1:3 According to Example 3.1

The composition of the 250 mg/g SDP is provided in Table 1.

TABLE 1

Composition of the Apalutamide 250 mg/g SDP Intermediate

| Component | Quality Reference | Function | Quantity per Gram mg | Quantity per Gram w/w (%) |
|---|---|---|---|---|
| Apalutamide | Company Specification | Active | 250.00 | 25.00 |
| HPMCAS[b] | USP/NF | Stabilizer | 750.00 | 75.00 |
| Methanol[a] | Ph. Eur., USP/NF | Process solvent | NA | NA |
| Dichloro-methane[c, a] | Ph. Eur., USP/NF | Process solvent | NA | NA |
| | Total Weight | | 1,000.00 | 100.00 |

NA = Not applicable
[a]Removed during processing
[b]Hydroxypropyl methylcellulose acetate succinate (HPMCAS) is also called hypromellose acetate succinate.
[c]Also called methylene chloride The composition of a 240 mg tablet (uncoated) comprising the 250 mg/g SDP is provided in Table 2.

TABLE 2

Composition of a 240 mg tablet (uncoated)

| Component | Quality Reference | Function | Quantity per Unit mg/tablet | Quantity per Unit w/w (%) |
|---|---|---|---|---|
| | Core Tablet: Intragranular phase | | | |
| 250 mg/g SDP[a] (of Table 1) | Company specification | Active | 960.00 | 82.40 |
| Colloidal Anhydrous Silica [b] | Ph. Eur., USP/NF | Glidant | 4.70 | 0.40 |
| Croscarmellose Sodium | Ph. Eur., USP/NF | Disintegrant | 35.00 | 3.00 |
| | Extragranular phase | | | |
| Silicified Microcrystalline Cellulose | USP/NF | Filler | 119.80 | 10.28 |
| Colloidal Anhydrous Silica [b] | Ph. Eur., USP/NF | Glidant | 4.70 | 0.40 |
| Croscarmellose Sodium | Ph. Eur., USP/NF | Disintegrant | 35.00 | 3.00 |
| Magnesium Stearate | Ph. Eur., USP/NF | Lubricant | 5.80 | 0.50 |
| | Total Core Tablet Weight | | 1165.00 | 100.00 |

[a]960 mg of SDP per tablet or 82.4% w/w contains 240 mg of apalutamide drug substance
[b] Also called colloidal silicon dioxide.

The 250 mg/g SDP was screened and the screened 250 mg/g SDP, colloidal anhydrous silica, and croscarmellose sodium was transferred into a bin and blended to obtain a homogeneous pre-compaction blend.

The pre-compaction blend was compacted using a roller compactor to obtain a granulate, which was collected in a suitable bin.

The screened silicified microcrystalline cellulose, croscarmellose sodium, and colloidal anhydrous silica was added to the granulate in the bin and blended to obtain a homogeneous post-compaction blend.

Screened magnesium stearate was added to the post-compaction blend in the bin and continue blending for lubrication purposes to obtain a homogeneous lubrication blend. The lubrication blend was compressed into tablets using a power assisted tablet press.

The resulting oval tablets debossed on one side with "E240", have a white to almost white, yellowish appearance (visual inspection); have an average[a] hardness (kp): 38-48 (hardness measurement) and an average[a] weight: 1136-1194 (weight measurement)

[a] Average of 10 tablets

Example 3.3: Preparation of Coated Tablets

The composition of a 240 mg film coated tablet comprising the tablet according to example 3.2 is provided in Table 3.

TABLE 3

| Composition of a 240 mg Film-coated Tablet | | | | |
|---|---|---|---|---|
| | | | Quantity per Unit | |
| Component | Quality Reference | Function | mg/tablet | w/w (%) |
| Core Tablet: Intragranular phase | | | | |
| 250 mg/g SDP[b] (of Table 1) | Company specification | Active | 960.00 | 82.40 |
| Colloidal Anhydrous Silica [c] | Ph. Eur., USP/NF | Glidant | 4.70 | 0.40 |
| Croscarmellose Sodium | Ph. Eur., USP/NF | Disintegrant | 35.00 | 3.00 |
| Extragranular phase | | | | |
| Silicified Microcrystalline Cellulose | USP/NF | Filler | 119.80 | 10.28 |
| Colloidal Anhydrous Silica [c] | Ph. Eur., USP/NF | Glidant | 4.70 | 0.40 |
| Croscarmellose Sodium | Ph. Eur., USP/NF | Disintegrant | 35.00 | 3.00 |
| Magnesium Stearate | Ph. Eur., USP/NF | Lubricant | 5.80 | 0.50 |
| Total Core Tablet Weight | | | 1165.00 | 100.00 |
| Film-Coat: | | | | |
| Polyvinyl alcohol-polyethylene glycol (PVA-PEG) copolymer based coating powder | Coating Powder | | 34.95 | 3.00 |
| Purified Water[a] | Ph. Eur., USP/NF | Process Solvent | NA | NA |
| Total Tablet weight | | | 1199.95 | 103.00 |

[a]Removed during processing
NA = Not applicable
[b]960 mg of SDP per tablet or 82.4% w/w contains 240 mg of apalutamide drug substance
[c] Also called colloidal silicon dioxide.

Purified water and coating powder was transferred into a suitable vessel and stirred to obtain a homogeneous coating suspension.

The coating suspension was sprayed onto the core tablets using a perforated coating pan system with exhaust air temperature (° C.): 43-53, to obtain film-coated tablets.

The resulting oval-film coated tablets debossed with "E240" on one side have a bluish grey to grey appearance (visual inspection).

Table 4 shows that all excipients of the uncoated tablet were used at levels below the maximum potencies listed in Food and Drug Administration's Inactive Ingredients Database (IID) for approved drug products for oral administration.

| Component | Total Daily Intake[a] (mg) | Maximum Potency[b] (mg/day) |
|---|---|---|
| Core Tablet | | |
| HPMC-AS | 720.00 | 4,480.00 |
| Colloidal Anhydrous Silica[c] | 11.80[d] | 2,553.00 |
| Croscarmellose Sodium | 70.00 | 1,653.00 |
| Microcrystalline Cellulose | 117.40[d] | 29,520.00 |
| Magnesium Stearate | 5.80 | 629.00 |

[a]The Total Daily Intake is based on a daily dose of 1 tablet of 240 mg, indicating the same amount per unit of drug product.
[b]The highest levels have been selected among the different oral dosage forms listed in the IID.
[c]Also called colloidal silicon dioxide
[d]As silicified microcrystalline cellulose is a mixture of colloidal anhydrous silica (2% w/w) and microcrystalline cellulose (98% w/w), the contributions from the silicified microcrystalline cellulose used in the drug product have been added to the respective individual excipients.

The above 240 mg film coated tablets may be contained in a container closure system being a white high-density polyethylene (HDPE) bottle with child-resistant (CR) polypropylene (PP) closure and induction seal liner. Each bottle may contain 30 tablets and a desiccant (Silica gel 2 gram (silicon dioxide) in HDPE pouch).

The above 240 mg film coated tablets may be contained in a container closure system being a transparent polyvinylchloride (PVC)/polychlorotrifluoroethylene (PCTFE) film blister with an aluminum (Alu) push-through foil.

Example 4: In Vivo Bioequivalence Study

A pivotal clinical trial was conducted in 2 parts: Part 1 was to demonstrate the bioequivalence of the 240 mg film coated tablet of example 3.3 and the commercial 60 mg tablet under fasted conditions while Part 2 was to evaluate whether the administration of food affects the bioavailability of the 240 mg film coated tablet of example 3.3. In Part 1, Treatment B (240 mg film coated tablet of example 3.3) was concluded to be bioequivalent to Treatment A (commercial 60 mg tablet) under fasted conditions based on the 90% CI for geometric mean ratios of $C_{max}$ and $AUC_{0\text{-}72h}$ falling within the 80.00% to 125.00% criteria for bioequivalence as presented in Table 5.

TABLE 5

Statistical Results for apalutamide after a Single-Dose Oral Administration of 240 mg of apalutamide as Treatment B (240 mg film coated tablet of example 3.3, Test) and Treatment A (commercial 60 mg tablet, Reference), Under Fasted Conditions in Healthy Participants.

| PK Parameter | N | Treatment A (Reference) | Treatment B (Test) | Ratio of Geometric Means (%) | 90% CI (%) | Intra-subject CV (%) |
|---|---|---|---|---|---|---|
| $C_{max}$ (μg/mL) | 65 | 2.05 | 2.25 | 109.67 | 104.55-115.04 | 16.4 |
| $AUC_{0\text{-}72h}$ (h * μg/mL) | 63 | 57.7 | 59.3 | 102.71 | 100.78-104.68 | 6.4 |

Treatment A=Single dose of 4 tablets of commercial 60 mg apalutamide (Reference) Treatment B=Single dose of 1 tablet of 240 mg apalutamide (240 mg film coated tablet of example 3.3)

In Part 2, administration of a single tablet of 240 mg apalutamide (240 mg film coated tablet of example 3.3) under fed (Treatment D) and fasting (Treatment C) conditions resulted in comparable pharmacokinetics based on the 90% CI for geometric mean ratios of $C_{max}$ and $AUC_{0\text{-}72h}$ falling within the 80.00% to 125.00% criteria for bioequivalence as presented in Table 6.

TABLE 6

Statistical Results for apalutamide after Single Oral Administration of 240 mg of apalutamide to Healthy Participants under Fed and Fasting Conditions

| PK Parameter | N | Treatment C (Reference) | Treatment D (Test) | Ratio of Geometric Means (%) | 90% CI (%) | Intra-subject CV (%) |
|---|---|---|---|---|---|---|
| $C_{max}$ (μg/mL) | 20 | 2.36 | 2.15 | 90.96 | 83.06-99.61 | 16.7 |
| $AUC_{0\text{-}72h}$ (h * μg/mL) | 20 | 59.2 | 59.2 | 99.94 | 97.12-102.84 | 5.2 |

Treatment C=Single dose of 1 tablet of 240 mg apalutamide under Fasting Condition (240 mg film coated tablet of example 3.3)

Treatment D=Single dose of 1 tablet of 240 mg apalutamide under Fed Condition (240 mg film coated tablet of example 3.3)

Example 5: Robustness of the Tablet Composition of Example 3.2 and 3.3

The impact of variations in the levels of the disintegrant (croscarmellose sodium) and the lubricant (magnesium stearate) and the coating weight gain on the quality of the tablets has been studied.

The robustness of the 240 mg uncoated tablet of Example 3.2 towards excipients has been evaluated by varying the concentrations at tablet core level for:

- Croscarmellose sodium (disintegrant): 3.30% w/w (intragranular and extragranular) and 2.70% w/w (intragranular and extragranular) counterbalanced with silicified microcrystalline cellulose to maintain a core tablet weight of 1165 mg (FIG. 4)
- Magnesium stearate (lubricant): 0.55% w/w and 0.45% w/w counterbalanced with silicified microcrystalline cellulose to maintain a core tablet weight of 1165 mg (FIG. 5) The quantitative composition of the different core tablet batches are presented in Table 7.

TABLE 7

Composition of Core Tablet Batches with Variations in Croscarmellose Sodium and Magnesium Stearate

| | | Quantity per Tablet | | | | | | | | | |
|---|---|---|---|---|---|---|---|---|---|---|---|
| | | Target | | High CCS | | Low CCS | | High MS | | Low MS | |
| Component | Function | mg | w/w (%) | mg | w/w (%) | mg | w/w (%) | mg | w/w (%) | mg | w/w (%) |
| Intragranular phase | | | | | | | | | | | |
| 250 mg/g SDP | Active | 960.00 | 82.40 | 960.00 | 82.40 | 960.00 | 82.40 | 960.00 | 82.40 | 960.00 | 82.40 |
| Colloidal Anhydrous Silica | Glidant | 4.70 | 0.40 | 4.70 | 0.40 | 4.70 | 0.40 | 4.70 | 0.40 | 4.70 | 0.40 |

TABLE 7-continued

Composition of Core Tablet Batches with Variations in Croscarmellose Sodium and Magnesium Stearate

| | | Quantity per Tablet | | | | | | | | | |
|---|---|---|---|---|---|---|---|---|---|---|---|
| | | Target | | High CCS | | Low CCS | | High MS | | Low MS | |
| Component | Function | mg | w/w (%) | mg | w/w (%) | mg | w/w (%) | mg | w/w (%) | mg | w/w (%) |
| Croscarmellose Sodium | Disintegrant | 35.00 | 3.00 | 38.50 | 3.30 | 31.50 | 2.70 | 35.00 | 3.00 | 35.00 | 3.00 |
| Extragranular phase | | | | | | | | | | | |
| Silicified Microcrystalline Cellulose | Filler | 119.8 | 10.28 | 112.80 | 9.68 | 126.80 | 10.88 | 119.22 | 10.23 | 120.38 | 10.33 |
| Colloidal Anhydrous Silica | Glidant | 4.70 | 0.40 | 4.70 | 0.40 | 4.70 | 0.40 | 4.70 | 0.40 | 4.70 | 0.40 |
| Croscarmellose Sodium | Disintegrant | 35.00 | 3.00 | 38.50 | 3.30 | 31.50 | 2.70 | 35.00 | 3.00 | 35.00 | 3.00 |
| Magnesium Stearate | Lubricant | 5.80 | 0.50 | 5.80 | 0.50 | 5.80 | 0.50 | 6.38 | 0.55 | 5.22 | 0.45 |
| Core Tablet Weight | | 1165.00 | 100.00 | 1165.00 | 100.00 | 1165.00 | 100.00 | 1165.00 | 100.00 | 1165.00 | 100.00 |

CCS = Croscarmellose sodium
MS = Magnesium stearate
Target = 240 mg uncoated tablet of Example 3.2

Figure 4:
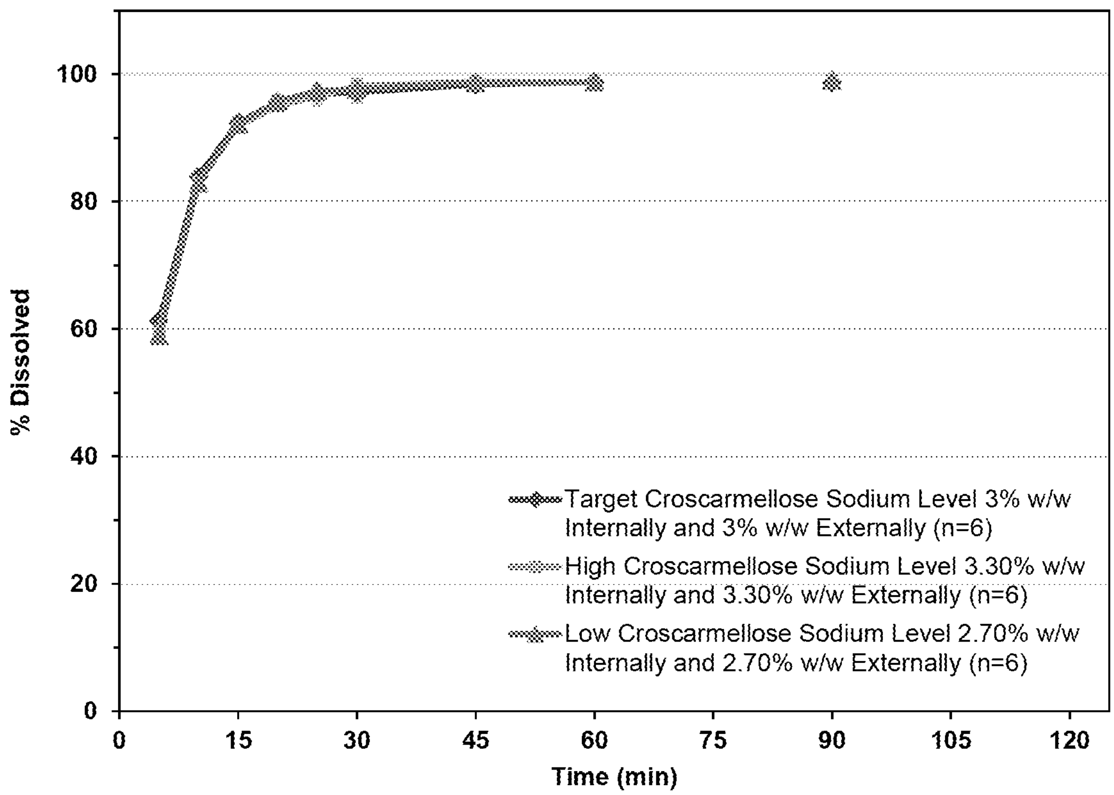
FIG. 4 depicts dissolution profiles of core tablets with varying croscarmellose sodium levels measured with a Paddle Apparatus at 75 rpm using 900 mL 0.05 M Sodium Phosphate Buffer of pH 4.5 at 37° C.
Figure 5:
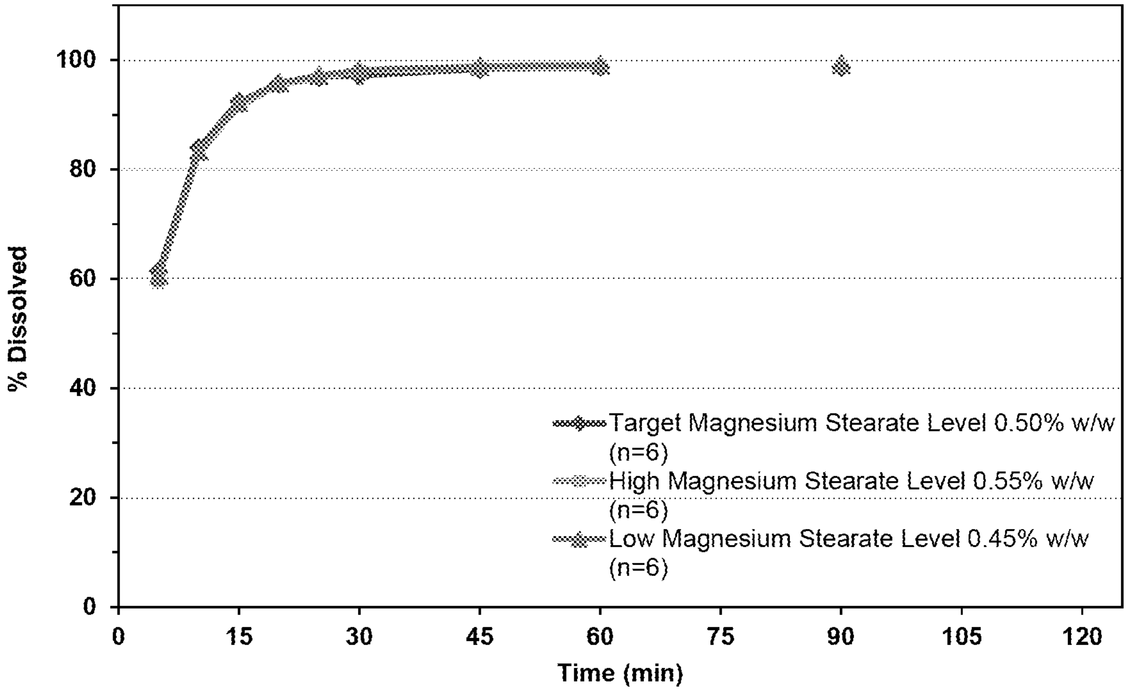
FIG. 5 depicts dissolution profiles of core tablets with varying magnesium stearate levels measured with a Paddle Apparatus at 75 rpm using 900 mL 0.05 M Sodium Phosphate Buffer of pH 4.5 at 37° C.

All boundary batches of core tablet (concepts High CCS, Low CCS, High MS, Low MS) were tested for dissolution and compared with the target batch. The excipient levels of croscarmellose sodium and magnesium stearate showed no influence on dissolution (FIG. 4 and FIG. 5).

Variations in Coating Weight Gain

Figure 6:
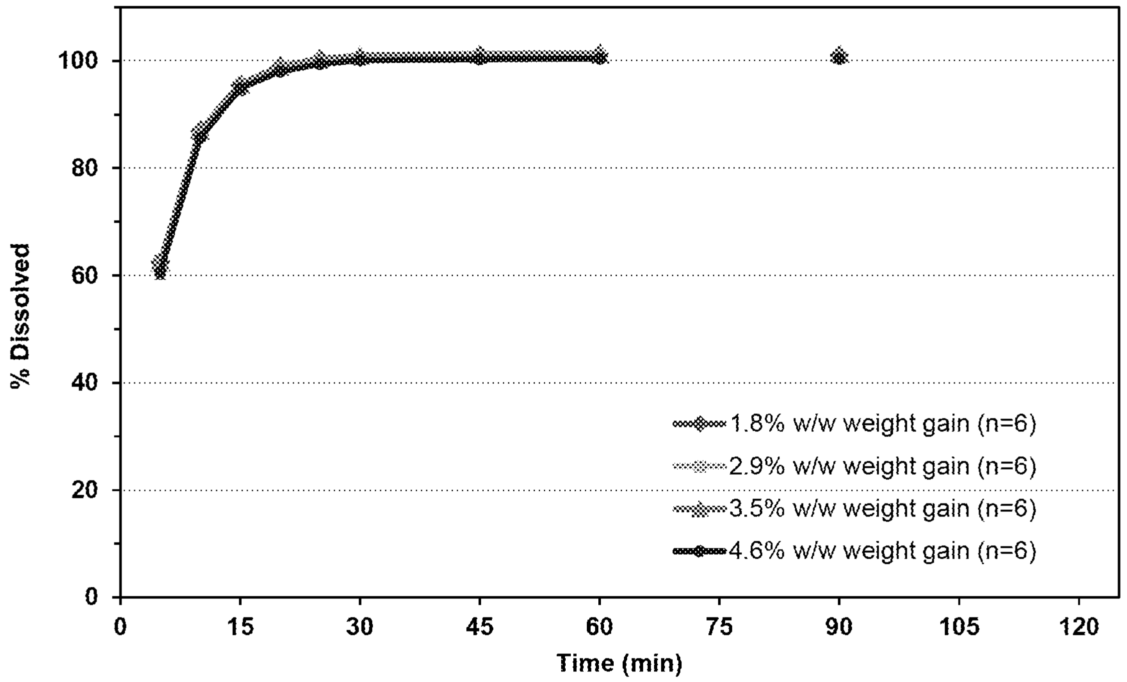
FIG. 6 depicts dissolution profiles of film-coated tablets with varying weight gain measured with a Paddle Apparatus at 75 rpm using 900 mL 0.05 M Sodium Phosphate Buffer of pH 4.5 at 37° C.

To study the impact of variation in the levels of coating weight gain on the appearance and the dissolution behavior of the finished drug product, 4 batches of 240 mg uncoated tablets of Example 3.2 have been prepared with 1.8, 2.9, 3.5, and 4.6% coating weight gain. All film-coated tablets passed for appearance. The variation in weight gain from 1.8% to 4.6% w/w showed no influence on dissolution (FIG. 6).

Overall, the 240 mg film coated tablet of Example 3.3 was found to be robust for variations in the excipients used in the drug product manufacturing process. Small variations in the composition do not adversely influence the quality of the drug product.

Example 6: Preparation of a Solid Dispersion of Apalutamide:HPMCAS LF 1:2

| | |
|---|---|
| Apalutamide | 333.33 mg |
| HPMCAS LF | 666.67 mg |
| Acetone [a] | 19000 mg |

[a] Removed during processing
(the reported amounts are for 1 g of SDP (spray dried product))

The acetone was transferred into a suitable container, and HPMCAS and apalutamide Form B were added. After mixing the ingredients using a suitable mixer, the mixture was spray dried using a suitable spray dryer, e.g. Buchi mini spray dryer with the following parameters: spray rate in the range from 6.2-6.7 gram/minute, outlet temperature in the range from 46° C. −49° C. and a condenser temperature in the range from −18° C. to −21° C.

The spray dried product (SDP) was dried in a suitable dryer, e.g. tray dryer using vacuum, nitrogen flow and a drying temperature of 40° C.

Example 7: Preparation of a Solid Dispersion of Apalutamide:HPMCAS LF 1:3 by Hot Melt Extrusion (HME)

| | |
|---|---|
| Apalutamide | 250 mg |
| HPMCAS LF | 750 mg |

(the reported amounts are for 1 g of HME product)

The HPMCAS and apalutamide Form B were blended in a suitable recipient using a suitable blender. Hot melt extrusion was performed in a Haake extruder, flush mode, maximum temperature 180° C., screw speed 50 rpm. The hot melt extrudate was collected and milled in a suitable mill. The milled hot melt extrudate was sieved using a suitable sieve (250 μm).

Example 8: Preparation of a Solid Dispersion of Apalutamide:HPMCAS LF 1:3 SDP

| | |
|---|---|
| Apalutamide | 250.0 mg |
| HPMCAS LF | 750.0 mg |
| Acetone [a] | 19000.0 mg |

[a] Removed during processing
(the reported amounts are for 1 g of SDP (spray dried product))

The acetone was transferred into a suitable container and HPMCAS LF and apalutamide Form B were added. After mixing the ingredients using a suitable mixer, the mixture was spray dried using a suitable spray dryer, e.g. Buchi mini spray dryer with the following parameters: spray rate in the range from 5.9-6.6 gram/minute, outlet temperature in the range from 46° C.-49° C. and a condenser temperature in the range from −15° C. to −21° C.

The spray dried product (SDP) was dried in a suitable dryer, e.g. tray dryer using vacuum, nitrogen flow and a drying temperature of 40° C.

Example 9: Compatibility of Liquid and Soft Food Vehicles

A number of liquids and soft foods have been selected as vehicles for the ease of administration of the apalutamide 240 mg Film Coated (FC) tablet (according to example 3.3).

TABLE 8

Liquids and Soft Foods Selected for Compatibility Studies

| Class | Class Representatives |
|---|---|
| Fruit Juice | Orange Juice |
| Tea | Green Tea |
| Soft Food | Yoghurt (drinkable) |
| | Apple Sauce |

The impact of each liquid and soft food on the quality of the apalutamide 240 mg FC tablets (according to example 3.3) was tested, evaluating appearance, assay and chromatographic purity. Apalutamide 240 mg FC tablets (according to example 3.3) readily disperse in water hence the tablet was dispersed in 10 mL water prior to mixing with 1 of the liquids or soft foods followed by analytical analyses. For each liquid and soft food, the preparation procedures and hold time conditions listed in Table 9 were evaluated.

TABLE 9

Preparation Procedures, and Hold Time Conditions Tested to Evaluate the Compatibility of each Liquid and Soft Food with Apalutamide 240 mg FC Tablets (according to example 3.3)

| Liquid or Soft Food | Dispersion | Amount of Liquid or Soft Food | Rinse | Hold Time Condition |
|---|---|---|---|---|
| Orange Juice | 10 mL water | 30 mL | 10 mL water | Ambient temperature, 1 hour |
| Green Tea | 10 mL water | 30 mL | 10 mL water | Ambient temperature, 1 hour |
| Youghurt | 10 mL water | 30 g | 15 mL water | Ambient temperature, 1 hour |
| Apple Sauce | 10 mL water | 30 g | 15 mL water | Ambient temperature, 1 hour |

TABLE 10

Dose Accuracy Test Results

| Food Vehicle | Appearance | Assay[a] (% w/w) |
|---|---|---|
| No Food vehicle[b] | Almost white | 100.6/100.9[c] |
| Orange Juice | | |
| Replicate 1 | Yellowish orange colour | 103.1 |
| Replicate 2 | Yellowish orange colour | 103.4 |
| Replicate 3 | Yellowish orange colour | 103.1 |
| Green Tea | | |
| Replicate 1 | Slightly yellowish white colour | 101.7 |
| Replicate 2 | Slightly yellowish white colour | 102.9 |
| Replicate 3 | Slightly yellowish white colour | 102.0 |

TABLE 10-continued

Dose Accuracy Test Results

| Food Vehicle | Appearance | Assay[a] (% w/w) |
|---|---|---|
| Yoghurt | | |
| Replicate 1 | White colour | 103.3 |
| Replicate 2 | White colour | 103.7 |
| Replicate 3 | White colour | 104.4 |
| Applesauce | | |
| Replicate 1 | Light yellowish brown colour | 101.6 |
| Replicate 2 | Light yellowish brown colour | 102.1 |
| Replicate 3 | Light yellowish brown colour | 100.9 |

[a]For dose accuracy study, the acceptance criterion for individual assay is ±15% of assay from the target assay value (acceptance criterion = 85.7% to 115.5%).

[b]Apalutamide 240 mg FC tablet dispersed in 10 mL water only, without using a food vehicle.

[c]Target assay value, without using food vehicle, for the experiment with applesauce was 100.9%.

TABLE 11

In-Use Stability Test Results- 1 Hour at Ambient Temperature

| Food Vehicle | Appearance | Assay (% w/w) | Specified Degradation Product | Unspecified Degradation Products | Total Degradation Products |
|---|---|---|---|---|---|
| No Food vehicle[a] | White colour | 100.6 | 0.06 | <0.05 | 0.06 |
| Orange Juice | | | | | |
| T0[b] | Yellowish orange colour | 103.1 | 0.07 | <0.05 | 0.07 |
| Replicate 1: 1 hour | Yellowish orange colour | 102.9 | 0.07 | <0.05 | 0.07 |
| Replicate 2: 1 hour | Yellowish orange colour | 102.8 | 0.07 | <0.05 | 0.07 |
| Green Tea | | | | | |
| T0[b] | Slightly yellowish white colour | 101.7 | 0.07 | <0.05 | 0.07 |
| Replicate 1: 1 hour | Slightly yellowish white colour | 103.2 | 0.07 | <0.05 | 0.07 |
| Replicate 2: 1 hour | Slightly yellowish white colour | 101.6 | 0.07 | <0.05 | 0.07 |
| Yoghurt | | | | | |
| T0[b] | White colour | 103.3 | 0.07 | <0.05 | 0.07 |
| Replicate 1: 1 hour | White colour | 102.6 | 0.07 | <0.05 | 0.07 |
| Replicate 2: 1 hour | White colour | 102.7 | 0.07 | <0.05 | 0.07 |
| Applesauce | | | | | |
| T0[b] | Light yellowish brown colour | 101.6 | 0.09 | <0.05 | 0.09 |
| Replicate 1: 1 hour | Light yellowish brown colour | 101.0 | 0.10 | <0.05 | 0.10 |
| Replicate 2: 1 hour | Light yellowish brown colour | 101.3 | 0.10 | <0.05 | 0.10 |

[a]Apalutamide 240 mg FC tablet dispersed in 10 mL water only, without using a food vehicle
[b]T0: Immediately tested after dispersion in water The compatibility results for all studies (Table 10 and Table 11), including the dose accuracy and in-use stability studies, of the apalutamide 240 mg FC tablets (according to example 3.3) with the selected food vehicles can be summarized as follows:

- No change in appearance was observed for any of the liquids and soft foods dispersions during the in-use hold time study.
- Assay results for the dispersed apalutamide 240 mg FC tablets (according to example 3.3) in food vehicles were between 100.9%-104.4% indicating that apalutamide is stable when using vehicles.
- No unspecified degradants were observed above the reporting limit (0.05%), demonstrating that there is no or adverse impact of the selected liquids or soft foods on the apalutamide 240 mg FC tablets (according to example 3.3), during in-use stability study.
- Based on these studies, the initial dispersion of the tablet can be conducted in 10 mL water. The resulting dispersion can then be administered in an appropriate amount of liquid or soft food. The administration container should be rinsed with an adequate amount of water to ensure the full dose is administered. Preparations in water, yoghurt, orange juice, green tea and applesauce are stable for at least 1 hour at ambient temperature.

In vitro dissolution was conducted to evaluate the release of apalutamide 240 mg FC tablets (according to example 3.3) when dispersed in liquid or soft food by analyzing the dissolution in the following medium: 0.5% sodium lauryl sulfate (SLS) in 0.05 M sodium phosphate buffer pH 4.5 at 37° C. The dissolution profiles of apalutamide 240 mg FC tablets (according to example 3.3) (n=12) dispersed in orange juice, green tea, yoghurt (drinkable) and apple sauce were compared to the profile of the reference (without using liquid or soft food) using the similarity factor f2. Although, the dissolution profile using yoghurt (drinkable) and green tea is observed to be slower compared to the dissolution profile without food vehicle, the f2-values are greater than 50 for all comparisons (see Table 11a). This demonstrates that the dissolution profiles of the 240 mg FC apalutamide formulation (according to example 3.3) with or without liquids or soft foods (orange juice, green tea, yoghurt or applesauce) are comparable.

TABLE 11a

Similarity Factors (f2) n = 12 - Test Results at Ambient Temperature

| Food Vehicle | Volume/ Weight of Vehicle | Observed f2 Value |
|---|---|---|
| Orange Juice | 30 mL | 67 |
| Green Tea | 30 mL | 65 |
| Yoghurt (drinkable) | 30 g | 60 |
| Apple Sauce | 30 g | 72 |

Acceptance criterion: Dissolution (n = 12) f2 value: 50 to 100

Example 10: Stability Tests

In the following tables stability results are provided for 240 mg FC apalutamide tablets (according to example 3.3) packed in HDPE bottle with desiccant (study 202432) or packed in PVC-PCTFE/Alu blisters (study 202435).

Water content by KF (Karl Fisher) was measured by coulometric Karl Fisher titration at 120° C.

Water content by NIR was measured by FT-NIR with a Spectrometer: Bruker MPA FT-NIR or equivalent.

Assay and chromatographic purity was measured by ultra-high performance liquid chromatographic (UHPLC) method with UV detection at 268 nm (column: Acquity BEH C18, 150 mm length×2.1 mm i.d., 1.7 μm particle size; column T=55° C.; flow rate: 0.45 mL/min; mobile phase: A: 10 mM $NH_4Ac$+0.1% TFA/Acetonitrile (90/10, v/v); B: Acetonitrile, gradient elution).

The dissolution test was performed using Paddle Apparatus (USP, Ph.Eur., JP.) at 75 rpm in 900 mL of 0.5% (w/v)

sodium lauryl sulfate in 0.05 M Sodium Phosphate buffer pH 4.5 at 37.0±0.5° C. The determination of the quantity of apalutamide present in the dissolution samples was measured with an isocratic ultra-high performance liquid chromatographic (UHPLC) method with UV detection at 242 nm (column: Acquity UPLC® CSH C18 1.7-μm particle size, 50×2.1 mm i.d.; column T=60±3° C.; flow rate: 0.6 mL/min; mobile phase: 50:50 (v:v) 0.1% trifluoracetic acid in water: acetonitrile).

Determination of solid state/crystallinity was measured by FT-NIR with a Spectrometer: Bruker MPA FT-NIR or equivalent.

Microbial purity was tested according to the method described in general chapters of the USP and Pharmacopeia, which are harmonized:

Specified organisms: PhEur 2.6.13/USP<60>

Microbial enumeration test: Ph.Eur 2.6.12/USP<61>

TABLE 12

Batch 4586783 (LDLS000) packed as 30 ct in 75 cc HDPE bottle with desiccant - Appearance, Water Content by KF and Water Content by NIR Results

| Parameter Storage Condition | Storage Time (Months) | Appearance[a] | Water Content by KF (% w/w) | Water Content by NIR (% w/w) |
|---|---|---|---|---|
| 5° C. | Initial | Pass | 1.6 | 1.8 |
| | 3 | Pass | 1.6 | 1.8 |
| | 12 | Pass | 1.7 | 1.7 |

TABLE 12-continued

Batch 4586783 (LDLS000) packed as 30 ct in 75 cc HDPE bottle with desiccant - Appearance, Water Content by KF and Water Content by NIR Results

| Parameter Storage Condition | Storage Time (Months) | Appearance[a] | Water Content by KF (% w/w) | Water Content by NIR (% w/w) |
|---|---|---|---|---|
| 25° C./60% RH | 3 | Pass | 1.7 | 1.9 |
| | 6 | Pass | 1.8 | 1.6 |
| | 9 | Pass | 1.9 | 1.7 |
| | 12 | Pass | 1.8 | 1.9 |
| 30° C./75% RH | 3 | Pass | 1.7 | 1.9 |
| | 6 | Pass | 1.8 | 1.7 |
| | 9 | Pass | 1.9 | 1.9 |
| | 12 | Pass | 2.0 | 2.0 |
| 40° C./75% RH | 3 | Pass | 1.8 | 1.9 |
| | 6 | Pass | 2.0 | 1.9 |
| 50° C. | 3 | Pass | 1.5 | 1.7 |
| Light ICH[b] (Unprotected) | | Pass | 1.7 | 1.6 |

[a]Bluish grey to grey oval film-coated tablet debossed, with "E240" on one side

[b]Light ICH: integrated near UV energy not less than 200 W · h/$m^2$, overall illumination not less than 1200 klux · hr

TABLE 13

Batch 4586783 (LDLS000) packed as 30 ct in 75 cc HDPE bottle with desiccant - Assay and Chromatographic Purity Results

| Parameter | | Assay (%) | Chromatographic Purity (%) | | |
|---|---|---|---|---|---|
| | | | Each Specified Degradation Product[a] | Any Unspecified | Total |
| Storage Condition | Storage Time (Months) | JNJ-56021927-AAA | JNJ-56142047-AAA | Degradation Product[a] | Degradation Products[b] |
| | Initial | 100.9 | 0.11 | <0.05 | 0.11 |
| 5° C. | 3 | 100.6 | 0.12 | <0.05 | 0.12 |
| | 12 | 100.8 | 0.12 | <0.05 | 0.12 |
| 25° C./60% RH | 3 | 101.1 | 0.12 | <0.05 | 0.12 |
| | 6 | 101.7 | 0.12 | <0.05 | 0.12 |
| | 9 | 101.3 | 0.12 | <0.05 | 0.12 |
| | 12 | 100.3 | 0.12 | <0.05 | 0.12 |
| 30° C./75% RH | 3 | 100.3 | 0.12 | <0.05 | 0.12 |
| | 6 | 101.4 | 0.12 | <0.05 | 0.12 |
| | 9 | 101.4 | 0.13 | <0.05 | 0.13 |
| | 12 | 100.6 | 0.12 | <0.05 | 0.12 |
| 40° C./75% RH | 3 | 101.3 | 0.13 | <0.05 | 0.13 |
| | 6 | 102.0 | 0.13 | <0.05 | 0.13 |
| 50° C. | 3 | 101.9 | 0.14 | <0.05 | 0.14 |
| Light ICH[c] (Unprotected) | | 101.0 | 0.13 | <0.05 | 0.13 |

[a]Specified and unspecified degradation product ≥0.05% (reporting threshold)

[b]Sum of all degradation products ≥0.05% (totals are calculated on unrounded results)

[c]Light ICH: integrated near UV energy not less than 200 W · h/$m^2$, overall illumination not less than 1200 klux · hr

TABLE 14

Batch 4586783 (LDLS000) packed as 30 ct in 75 cc HDPE bottle with desiccant - Dissolution Results

| Parameter | | Dissolution Mean (Min-Max) | | | | | | | | |
|---|---|---|---|---|---|---|---|---|---|---|
| Storage Condition | Storage Time (Months) | 5 min (%) | 10 min (%) | 15 min (%) | 20 min (%) | 25 min (%) | 30 min (%) | 45 min (%) | 60 min (%) | 90 min[a] (%) |
| | Initial[b] | 55(50-58) | 79(76-81) | 90(88-91) | 95(94-96) | 98(97-98) | 99(98-99) | 100(99-100) | 100(99-101) | 100(97-101) |
| 5° C. | 3 | 48(43-51) | 77(75-78) | 89(89-90) | 95(94-95) | 97(97-98) | 99(98-99) | 99(99-100) | 100(99-100) | 100(100-100) |
| | 12 | 49(48-50) | 77(76-78) | 89(89-90) | 95(94-95) | 97(97-98) | 99(98-99) | 100(100-101) | 100(100-101) | 101(100-101) |
| 25° C./60% RH | 3 | 49(48-50) | 78(77-78) | 89(88-90) | 95(93-95) | 97(96-98) | 98(96-99) | 99(97-100) | 99(97-100) | 99(98-100) |
| | 6 | 49(48-51) | 77(77-78) | 89(89-90) | 94(94-95) | 97(96-98) | 98(97-100) | 99(98-100) | 99(99-101) | 100(99-101) |
| | 9 | 49(47-50) | 77(76-77) | 89(88-89) | 94(94-95) | 96(96-97) | 98(97-98) | 99(98-99) | 99(99-100) | 99(99-100) |
| | 12 | 49(47-51) | 77(76-79) | 89(88-89) | 94(93-94) | 96(96-96) | 97(97-98) | 98(98-98) | 98(98-99) | 99(99-99) |
| 30° C./75% RH | 3 | 50(49-52) | 79(78-80) | 90(90-91) | 96(95-96) | 98(97-98) | 99(98-99) | 100(99-100) | 100(99-100) | 100(99-100) |
| | 6 | 52(50-56) | 79(78-81) | 91(90-91) | 96(95-96) | 98(97-98) | 99(98-100) | 100(99-101) | 100(99-100) | 100(99-101) |
| | 9 | 50(49-51) | 79(78-79) | 90(90-90) | 95(94-95) | 97(97-98) | 98(98-99) | 99(98-99) | 99(99-100) | 100(99-100) |
| | 12[d] | 52(49-56) | 80(79-82) | 91(90-92) | 95(94-96) | 97(96-98) | 98(97-99) | 99(98-100) | 99(97-100) | 99(98-101) |
| 40° C./75% RH | 3 | 52(50-55) | 81(79-81) | 92(91-92) | 96(96-97) | 98(98-99) | 99(98-100) | 100(99-100) | 100(99-101) | 100(99-101) |
| | 6 | 55(54-56) | 83(82-83) | 93(93-94) | 97(97-98) | 99(98-100) | 99(99-100) | 100(99-101) | 100(99-101) | 100(99-101) |
| 50° C. | 3 | 55(53-59) | 82(80-83) | 92(92-93) | 97(96-98) | 99(98-100) | 99(99-101) | 100(99-101) | 100(100-102) | 100(100-101) |
| Light ICH[c] (Unprotected) | | 53(51-56) | 80(79-81) | 91(90-91) | 95(95-95) | 97(96-97) | 98(97-98) | 98(97-98) | 98(98-99) | 98(98-99) |

[a]Samples at infinity time point (at 90 minutes) were collected after increasing paddle rotation speed to 250 rpm (maximum speed allowed by the instrument) for 30 minutes, after the last profile time point (i.e., 60 minutes)
[b]Initial results were taken from release data
[c]Light ICH: integrated near UV energy not less than 200 W · h/$m^2$, overall illumination not less than 1200 klux · hr
[d]Avenge of 12 units results are reported

TABLE 15

Batch 4586783 (LDLS000) packed as 30 ct in 75 cc HDPE bottle with desiccant - Solid state by NIR Results

| Parameter | | Solid State |
|---|---|---|
| Storage Condition | Storage Time (Months) | by NIR[a] (%) |
| | Initial | <5.0 |
| 5° C. | 3 | <5.0 |
| | 12 | <5.0 |
| 25° C./60% RH | 3 | <5.0 |
| | 6 | <5.0 |
| | 9 | <5.0 |
| | 12 | <5.0 |
| 30° C./75% RH | 3 | <5.0 |
| | 6 | <5.0 |
| | 9 | c5.0 |
| | 12 | <5.0 |
| 40° C./75% RH | 3 | <5.0 |
| | 6 | <5.0 |
| 50° C. | 3 | <5.0 |
| Light ICH[b] (Unprotected) | | <5.0 |

TABLE 15-continued

Batch 4586783 (LDLS000) packed as 30 ct in 75 cc HDPE bottle with desiccant - Solid state by NIR Results

[a]Reporting threshold for solid state by NIR is 5.0%
[b]Light ICH: integrated near UV energy not less than 200 W · h/$m^2$, overall illumination not less than 1200 klux · hr

TABLE 16

Batch 4586783 (LDLS000) packed as 30 ct in 75 cc HDPE bottle with desiccant - Microbial Purity Results

| Parameter Storage Condition | Storage Time (Months) | Total Aerobic Microbial Count (TAMC) (CFU/g) | Total Combined Yeasts and Molds Count (TYMC) (CFU/g) | Specified Micro-organisms: *Escherichia coli* (Absent/g) |
|---|---|---|---|---|
| | Initial | <100 | <50 | Pass |
| 25° C./60% RH | 12 | <100 | <50 | Pass |
| 30° C./75% RH | 12 | <100 | <50 | Pass |

Batch 4586783 (LDLS000) stability results for 240 mg FC apalutamide tablets (according to example 3.3) packed in PVC-PCTFE/Alu blisters.

TABLE 17

Batch 4586783 (LDLS000) packed as 14 ct in PVC-PCTFE/Alu blisters - Appearance, Water Content by KF and Water Content by NIR Results

| Parameter: Storage Condition | Storage Time (Months) | Appearance' | Water Content by KF (% w/w) | Water Content by NIR (% w/w) |
|---|---|---|---|---|
| | Initial | Pass | 2.1 | 1.9 |
| 5° C. | 3 | Pass | 1.8 | 1.8 |
| | 12 | Pass | 1.9 | 1.9 |

TABLE 17-continued

Batch 4586783 (LDLS000) packed as 14 ct in PVC-PCTFE/Alu blisters - Appearance, Water Content by KF and Water Content by NIR Results

| Parameter: Storage Condition | Storage Time (Months) | Appearance' | Water Content by KF (% w/w) | Water Content by NIR (% w/w) |
|---|---|---|---|---|
| 25° C./60% RH | 3 | Pass | 1.9 | 1.9 |
| | 6 | Pass | 2.0 | 2.0 |
| | 9 | Pass | 2.1 | 2.0 |
| | 12 | Pass | 2.3 | 2.2 |
| 30° C./75% RH | 3 | Pass | 2.0 | 2.0 |
| | 6 | Pass | 2.2 | 2.2 |
| | 9 | Pass | 2.4 | 2,4 |
| | 12 | Pass | 2.6 | 2.5 |
| 40° C./75% RH | 3 | Pass | 2.3 | 2.4 |
| | 6 | Pass | 2.7 | 2.8 |
| 50° C. | 3 | Pass | 1.5 | 1.6 |
| Light ICH[b,c] (Unprotected) | | Pass | 1.7 | 1.6 |

[a]Bluish grey to grey oval film-coated tablet debossed, with "E240" on one side

[b]Light ICH: integrated near UV energy not less than 200 W · h/$m^2$, overall illumination not less than 1200 klux · hr

[c]Light ICH (Unprotected) condition results taken from Study-202432 - Batch 4586783 (LDLS000) of bottle packaging

TABLE 18

Batch 4586783 (LDLS000) packed as 14 ct in PVC-PCTFE/Alu blisters - Assay and Chromatographic Purity Results

| Parameter: Storage Condition | Storage Time (Months) | Assay (%) JNJ-56021927-AAA | Chromatographic Purity (%): Each Specified Degradation Product[a] JNJ-56142047-AAA | Chromatographic Purity (%): Any Unspecified Degradation Product[a] | Total Degradation Products[b] |
|---|---|---|---|---|---|
| | Initial | 100.9 | 0.11 | <0.05 | 0.11 |
| 5° C. | 3 | 99.4 | 0.12 | <0.05 | 0.12 |
| | 12 | 100.9 | 0.11 | <0.05 | 0.11 |
| 25° C./60% RH | 3 | 99.4 | 0.12 | <0.05 | 0.12 |
| | 6 | 100.8 | 0.13 | <0.05 | 0.13 |
| | 9 | 100.9 | 0.12 | <0.05 | 0.12 |
| | 12 | 101.4 | 0.13 | <0.05 | 0.13 |
| 30° C./75% RH | 3 | 99.5 | 0.12 | <0.05 | 0.12 |
| | 6 | 100.9 | 0.13 | <0.05 | 0.13 |
| | 9 | 101.3 | 0.13 | <0.05 | 0.13 |
| | 12 | 100.6 | 0.12 | <0.05 | 0.12 |
| 40° C./75% RH | 3 | 99.3 | 0.13 | <0.05 | 0.13 |
| | 6 | 101.2 | 0.14 | <0.05 | 0.14 |
| 50° C. | 3 | 99.1 | 0.14 | <0.05 | 0.14 |
| Light ICH[c,d] (Unprotected) | | 101.0 | 0.13 | <0.05 | 0.13 |

[a]Specified and unspecified degradation product ≥0.05% (reporting threshold)

[b]Sum of all degradation products >0.05% (totals are calculated on unrounded results)

[c]Light ICH: integrated near UV energy not less than 200 W · h/$m^2$, overall illumination not less than 1200 klux · hr

[d]Light ICH (Unprotected) condition results taken from Study-202432 - Batch 4586783 (LDLS000) of bottle packaging

TABLE 19

Batch 4586783 (LDLS000) packed as 14 ct in PVC-PCTFE/ Alu blisters - Dissolution Results

| Parameter | | Dissolution | | | | | | | | |
|---|---|---|---|---|---|---|---|---|---|---|
| | Storage | Mean (Min-Max) | | | | | | | | |
| Storage Condition | Time (Months) | 5 min (%) | 10 min (%) | 15 min (%) | 20 min (%) | 25 min (%) | 30 min (%) | 45 min (%) | 60 min (%) | 90 min[a] (%) |
| | Initial[b] | 55(50-58) | 79(76-81) | 90(88-91) | 95(94-96) | 98(97-98) | 99(98-99) | 100(99-100) | 100(99-101) | 100(97-101) |
| 5° C. | 3 | 51(49-54) | 79(78-80) | 90(90-91) | 96(95-96) | 98(97-98) | 99(98-99) | 99(99-100) | 100(99-100) | 100(100-100) |
| | 12 | 48(46-50) | 77(76-78) | 89(88-90) | 94(94-95) | 97(96-97) | 98(98-98) | 99(98-99) | 99(99-99) | 100(99-100) |
| 25° C./60% RH | 3 | 52(50-53) | 80(79-81) | 91(91-92) | 96(96-97) | 98(97-99) | 99(98-100) | 100(99-101) | 100(99-101) | 100(100-101) |
| | 6 | 53(50-55) | 81(79-82) | 91(90-92) | 95(94-96) | 97(96-98) | 98(97-99) | 99(98-100) | 99(98-100) | 100(99-101) |
| | 9 | 54(51-56) | 81(79-82) | 91(91-92) | 95(95-96) | 97(97-98) | 98(98-99) | 99(98-99) | 99(98-99) | 100(99-100) |
| | 12 | 52(50-55) | 81(80-82) | 92(92-92) | 96(96-97) | 98(98-99) | 99(99-100) | 100(99-101) | 100(99-101) | 101(100-101) |
| 30° C./75% RH | 3 | 53(51-54) | 81(80-81) | 92(91-93) | 96(96-97) | 98(98-99) | 99(98-100) | 100(99-100) | 99(99-100) | 99(99-100) |
| | 6 | 55(53-57) | 82(82-83) | 92(92-93) | 96(96-96) | 98(97-98) | 99(98-99) | 99(99-100) | 100(98-101) | 100(100-101) |
| | 9 | 54(51-57) | 82(81-83) | 92(92-94 | 96(96-97) | 98(97-100) | 98(98-100) | 99(98-101) | 99(98-101) | 99(98-101) |
| | 12 | 55(52-57) | 83(82-83) | 92(90-93) | 96(96-97) | 97(96-98) | 98(97-99) | 99(98-100) | 99(98-100) | 99(99-100) |
| 40° C./75% RH | 3 | 55(54-56) | 83(82-84) | 93(93-94) | 97(97-97) | 98(98-99) | 99(99-100) | 99(99-100) | 99(99-100) | 99(99-100) |
| | 6 | 55(51-58) | 83(81-84) | 93(92-93) | 97(96-97) | 98(98-99) | 99(98-100) | 99(99-100) | 99(99-99) | 99(99-100) |
| 50° C. | 3 | 54(53-55) | 81(80-83) | 92(91-93 | 96(96-97) | 98(97-99) | 99(98-100) | 100(99-100) | 100(99-100) | 100(99-100) |
| Light ICH[c,d] (Unprotected) | | 53(51-56) | 80(79-81) | 91(90-91) | 95(95-95) | 97(96-97) | 98(97-98) | 98(97-98) | 98(98-99) | 98(98-99) |

[a]Samples at infinity time point (at 90 minutes) were collected after increasing paddle rotation speed to 250 rpm (maximum speed allowed by the instrument) for 30 minutes, after the last profile time point (i.e., 60 minutes)

[b]Initial results were taken from release data of respective DP batch

[c]Light ICH: integrated near UV energy not less than 200 W · h/m$^2$, overall illumination not less than 1200 klux · hr

[d]Light ICH (Unprotected) condition results taken from Study-202432-Batch 4586783 (LDLS000) of bottle packaging

TABLE 20

Batch 4586783 (LDLS000) packed as 14 ct in PVC-PCTFE/ Alu blisters -Solid state by NIR Results

| Parameter | | Solid State |
|---|---|---|
| Storage Condition | Storage Time (Months) | by NIR[a] (%) |
| | Initial | <5.0 |
| 5° C. | 3 | <5.0 |
| | 12 | <5.0 |
| 25° C./60% RH | 3 | <5.0 |
| | 6 | <5.0 |
| | 9 | <5.0 |
| | 12 | <5.0 |
| 30° C./75% RH | 3 | <5.0 |
| | 6 | <5.0 |
| | 9 | c5.0 |
| | 12 | <5.0 |

TABLE 20-continued

Batch 4586783 (LDLS000) packed as 14 ct in PVC-PCTFE/ Alu blisters -Solid state by NIR Results

| Parameter | | Solid State |
|---|---|---|
| Storage Condition | Storage Time (Months) | by NIR[a] (%) |
| 40° C./75% RH | 3 | <5.0 |
| | 6 | <5.0 |
| 50° C. | 3 | <5.0 |
| Light ICH[b,c] (Unprotected) | | <5.0 |

[a]Reporting threshold for solid state by NIR is 5.0%

[b]Light ICH: integrated near UV energy not less than 200 W · h/m$^2$, overall illumination not less than 1200 klux · hr

[c]Light ICH (Unprotected) condition results taken from Study-202432 - Batch 4586783 (LDLS000) of bottle packaging

TABLE 21

Batch 4586783 (LDLS000) packed as 14 ct in PVC-PCTFE/Alu blisters - Microbial Purity Results

| Parameter | | Total Aerobic Microbial Count | Total Combined Yeast and Molds Count | Specified Micro-organisms: |
|---|---|---|---|---|
| Storage Condition | Storage Time (Months) | (TAMC) (CFU/g) | (TYMC) (CFU/g) | *E. coil* (Absent/g) |
| | Initial | <100 | <50 | Pass |
| 25° C. 160% RH | 12 | <100 | <50 | Pass |
| 30° C./75% RH | 12 | <100 | <50 | Pass |

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the present description.

Example 11: FDA Approval Letter

The FDA sent the following approval letter on 17 Feb. 2023 for ERLEADA to include 240 mg apalutamide approved drug product, which will be the reference listed drug for this drug product.

U.S. FOOD & DRUG
ADMINISTRATION

NDA 210951/S-011

SUPPLEMENT APPROVAL

Janssen Biotech, Inc.
Attention: Elise
Mazzola, MPH

Associate Director, Global Regulatory
Affairs 920 U.S. Highway 202, P.O.
Box 300
Raritan, NJ
08869

Dear Ms. Mazzola:

Please refer to your supplemental new drug application (sNDA) dated and received on October 28, 2022, and your amendments, submitted under section 505(b) of the Federal Food, Drug, and Cosmetic Act (FDCA) for Erleada (apalutamide) tablet.

This Prior Approval sNDA provides for the addition of Erleada 240 mg tablet formulation to Section 2- Dosage and Administration, Section 3- Dosage Forms and Strengths, Section 11- Description, Section 16- How Supplied/Storage and Handling and corresponding revisions to Section 17- Patient Counseling Information, Patient Package Insert (PPI), carton and container labeling and the creation of an Instructions for Use (IFU).

APPROVAL & LABELING

We have completed our review of this application. It is approved, effective on the date of this letter, for use as recommended in the enclosed agreed-upon labeling.

CONTENT OF LABELING

As soon as possible, but no later than 14 days from the date of this letter, submit the content of labeling [21 CFR 314.50(l)] in structured product labeling (SPL) format using the FDA automated drug registration and listing system (eLIST), as described at FDA.gov.[1] Content of labeling must be identical to the enclosed labeling text for the Prescribing Information, Patient Package Insert, and Instructions for Use, with the addition of any labeling changes in pending "Changes Being Effected" (CBE) supplements, as well as annual reportable changes not included in the enclosed labeling.

Information on submitting SPL files using eList may be found in the guidance for industry *SPL Standard for Content of Labeling Technical Qs and As*.[2]

NDA 210951/S-011
Page 2

The SPL will be accessible from publicly available labeling repositories.

Also within 14 days, amend all pending supplemental applications that include labeling changes for this NDA, including CBE supplements for which the FDA has not yet issued an action letter, with the content of labeling [21 CFR 314.50(l)(1)(i)] in Microsoft Word format, that includes the changes approved in this supplemental application, as well as annual reportable changes. To facilitate review of your submission(s), provide a highlighted or marked-up copy that shows all changes, as 1 www.fda.gov/ForIndustry/DataStandards/StructuredProductLabeling/default.htm 2 We update guidances periodically. For the most recent version of a guidance, check the FDA Guidance Documents Database www.fda.gov/RegulatoryInformation/Guidances/default.htm.

well as a clean Microsoft Word version. The marked-up copy should provide appropriate annotations, including supplement number(s) and annual report date(s).

CARTON AND CONTAINER LABELING

Submit final printed carton and container labeling that are identical to the carton and container labeling submitted on February 9, 2023, as soon as they are available, but no more than 30 days after they are printed. Please submit these labeling electronically according to the guidance for industry *Providing Regulatory Submissions in Electronic Format — Certain Human Pharmaceutical Product Applications and Related Submissions Using the eCTD Specifications*. For administrative purposes, designate this submission "Final Printed Carton and Container Labeling for approved NDA 210951/S-011." Approval of this submission by the FDA is not required before the labeling is used.

REQUIRED PEDIATRIC ASSESSMENTS

Under the Pediatric Research Equity Act (PREA) (21 U.S.C. 355c), all applications for new active ingredients (which includes new salts and new fixed combinations), new indications, new dosage forms, new dosing regimens, or new routes of administration are required to contain an assessment of the safety and effectiveness of the product for the claimed indication in pediatric patients unless this requirement is waived, deferred, or inapplicable.

Because none of these criteria apply to your application, you are exempt from this requirement.

PROMOTIONAL MATERIALS

You may request advisory comments on proposed introductory advertising and promotional labeling. For information about submitting promotional materials, see the final guidance for industry *Providing Regulatory Submissions in Electronic and*

*Non-Electronic Format-Promotional Labeling and Advertising Materials for Human Prescription Drugs.*[3]

NDA 210951/S-011

Page 3

You must submit final promotional materials and Prescribing Information, accompanied by a Form FDA 2253, at the time of initial dissemination or publication [21 CFR 314.81(b)(3)(i)]. Form FDA 2253 is available at FDA.gov.[4] Information and Instructions for completing the form can be found at FDA.gov.[5]

All promotional materials that include representations about your drug product must be promptly revised to be consistent with the labeling changes approved in this supplement, including any new safety- related information [21 CFR 314.70(a)(4)]. The revisions in your promotional materials should include prominent disclosure of the important new safety-related information that appears in the revised labeling. Within 7 days of receipt of this letter, submit your statement of intent to comply with 21 CFR 314.70(a)(4).

PATENT LISTING REQUIREMENTS

Pursuant to 21 CFR 314.53(d)(2) and 314.70(f), certain changes to an approved NDA submitted in a supplement require you to submit patent information for listing in the Orange Book upon approval of the supplement. You must submit the patent information required by 21 CFR 314.53(d)(2)(i)(A) through (C) and 314.53(d)(2)(ii)(A) and (C), as applicable, to the FDA on Form FDA 3542 within 30 days after the date of approval of the supplement for the patent information to be timely filed (see 21 CFR 314.53(c)(2)(ii)). You also must ensure that any changes to your approved NDA that require the submission of a request to remove patent

---

3 For the most recent version of a guidance, check the FDA guidance web page at www.fda.gov/media/128163/download.

4 www.fda.gov/downloads/AboutFDA/ReportsManualsForms/Forms/UCM083570.pdf 5 www.fda.gov/downloads/AboutFDA/ReportsManualsForms/Forms/UCM375154.pdf information from the Orange Book are submitted to the FDA at the time of approval of the supplement pursuant to 21 CFR 314.53(d)(2)(ii)(B) and 314.53(f)(2)(iv).

REPORTING REQUIREMENTS

We remind you that you must comply with reporting requirements for an approved NDA (21 CFR 314.80 and 314.81).

If you have any questions, contact Anna Lananh Nguyen, PharmD, Regulatory Project Manager, via email at Lananh.Nguyen@fda.hhs.gov.

Sincerely,

{See appended electronic signature page}

Laleh Amiri- Kordestani, MD
Director

Division of Oncology 1

Office of Oncologic Diseases

Center for Drug Evaluation and Research

ENCLOSURE(S):

- Content of Labeling
  - Prescribing Information
  - Patient Package Insert
  - Instructions for Use
- Carton and Container Labeling This is a representation of an electronic record that was signed electronically. Following this are manifestations of any and all electronic signatures for this electronic record.

/s/

DANIEL L
SUZMAN
02/17/2023
12:07:25 PM
Signing on behalf of Laleh Amiri Kordestani Example 11: Final FDA Approved Drug Product Label The FDA approved the following drug product label on 17 February 2023 for ERLEADA to include 240 mg apalutamide approved drug product, which will be the reference listed drug for this drug product.

HIGHLIGHTS OF PRESCRIBING INFORMATION

These highlights do not include all the information needed to use ERLEADA safely and effectively. See full prescribing information for ERLEADA.

ERLEADA® (apalutamide) tablets, for oral use

Initial U.S. Approval – 2018

---RECENT MAJOR CHANGES---

| | |
|---|---|
| Dosage and Administration, Recommended Dosage (2.1) | 02/2023 |
| Dosage and Administration, Dosage Modification (2.2) | 11/2022 |
| Dosage and Administration, Alternate Methods of Administration (2.3) | 02/2023 |
| Warnings and Precautions, Severe Cutaneous Adverse Reactions (SCARs) (5.5) | 11/2022 |

---INDICATIONS AND USAGE---

ERLEADA is an androgen receptor inhibitor indicated for the treatment of patients with

- metastatic castration-sensitive prostate cancer. (1)
- non-metastatic castration-resistant prostate cancer. (1)

--- DOSAGE AND ADMINISTRATION ---

ERLEADA 240 mg administered orally once daily. Swallow tablets whole. ERLEADA can be taken with or without food. (2.1, 2.3)

Patients should also receive a gonadotropin-releasing hormone (GnRH) analog concurrently or should have had bilateral orchiectomy. (2.1)

--- DOSAGE FORMS AND STRENGTHS ---

Tablets: 240 mg (3)

Tablets: 60 mg (3)

---CONTRAINDICATIONS---

None. (4)

--- WARNINGS AND PRECAUTIONS ---

- Cerebrovascular and ischemic cardiovascular events occurred in patients receiving ERLEADA. Monitor for signs and symptoms of cerebrovascular disorders and ischemic heart disease. Optimize management of cardiovascular risk factors. (5.1).
- Fractures occurred in patients receiving ERLEADA. Evaluate patients for fracture risk and treat patients with bone-targeted agents according to established guidelines. (5.2)
- Falls occurred in patients receiving ERLEADA with increased incidence in the elderly. Evaluate patients for fall risk. (5.3)
- Seizure occurred in 0.4% of patients receiving ERLEADA. Permanently discontinue ERLEADA in patients who develop a seizure during treatment. (5.4)
- Severe Cutaneous Adverse Reactions (SCARs), including Stevens-Johnson syndrome/toxic epidermal necrolysis (SJS/TEN) and drug reaction with eosinophilia and systemic symptoms (DRESS), occurred in patients treated with ERLEADA. Interrupt ERLEADA if signs or symptoms of SCARs develop. Permanently discontinue if SCARs are confirmed. (5.5)
- Embryo-Fetal Toxicity: ERLEADA can cause fetal harm. Advise males with female partners of reproductive potential to use effective contraception. (5.6, 8.1, 8.3)

------------------------------ADVERSE REACTIONS------------------------------

The most common adverse reactions (≥10%) are fatigue, arthralgia, rash, decreased appetite, fall, weight decreased, hypertension, hot flush, diarrhea, and fracture. (6.1)

To report SUSPECTED ADVERSE REACTIONS, contact Janssen Products, LP at 1-800-526-7736 (1-800-JANSSEN) or FDA at 1-800-FDA-1088 or *www.fda.gov/medwatch.*

------------------------------DRUG INTERACTIONS------------------------------

Concomitant use with medications that are sensitive substrates of CYP3A4, CYP2C19, CYP2C9, UGT, P-gp, BCRP, or OATP1B1 may result in loss of activity of these medications. (7.2)

See 17 for PATIENT COUNSELING INFORMATION and FDA-approved patient labeling.

Revised: 02/2023

FULL PRESCRIBING INFORMATION: CONTENTS*

1 INDICATIONS AND USAGE
2 DOSAGE AND ADMINISTRATION
  2.1 Recommended Dosage
  2.2 Dosage Modification
  2.3 Alternate Methods of Administration
3 DOSAGE FORMS AND STRENGTHS
4 CONTRAINDICATIONS
5 WARNINGS AND PRECAUTIONS
  5.1 Cerebrovascular and Ischemic Cardiovascular Events
  5.2 Fractures
  5.3 Falls
  5.4 Seizure
  5.5 Severe Cutaneous Adverse Reactions
  5.6 Embryo-Fetal Toxicity
6 ADVERSE REACTIONS
  6.1 Clinical Trial Experience
  6.2 Post-Marketing Experience
7 DRUG INTERACTIONS
  7.1 Effect of Other Drugs on ERLEADA
  7.2 Effect of ERLEADA on Other Drugs
8 USE IN SPECIFIC POPULATIONS
  8.1 Pregnancy
  8.2 Lactation
  8.3 Females and Males of Reproductive Potential
  8.4 Pediatric Use
  8.5 Geriatric Use
10 OVERDOSAGE
11 DESCRIPTION
12 CLINICAL PHARMACOLOGY
  12.1 Mechanism of Action
  12.2 Pharmacodynamics
  12.3 Pharmacokinetics
13 NONCLINICAL TOXICOLOGY
  13.1 Carcinogenesis, Mutagenesis, Impairment of Fertility
14 CLINICAL STUDIES
16 HOW SUPPLIED/STORAGE AND HANDLING
17 PATIENT COUNSELING INFORMATION

*Sections or subsections omitted from the full prescribing information are not listed.

FULL PRESCRIBING INFORMATION

1 *INDICATIONS AND USAGE*

ERLEADA is indicated for the treatment of patients with

- Metastatic castration-sensitive prostate cancer (mCSPC)
- Non-metastatic castration-resistant prostate cancer (nmCRPC)

2 *DOSAGE AND ADMINISTRATION*

2.1 Recommended Dosage

The recommended dose of ERLEADA is 240 mg administered orally once daily. Swallow the tablets whole. Do not crush or split tablets. ERLEADA can be taken with or without food.

Patients should also receive a gonadotropin-releasing hormone (GnRH) analog concurrently or should have had a bilateral orchiectomy.

2.2 Dosage Modification

If Grade 3 or greater adverse reactions, or other intolerable adverse reactions occur, withhold ERLEADA. Consider permanent discontinuation of ERLEADA for Grade 3 or 4 cerebrovascular and ischemic cardiovascular events *[see Warnings and Precautions (5.1)]*. Permanently discontinue ERLEADA for confirmed SCARs or for other Grade 4 skin reactions *[see Warnings and Precautions (5.5) and Adverse Reactions (6.1)]*. For other adverse reactions, when symptoms improve to less than or equal to Grade 1 or original grade, resume ERLEADA at the same dose or a reduced dose (180 mg or 120 mg), if warranted.

2.3 Alternate Methods of Administration

Disperse 240 mg Tablet in Water and Administer with Orange Juice, Applesauce, or Additional Water For patients who cannot swallow the tablet whole, the recommended dose of one ERLEADA 240 mg tablet can be dispersed in non-carbonated water and then administered with either orange juice, applesauce, or additional water as follows:

1. Place the whole ERLEADA 240 mg tablet in a cup. Do not crush or split the tablet.

2. Add about 2 teaspoons (10 mL) of non-carbonated water to make sure that the tablet is completely immersed in water.

3. Wait 2 minutes until the tablet is broken up and spread out, then stir the mixture.

4. Add 2 tablespoons (30 mL) of either orange juice, applesauce, or additional water and stir the mixture.

5. Swallow the mixture immediately.

6. Rinse the cup with enough water to make sure the whole dose is taken and drink it immediately.

Do not store ERLEADA that is mixed with non-carbonated water, orange juice, or applesauce for later use.

Administer 240 mg Tablet Through a Feeding Tube

ERLEADA 240 mg tablet can be administered through a feeding tube 8 French or greater as follows:

1. Place one 240 mg tablet in the barrel of the syringe (use at least a 20 mL syringe) and draw up 10 mL of non-carbonated water into the syringe.

2. Wait 10 minutes and then shake vigorously to disperse contents completely.

3. Administer immediately through the feeding tube.

4. Refill the syringe with non-carbonated water and administer. Repeat until no tablet residue is left in the syringe or feeding tube.

Administer 60 mg Tablets with Applesauce

For patients who have difficulty swallowing tablets whole, the recommended dose of ERLEADA 60 mg tablets may be mixed in applesauce.

1. Mix whole ERLEADA 60 mg tablets in 4 ounces (120 mL) of applesauce by stirring. Do not crush or split the tablets.

2. Wait 15 minutes, stir the mixture.

3. Wait another 15 minutes, stir the mixture until tablets are dispersed (well mixed with no chunks remaining).

4. Using a spoon, swallow the mixture right away.

5. Rinse the container with 2 ounces (60 mL) of water and immediately drink the contents. Repeat the rinse with 2 ounces (60 mL) of water a second time to ensure the whole dose is taken.

Consume the mixture within one hour of preparation. Do not store ERLEADA that is mixed with applesauce.

3 DOSAGE FORMS AND STRENGTHS

Tablets:

- 240 mg: bluish grey to grey, oval, film-coated and debossed with “E240” on one side.
- 60 mg: slightly yellowish to greyish green, oblong, film-coated and debossed with “AR 60” on one side.

4 CONTRAINDICATIONS

None.

5 WARNINGS AND PRECAUTIONS 5.1 <u>Cerebrovascular and Ischemic Cardiovascular Events</u>

Cerebrovascular and ischemic cardiovascular events, including events leading to death, occurred in patients receiving ERLEADA. Monitor for signs and symptoms of ischemic heart disease and cerebrovascular disorders. Optimize management of cardiovascular risk factors, such as hypertension, diabetes, or dyslipidemia. Consider discontinuation of ERLEADA for Grade 3 and 4 events.

In a randomized study (SPARTAN) of patients with nmCRPC, ischemic cardiovascular events occurred in 3.7% of patients treated with ERLEADA and 2% of patients treated with placebo. In a randomized study (TITAN) in patients with mCSPC, ischemic cardiovascular events occurred in 4.4% of patients treated with ERLEADA and 1.5% of patients treated with placebo. Across the SPARTAN and TITAN studies, 4 patients (0.3%) treated with ERLEADA, and 2 patients (0.2%) treated with placebo died from an ischemic cardiovascular event.

In the SPARTAN study, cerebrovascular events occurred in 2.5% of patients treated with ERLEADA and 1% of patients treated with placebo *[see Adverse Reactions (6.1)]*. In the TITAN study, cerebrovascular events occurred in 1.9% of patients treated with ERLEADA and 2.1% of patients treated with placebo. Across the SPARTAN and TITAN studies, 3 patients (0.2%) treated with ERLEADA, and 2 patients (0.2%) treated with placebo died from a cerebrovascular event.

Patients with history of unstable angina, myocardial infarction, congestive heart failure, stroke, or transient ischemic attack within six months of randomization were excluded from the SPARTAN and TITAN studies.

5.2 Fractures

Fractures occurred in patients receiving ERLEADA. Evaluate patients for fracture risk. Monitor and manage patients at risk for fractures according to established treatment guidelines and consider use of bone-targeted agents.

In a randomized study (SPARTAN) of patients with non-metastatic castration-resistant prostate cancer, fractures occurred in 12% of patients treated with ERLEADA and in 7% of patients treated with placebo. Grade 3-4 fractures occurred in 2.7% of patients treated with ERLEADA and in 0.8% of patients treated with placebo. The median time to onset of fracture was 314 days (range: 20 to 953 days) for patients treated with ERLEADA. Routine bone density assessment and treatment of osteoporosis with bone-targeted agents were not performed in the SPARTAN study.

In a randomized study (TITAN) of patients with metastatic castration-sensitive prostate cancer, fractures occurred in 9% of patients treated with ERLEADA and in 6% of patients treated with placebo. Grade 3-4 fractures were similar in both arms at 1.5%. The median time to onset of fracture was 56 days (range: 2 to 111 days) for patients treated with ERLEADA. Routine bone density assessment and treatment of osteoporosis with bone-targeted agents were not performed in the TITAN study.

5.3 Falls

Falls occurred in patients receiving ERLEADA with increased frequency in the elderly *[see Use in Specific Populations (8.5)]*. Evaluate patients for fall risk.

In a randomized study (SPARTAN), falls occurred in 16% of patients treated with ERLEADA compared to 9% of patients treated with placebo. Falls were not associated with loss of consciousness or seizure.

5.4 Seizure

Seizure occurred in patients receiving ERLEADA. Permanently discontinue ERLEADA in patients who develop a seizure during treatment. It is unknown whether anti-epileptic medications will prevent seizures with ERLEADA. Advise patients of the risk of developing a seizure while receiving ERLEADA and of engaging in any activity where sudden loss of consciousness could cause harm to themselves or others.

In two randomized studies (SPARTAN and TITAN), five patients (0.4%) treated with ERLEADA and one patient treated with placebo (0.1%) experienced a seizure. Seizure occurred from 159 to 650 days after initiation of ERLEADA. Patients with a history of seizure, predisposing factors for seizure, or receiving drugs known to decrease the seizure threshold or to induce seizure were excluded. There is no clinical experience in re-administering ERLEADA to patients who experienced a seizure.

5.5 Severe Cutaneous Adverse Reactions

Fatal and life threatening cases of severe cutaneous adverse reactions (SCARs), including Stevens-Johnson syndrome/toxic epidermal necrolysis (SJS/TEN), and drug reaction with eosinophilia and systemic symptoms (DRESS), occurred in patients receiving ERLEADA *[see Adverse Reactions (6.2)].*

Monitor patients for the development of SCARs. Advise patients of the signs and symptoms of SCARs (e.g., a prodrome of fever, flu-like symptoms, mucosal lesions, progressive skin rash, or lymphadenopathy).

If a SCAR is suspected, interrupt ERLEADA until the etiology of the reaction has been determined. Consultation with a dermatologist is recommended. If a SCAR is confirmed, or for other grade 4 skin reactions, permanently discontinue ERLEADA *[see Dosage and Administration (2.2) and Adverse Reactions (6.1)].*

5.6 Embryo-Fetal Toxicity

The safety and efficacy of ERLEADA have not been established in females. Based on findings from animals and its mechanism of action, ERLEADA can cause fetal harm and loss of pregnancy when administered to a pregnant female. In an animal reproduction study, oral administration of apalutamide to pregnant rats during and after organogenesis resulted in fetal abnormalities and embryo-fetal lethality at maternal exposures ≥ 2 times the human clinical exposure (AUC) at the recommended dose. Advise males with female partners of reproductive potential to use effective contraception during treatment and for 3 months after the last dose of ERLEADA *[see Use in Specific Populations (8.1, 8.3) and Clinical Pharmacology (12.1)].*

6 *ADVERSE REACTIONS*

The following are discussed in more detail in other sections of the labeling:

- Cerebrovascular and Ischemic Cardiovascular Events *[see Warnings and Precautions (5.1)].*
- Fractures *[see Warnings and Precautions (5.2)].*
- Falls *[see Warnings and Precautions (5.3)].*
- Seizure *[see Warnings and Precautions (5.4)].*

- Severe Cutaneous Adverse Reactions (SCARs) *[see Warnings and Precautions (5.5)]*.

6.1 Clinical Trial Experience

Because clinical trials are conducted under widely varying conditions, adverse reaction rates observed in the clinical trials of a drug cannot be directly compared to rates in the clinical trials of another drug and may not reflect the rates observed in practice.

The most common adverse reactions (≥ 10%) that occurred more frequently in the ERLEADA-treated patients (≥ 2% over placebo) from the randomized placebo-controlled clinical trials (TITAN and SPARTAN) were fatigue, arthralgia, rash, decreased appetite, fall, weight decreased, hypertension, hot flush, diarrhea, and fracture.

Metastatic Castration-sensitive Prostate Cancer (mCSPC)

TITAN, a randomized (1:1), double-blind, placebo-controlled, multi-center clinical study, enrolled patients who had mCSPC. In this study, patients received either ERLEADA at a dose of 240 mg daily or placebo. All patients in the TITAN study received a concomitant gonadotropin-releasing hormone (GnRH) analog or had prior bilateral orchiectomy. The median duration of exposure was 20 months (range: 0 to 34 months) in patients who received ERLEADA and 18 months (range: 0.1 to 34 months) in patients who received placebo.

Ten patients (1.9%) who were treated with ERLEADA died from adverse reactions. The reasons for death were ischemic cardiovascular events (n=3), acute kidney injury (n=2), cardio-respiratory arrest (n=1), sudden cardiac death (n=1), respiratory failure (n=1), cerebrovascular accident (n=1), and large intestinal ulcer perforation (n=1). ERLEADA was discontinued due to adverse reactions in 8% of patients, most commonly from rash (2.3%). Adverse reactions leading to dose interruption or reduction of ERLEADA occurred in 23% of patients; the most frequent (>1%) were rash, fatigue, and hypertension. Serious adverse reactions occurred in 20% of ERLEADA-treated patients and 20% in patients receiving placebo.

Table 1 shows adverse reactions occurring in ≥10% on the ERLEADA arm in TITAN that occurred with a ≥2% absolute increase in frequency compared to placebo. Table 2 shows laboratory abnormalities that occurred in ≥15% of patients, and more frequently (>5%) in the ERLEADA arm compared to placebo.

Additional adverse reactions of interest occurring in 2%, but less than 10% of patients treated with ERLEADA included diarrhea (9% versus 6% on placebo), muscle spasm (3.1% versus 1.9% on placebo), dysgeusia (3.2% versus 0.6% on placebo), and hypothyroidism (3.6% versus 0.6% on placebo).

Non-metastatic Castration-resistant Prostate Cancer (nmCRPC)

SPARTAN, a randomized (2:1), double-blind, placebo-controlled, multi-center clinical study, enrolled patients who had nmCRPC. In this study, patients received either ERLEADA at a dose of 240 mg daily or a placebo. All patients in the SPARTAN study received a concomitant gonadotropin-releasing hormone (GnRH) analog or had a bilateral orchiectomy. The median duration of exposure was 33 months (range: 0.1 to 75 months) in patients who received ERLEADA and 11 months (range: 0.1 to 37 months) in patients who received placebo.

Twenty-four patients (3%) who were treated with ERLEADA died from adverse reactions. The reasons for death with ≥ 2 patients included infection (n=7), myocardial infarction (n=3), cerebrovascular event (n=2), and unknown reason (n=3). ERLEADA was discontinued due to adverse reactions in 11% of patients, most commonly from rash (3.2%). Adverse reactions leading to dose interruption or reduction of ERLEADA occurred in 33% of patients; the most common (>1%) were rash, diarrhea, fatigue, nausea, vomiting, hypertension, and hematuria. Serious adverse reactions occurred in 25% of ERLEADA-treated patients and 23% in patients receiving placebo. The most frequent serious adverse reactions (>2%) were fracture (3.4%) in the ERLEADA arm and urinary retention (3.8%) in the placebo arm.

Table 3 shows adverse reactions occurring in ≥10% on the ERLEADA arm in SPARTAN that occurred with a ≥2% absolute increase in frequency compared to placebo. Table 4 shows laboratory abnormalities that occurred in ≥15% of patients, and more frequently (>5%) in the ERLEADA arm compared to placebo.

Additional clinically significant adverse reactions occurring in 2% or more of patients treated with ERLEADA included hypothyroidism (8% versus 2% on placebo), pruritus (6% versus 1.5% on placebo), and heart failure (2.2% versus 1% on placebo).

Rash

In the combined data of two randomized, placebo-controlled clinical studies, SPARTAN and TITAN, rash associated with ERLEADA was most commonly described as macular or maculo-papular. Adverse reactions of rash were reported for 26% of patients treated with ERLEADA versus 8% of patients treated with placebo. Grade 3 rashes (defined as covering > 30% body surface area [BSA]) were reported with ERLEADA treatment (6%) versus placebo (0.5%).

The onset of rash occurred at a median of 83 days of ERLEADA treatment. Rash resolved in 78% of patients within a median of 78 days from onset of rash. Rash was commonly managed with oral antihistamines, topical corticosteroids, and 19% of patients received systemic corticosteroids. Dose reduction or dose interruption occurred in 14% and 28% of patients, respectively. Of the patients who had dose interruption, 59% experienced recurrence of rash upon reintroduction of ERLEADA.

Hypothyroidism

In the combined data of two randomized, placebo-controlled clinical studies, SPARTAN and TITAN, hypothyroidism was reported for 8% of patients treated with ERLEADA and 1.5% of patients treated with placebo based on assessments of thyroid-stimulating hormone (TSH) every 4 months. Elevated TSH occurred in 25% of patients treated with ERLEADA and 7% of patients treated with placebo. The median onset was at the first scheduled assessment. There were no Grade 3 or 4 adverse reactions. Thyroid replacement therapy was initiated in 4.9% of patients treated with ERLEADA. Thyroid replacement therapy, when clinically indicated, should be initiated or dose-adjusted *[see Drug Interactions (7.2)]*.

6.2 Post-Marketing Experience

The following additional adverse reactions have been identified during post-approval use of ERLEADA. Because these reactions are reported voluntarily from a population of uncertain size, it is not always possible to reliably estimate the frequency or establish a causal relationship to drug exposure.

*Respiratory, Thoracic and Mediastinal Disorders*: interstitial lung disease

*Skin and Subcutaneous Tissue Disorders*: Stevens-Johnson syndrome/toxic epidermal necrolysis (SJS/TEN) and drug reaction with eosinophilia and systemic symptoms (DRESS).

7 DRUG INTERACTIONS

7.1 Effect of Other Drugs on ERLEADA

Strong CYP2C8 or CYP3A4 Inhibitors

Co-administration of a strong CYP2C8 or CYP3A4 inhibitor is predicted to increase the steady-state exposure of the active moieties (sum of unbound apalutamide plus the potency-adjusted unbound N-desmethyl-apalutamide). No initial dose adjustment is necessary however, reduce the ERLEADA dose based on tolerability *[see Dosage and Administration (2.2)]*. Mild or moderate inhibitors of CYP2C8 or CYP3A4 are not expected to affect the exposure of apalutamide.

7.2 Effect of ERLEADA on Other Drugs

CYP3A4, CYP2C9, CYP2C19 and UGT Substrates

ERLEADA is a strong inducer of CYP3A4 and CYP2C19, and a weak inducer of CYP2C9 in humans. Concomitant use of ERLEADA with medications that are primarily metabolized by CYP3A4, CYP2C19, or CYP2C9 can result in lower exposure to these medications. Substitution for these medications is recommended when possible or evaluate for loss of activity if medication is continued. Concomitant administration of ERLEADA with medications that are substrates of UDP-glucuronosyl transferase (UGT) can result in decreased exposure. Use caution if substrates of UGT must be co-administered with ERLEADA and evaluate for loss of activity *[see Clinical Pharmacology (12.3)]*.

P-gp, BCRP or OATP1B1 Substrates

Apalutamide was shown to be a weak inducer of P-glycoprotein (P-gp), breast cancer resistance protein (BCRP), and organic anion transporting polypeptide 1B1 (OATP1B1) clinically. At steady-state, apalutamide reduced the plasma exposure to fexofenadine (a P-gp substrate) and rosuvastatin (a BCRP/OATP1B1 substrate). Concomitant use of ERLEADA with medications that are substrates of P-gp, BCRP, or OATP1B1 can result in lower exposure of these medications. Use caution if substrates of P-gp, BCRP or OATP1B1 must be co-administered with ERLEADA and evaluate for loss of activity if medication is continued *[see Clinical Pharmacology (12.3)]*.

8 USE IN SPECIFIC POPULATIONS

8.1 Pregnancy

Risk Summary

The safety and efficacy of ERLEADA have not been established in females. Based on findings from animals and its mechanism of action, ERLEADA can cause fetal harm and loss of pregnancy when administered to a pregnant female *[see Clinical Pharmacology (12.1)]*. There are no available data on ERLEADA use in pregnant women to inform a drug-associated risk. In an animal reproduction study, oral administration of apalutamide to pregnant rats during and after organogenesis resulted in fetal abnormalities and embryo-fetal lethality at maternal exposures ≥ 2 times the human clinical exposure (AUC) at the recommended dose *(see Data)*.

Data

Animal Data

In a pilot embryo-fetal developmental toxicity study in rats, apalutamide caused developmental toxicity when administered at oral doses of 25, 50 or 100 mg/kg/day throughout and after the period of organogenesis (gestational days 6-20). Findings included embryo-fetal lethality (resorptions) at doses ≥50 mg/kg/day, decreased fetal anogenital distance, misshapen pituitary gland, and skeletal variations (unossified phalanges, supernumerary short thoracolumbar rib(s), and small, incomplete ossification, and/or misshapen hyoid bone) at ≥25 mg/kg/day. A dose of 100 mg/kg/day caused maternal toxicity. The doses tested in rats resulted in systemic exposures (AUC) approximately 2, 4 and 6 times, respectively, the AUC in patients.

8.2 Lactation

Risk Summary

The safety and efficacy of ERLEADA have not been established in females. There are no data on the presence of apalutamide or its metabolites in human milk, the effect on the breastfed child, or the effect on milk production.

8.3 Females and Males of Reproductive Potential

Contraception

Males

Based on the mechanism of action and findings in an animal reproduction study, advise male patients with female partners of reproductive potential to use effective contraception during treatment and for 3 months after the last dose of ERLEADA *[see Use in Specific Populations (8.1)]*.

Infertility

Males

Based on animal studies, ERLEADA may impair fertility in males of reproductive potential *[see Nonclinical Toxicology (13.1)]*.

8.4 Pediatric Use

Safety and effectiveness of ERLEADA in pediatric patients have not been established.

8.5 Geriatric Use

Of the 1327 patients who received ERLEADA in clinical studies, 19% of patients were less than 65 years, 41% of patients were 65 years to 74 years, and 40% were 75 years and over.

No overall differences in effectiveness were observed between older and younger patients.

Of patients treated with ERLEADA (n=1073), Grade 3-4 adverse reactions occurred in 39% of patients younger than 65 years, 41% of patients 65-74 years, and 49% of patients 75 years or older. Falls in patients receiving ERLEADA with androgen deprivation therapy was elevated in the elderly, occurring in 8% of patients younger than 65 years, 10% of patients 65-74 years, and 19% of patients 75 years or older.

10 OVERDOSAGE

There is no known specific antidote for apalutamide overdose. In the event of an overdose, stop ERLEADA, undertake general supportive measures until clinical toxicity has been diminished or resolved.

11 DESCRIPTION

Apalutamide, the active ingredient of ERLEADA, is an androgen receptor inhibitor. Each ERLEADA tablet contains either 60 mg or 240 mg of apalutamide. The chemical name is (4-[7-(6-Cyano-5-trifluoromethylpyridin-3-yl)-8-oxo-6-thioxo-5,7-diazaspiro[3.4]oct-5-yl]-2-fluoro-N-methylbenzamide). Apalutamide is a white to slightly yellow powder. Apalutamide is practically insoluble in aqueous media over a wide range of pH values.

The molecular weight is 477.44 and molecular formula is $C_{21}H_{15}F_4N_5O_2S$. The structural formula is:

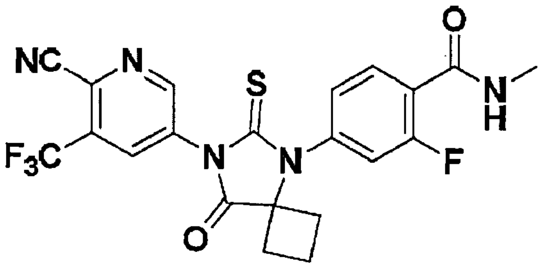

ERLEADA® (apalutamide) tablets are available in 240 mg tablets and 60 mg tablets with the following inactive ingredients:

- 240 mg film-coated tablets: colloidal anhydrous silica, croscarmellose sodium, hydroxypropyl methylcellulose-acetate succinate, silicified microcrystalline cellulose, and magnesium stearate. The coating contains glyceryl monocaprylocaprate, iron oxide black, polyvinyl alcohol, talc, titanium dioxide, and vinyl alcohol grafted copolymer.

- 60 mg film-coated tablets: colloidal anhydrous silica, croscarmellose sodium, hydroxypropyl methylcellulose-acetate succinate, magnesium stearate, microcrystalline cellulose, and silicified microcrystalline cellulose. The coating contains iron oxide black, iron oxide yellow, polyethylene glycol, polyvinyl alcohol, talc, and titanium dioxide.

12 CLINICAL PHARMACOLOGY

12.1 Mechanism of Action

Apalutamide is an Androgen Receptor (AR) inhibitor that binds directly to the ligand-binding domain of the AR. Apalutamide inhibits AR nuclear translocation, inhibits DNA binding, and impedes AR-mediated transcription. A major metabolite, N-desmethyl apalutamide, is a less potent inhibitor of AR, and exhibited one-third the activity of apalutamide in an *in vitro* transcriptional reporter assay. Apalutamide administration caused decreased tumor cell proliferation and increased apoptosis leading to decreased tumor volume in mouse xenograft models of prostate cancer.

12.2 Pharmacodynamics

Cardiac Electrophysiology

The effect of apalutamide 240 mg once daily on the QTc interval was assessed in an open-label, uncontrolled, multi-center, single-arm dedicated QT study in 45 patients with CRPC. The maximum mean QTcF change from baseline was 12.4 ms (2-sided 90% upper CI: 16.0 ms). An exposure-QT analysis suggested a concentration-dependent increase in QTcF for apalutamide and its active metabolite.

12.3 Pharmacokinetics

Apalutamide pharmacokinetic parameters are presented as the mean [standard deviation (SD)] unless otherwise specified. Apalutamide $C_{max}$ and area under the concentration curve (AUC) increased proportionally following repeated once-daily dosing of 30 to 480 mg (0.125 to 2 times the recommended dosage). Following administration of the recommended dosage, apalutamide steady-state was achieved after 4 weeks and the mean accumulation ratio was approximately 5-fold. Apalutamide $C_{max}$ was 6.0 mcg/mL (1.7) and AUC was 100 mcg·h/mL (32) at steady-state. Daily fluctuations in apalutamide plasma concentrations were low, with mean peak-to-trough ratio of 1.63. An increase in apparent clearance (CL/F) was observed with repeat dosing, likely due to induction of apalutamide's own metabolism. The auto-induction effect likely reached its maximum at the recommended dosage because exposure of apalutamide across the dose range of 30 to 480 mg is dose-proportional.

The major active metabolite N-desmethyl apalutamide $C_{max}$ was 5.9 mcg/mL (1.0) and AUC was 124 mcg·h/mL (23) at steady-state after the recommended dosage. N-desmethyl apalutamide was characterized by a flat concentration-time profile at steady-state with a mean peak-to-trough ratio of 1.27. Mean AUC metabolite/parent drug ratio for N-desmethyl apalutamide following repeat-dose administration was 1.3. Based on systemic exposure, relative potency, and pharmacokinetic properties, N-desmethyl apalutamide likely contributed to the clinical activity of apalutamide.

Absorption

Mean absolute oral bioavailability was approximately 100%. Median time to achieve peak plasma concentration ($t_{max}$) was 2 hours (range: 1 to 5 hours).

Oral administration of four 60 mg apalutamide tablets dispersed in applesauce resulted in no clinically relevant changes in $C_{max}$ and AUC when compared to administration of four intact 60 mg tablets under fasting condition.

Effect of Food

Administration of apalutamide to healthy subjects under fasting conditions and with a high-fat meal (approximately 500 to 600 fat calories, 250 carbohydrate calories, and 150 protein calories) resulted in no clinically relevant changes in $C_{max}$ and AUC. Median time to reach $t_{max}$ was delayed approximately 2 hours with food.

Distribution

The mean apparent volume of distribution at steady-state of apalutamide was approximately 276 L.

Apalutamide was 96% and N-desmethyl apalutamide was 95% bound to plasma proteins with no concentration dependency.

Elimination

The CL/F of apalutamide was 1.3 L/h after single dosing and increased to 2.0 L/h at steady-state after once-daily dosing likely due to CYP3A4 auto-induction. The mean effective half-life for apalutamide in patients was approximately 3 days at steady-state.

Metabolism

Metabolism is the main route of elimination of apalutamide. Apalutamide is primarily metabolized by CYP2C8 and CYP3A4 to form active metabolite, N-desmethyl apalutamide. The contribution of CYP2C8 and CYP3A4 in the metabolism of apalutamide is estimated to be 58% and 13% following single dose but changes to 40% and 37%, respectively at steady-state.

Apalutamide represented 45% and N-desmethyl apalutamide represented 44% of the total AUC following a single oral administration of radiolabeled apalutamide 240 mg.

Excretion

Up to 70 days following a single oral administration of radiolabeled apalutamide, 65% of the dose was recovered in urine (1.2% of dose as unchanged apalutamide and 2.7% as N-desmethyl apalutamide) and 24% was recovered in feces (1.5% of dose as unchanged apalutamide and 2% as N-desmethyl apalutamide).

Specific Populations

No clinically significant differences in the pharmacokinetics of apalutamide or N-desmethyl apalutamide were observed based on age (18-94 years), race (Black, non-Japanese Asian, Japanese), mild to moderate (eGFR 30-89 mL/min/1.73 $m^2$, estimated by the modification of diet in renal disease [MDRD] equation) renal impairment, or mild (Child-Pugh A) to moderate (Child-Pugh B) hepatic impairment.

The effect of severe renal impairment or end stage renal disease (eGFR ≤29 mL/min/1.73 $m^2$, MDRD) or severe hepatic impairment (Child-Pugh C) on apalutamide pharmacokinetics is unknown.

Drug Interactions

Effect of Other Drugs on ERLEADA

Strong CYP2C8 inhibitors

Apalutamide $C_{max}$ decreased by 21% while AUC increased by 68% following co-administration of ERLEADA as a 240 mg single dose with gemfibrozil (a strong CYP2C8 inhibitor). Gemfibrozil is predicted to increase the steady-state apalutamide $C_{max}$ by 32% and AUC by 44%. For the active moieties (sum of unbound apalutamide plus the potency-adjusted unbound N- desmethyl apalutamide), the predicted steady-state $C_{max}$ increased by 19% and AUC by 23%.

Strong CYP3A4 inhibitors

Apalutamide $C_{max}$ decreased by 22% while AUC was similar following co-administration of ERLEADA as a 240 mg single dose with itraconazole (a strong CYP3A4 inhibitor). Ketoconazole (a strong CYP3A4 inhibitor) is predicted to increase the single-dose apalutamide AUC by 24% but have no impact on $C_{max}$. Ketoconazole is predicted to increase the steady-state apalutamide $C_{max}$ by 38% and AUC by 51%. For the active moieties, the predicted steady-state $C_{max}$ increased by 23% and AUC by 28%.

CYP3A4/CYP2C8 inducers

Rifampin (a strong CYP3A4 and moderate CYP2C8 inducer) is predicted to decrease the steady- state apalutamide $C_{max}$ by 25% and AUC by 34%. For the active moieties, the predicted steady- state $C_{max}$ decreased by 15% and AUC by 19%.

Acid lowering agents

Apalutamide is not ionizable under relevant physiological pH condition, therefore acid lowering agents (e.g., proton pump inhibitor, $H_2$-receptor antagonist, antacid) are not expected to affect the solubility and bioavailability of apalutamide.

Drugs affecting transporters

In vitro, apalutamide and N-desmethyl apalutamide are substrates for P-gp but not BCRP, OATP1B1, and OATP1B3. Because apalutamide is completely absorbed after oral administration, P-gp does not limit the absorption of apalutamide and therefore, inhibition or induction of P-gp is not expected to affect the bioavailability of apalutamide.

Effect of ERLEADA on Other Drugs

CYP substrates

*In vitro* studies showed that apalutamide and N-desmethyl apalutamide are moderate to strong CYP3A4 and CYP2B6 inducers, are moderate inhibitors of CYP2B6 and CYP2C8, and weak inhibitors of CYP2C9, CYP2C19, and CYP3A4. Apalutamide and N-desmethyl apalutamide do not affect CYP1A2 and CYP2D6 at therapeutically relevant concentrations.

Co-administration of ERLEADA with single oral doses of sensitive CYP substrates resulted in a 92% decrease in the AUC of midazolam (a CYP3A4 substrate), 85% decrease in the AUC of omeprazole (a CYP2C19 substrate), and 46% decrease in the AUC of S-warfarin (a CYP2C9 substrate). ERLEADA did not cause clinically significant changes in exposure to a CYP2C8 substrate.

P-gp, BCRP and OATP1B1 substrates

Co-administration of ERLEADA with single oral doses of transporter substrates resulted in a 30% decrease in the AUC of fexofenadine (a P-gp substrate) and 41% decrease in the AUC of rosuvastatin (a BCRP/OATP1B1 substrate) but had no impact on $C_{max}$.

UGT substrates

Apalutamide may induce UGT. Concomitant administration of ERLEADA with medications that are substrates of UGT may result in lower exposure to these medications.

OCT2, OAT1, OAT3 and MATEs substrates

*In vitro*, apalutamide and N-desmethyl apalutamide inhibit organic cation transporter 2 (OCT2), organic anion transporter 3 (OAT3) and multidrug and toxin extrusions (MATEs), and do not inhibit organic anion transporter 1. Apalutamide is not predicted to cause clinically significant changes in exposure to an OAT3 substrate.

GnRH analog

In mCSPC subjects receiving leuprolide acetate (a GnRH analog) co-administered with apalutamide, PK data indicated that apalutamide had no apparent effect on the steady-state exposure of leuprolide.

13 NONCLINICAL TOXICOLOGY

13.1 Carcinogenesis, Mutagenesis, Impairment of Fertility

In a 2-year carcinogenicity study in male rats, apalutamide was administered by oral gavage at doses of 5, 15 and 50 mg/kg/day. Apalutamide increased the incidence of Leydig interstitial cell adenoma in the testes at doses ≥ 5 mg/kg/day (0.2 times the human exposure based on AUC). The findings in the testes are considered to be related to the pharmacological activity of apalutamide. Rats are regarded as more sensitive than humans to developing interstitial cell tumors in the testes. Oral administration of apalutamide to male rasH2 transgenic mice for 6 months did not result in increased incidence of neoplasms at doses up to 30 mg/kg/day.

Apalutamide did not induce mutations in the bacterial reverse mutation (Ames) assay and was not genotoxic in either *in vitro* chromosome aberration assay or the *in vivo* rat bone marrow micronucleus assay or the *in vivo* rat Comet assay.

In repeat-dose toxicity studies in male rats (up to 26 weeks) and dogs (up to 39 weeks), atrophy of the prostate gland and seminal vesicles, aspermia/hypospermia, tubular degeneration and/or hyperplasia or hypertrophy of the interstitial cells in the reproductive system were observed at ≥ 25 mg/kg/day in rats (1.4 times the human exposure based on AUC) and ≥ 2.5 mg/kg/day in dogs (0.9 times the human exposure based on AUC).

In a fertility study in male rats, a decrease in sperm concentration and motility, increased abnormal sperm morphology, lower copulation and fertility rates (upon pairing with untreated females) along with reduced weights of the secondary sex glands and epididymis were observed following 4 weeks of dosing at ≥ 25 mg/kg/day (0.8 times the human exposure based on AUC). A reduced number of live fetuses due to increased pre- and/or post-implantation loss was observed following 4 weeks of 150 mg/kg/day administration (5.7 times the human exposure based on AUC). Effects on male rats were reversible after 8 weeks from the last apalutamide administration.

14 CLINICAL STUDIES

The efficacy and safety of ERLEADA was established in two randomized placebo-controlled clinical trials.

<u>TITAN (NCT02489318): Metastatic Castration-sensitive Prostate Cancer (mCSPC)</u>

TITAN was a randomized, double-blind, placebo-controlled, multinational, clinical trial in which 1052 patients with mCSPC were randomized (1:1) to receive either ERLEADA orally at a dose of 240 mg once daily (N=525) or placebo once daily (N=527). All patients in the TITAN trial received concomitant GnRH analog or had prior bilateral orchiectomy. Patients were stratified by Gleason score at diagnosis, prior docetaxel use, and region of the world. Patients with both high- and low-volume mCSPC were eligible for the study. High volume of disease was defined as metastases involving the viscera with 1 bone lesion or the presence of 4 or more bone lesions, at least 1 of which must be in a bony structure beyond the vertebral column and pelvic bones.

The following patient demographics and baseline disease characteristics were balanced between the treatment arms. The median age was 68 years (range 43-94) and 23% of patients were 75 years of age or older. The racial distribution was 68% Caucasian, 22% Asian, and 2% Black. Sixty-three percent (63%) of patients had high-volume disease and 37% had low-volume disease. Sixteen percent (16%) of patients had prior surgery, radiotherapy of the prostate or both. A majority of patients had a Gleason score of 8 or higher (67%). Sixty-eight percent (68%) of patients received prior treatment with an anti-androgen (bicalutamide, flutamide, or nilutamide).

All patients except one in the placebo group, had an Eastern Cooperative Oncology Group Performance Status (ECOG PS) score of 0 or 1 at study entry.

The major efficacy outcome measures of the study were overall survival (OS) and radiographic progression-free survival (rPFS). Radiographic progression-free survival was based on investigator assessment and was defined as time from randomization to radiographic disease progression or death. Radiographic disease progression was defined by identification of 2 or more new bone lesions on a bone scan with confirmation (Prostate Cancer Working Group 2 criteria) and/or progression in soft tissue disease.

A statistically significant improvement in OS and rPFS was demonstrated in patients randomized to receive ERLEADA compared with patients randomized to receive placebo. The results for OS are based upon a prespecified interim efficacy analysis. An updated OS analysis was conducted at the time of final study analysis when 405 deaths were observed. The median follow-up time was 44 months. Thirty-nine percent of patients in the placebo arm crossed over to receive ERLEADA. Efficacy results of TITAN are summarized in Table 5 and Figures 7 and 8.

Consistent improvement in rPFS was observed across the following patient subgroups: disease volume (high vs low), prior docetaxel use (yes or no), and Gleason score at diagnosis (≤7 vs. >7).

Consistent improvement in OS was observed across the following patient subgroups: disease volume (high vs low) and Gleason score at diagnosis (≤7 vs. >7).

Treatment with ERLEADA resulted in a statistically significant delay in the initiation of cytotoxic chemotherapy (HR = 0.39, 95% CI = 0.27, 0.56; $p < 0.0001$).

SPARTAN (NCT01946204): Non-metastatic, Castration-resistant Prostate Cancer (nmCRPC)

SPARTAN was a multicenter, double-blind, randomized (2:1), placebo-controlled clinical trial in which 1207 patients with nmCRPC were randomized (2:1) to receive either ERLEADA orally at a dose of 240 mg once daily (N=806) or placebo once daily (N=401). All patients in the SPARTAN trial received a concomitant GnRH analog or had a bilateral orchiectomy. Patients were stratified by Prostate Specific Antigen (PSA) Doubling Time (PSADT), the use of bone-sparing agents, and locoregional disease. Patients were required to have a PSADT ≤ 10 months and confirmation of non-metastatic disease by blinded independent central review (BICR). PSA results were blinded and were not used for treatment discontinuation. Patients randomized to either arm discontinued treatment for radiographic disease progression confirmed by BICR, locoregional-only progression, initiation of new treatment, unacceptable toxicity, or withdrawal.

The following patient demographics and baseline disease characteristics were balanced between the treatment arms. The median age was 74 years (range 48-97) and 26% of patients were 80 years of age or older. The racial distribution was 66% Caucasian, 12% Asian, and 6% Black. Seventy-seven percent (77%) of patients in both treatment arms had prior surgery or radiotherapy of the prostate. A majority of patients had a Gleason score of 7 or higher (78%). Fifteen percent (15%) of patients had <2 cm pelvic lymph nodes at study entry. Seventy-three percent (73%) of patients received prior treatment with an anti-androgen; 69% of patients received bicalutamide and 10% of patients received flutamide. All patients had an Eastern Cooperative Oncology Group Performance Status (ECOG PS) score of 0 or 1 at study entry.

The major efficacy outcome measure of the study was metastasis-free survival (MFS), defined as the time from randomization to the time of first evidence of BICR-confirmed distant metastasis, defined as new bone or soft tissue lesions or enlarged lymph nodes above the iliac bifurcation, or death due to any cause, whichever occurred first. Additional efficacy endpoints were time to metastasis (TTM), progression-free survival (PFS) which also includes locoregional progression, time to symptomatic progression, overall survival (OS), and time to initiation of cytotoxic chemotherapy.

A statistically significant improvement in MFS and OS was demonstrated in patients randomized to receive ERLEADA compared with patients randomized to receive placebo. The major efficacy outcome (MFS) was supported by improvements in TTM and PFS. The final analysis of OS and time to initiation of cytotoxic chemotherapy was conducted 32 months after the analysis of MFS, TTM and PFS. The efficacy results from SPARTAN are summarized in Table 6 and Figures 9 and 10.

Consistent results for MFS were observed across patient subgroups including PSADT ($\leq 6$ months or $> 6$ months), use of a prior bone-sparing agent (yes or no), and locoregional disease (N0 or N1).

Treatment with ERLEADA resulted in a statistically significant delay in the initiation of cytotoxic chemotherapy [HR = 0.63 (95% CI:0.49, 0.81), p=0.0002].

16 HOW SUPPLIED/STORAGE AND HANDLING

ERLEADA® (apalutamide) tablets are available in the strengths and packages listed below:

- ERLEADA® 240 mg Tablets

Film coated, bluish grey to grey, oval-shaped tablets debossed with "E240" on one side.

NDC Number 59676-604-30 - 30 tablets available in bottles with a silica gel desiccant and has a child-resistant closure

- ERLEADA® 60 mg Tablets

Film coated, slightly yellowish to greyish green, oblong-shaped tablets debossed with "AR 60" on one side.

NDC Number 59676-600-12 - 120 tablets available in bottles with a silica gel desiccant and has a child-resistant closure Storage and Handling
Store at 20 °C to 25 °C (68 °F to 77 °F); excursions permitted to 15 °C to 30 °C (59 °F to 86 °F) *[see USP Controlled Room Temperature]*.

Store in original package to protect from light and moisture. Do not discard desiccant.

17 PATIENT COUNSELING INFORMATION

Advise the patient to read the FDA-approved patient labeling (Patient Information and Instructions for Use).

Cerebrovascular and Ischemic Cardiovascular Events

- Inform patients that ERLEADA has been associated with cerebrovascular and ischemic cardiovascular events. Advise patients to seek immediate medical attention if any symptoms suggestive of a cardiovascular or a cerebrovascular event occur *[see Warnings and Precautions (5.1)]*.

Falls and Fractures

- Inform patients that ERLEADA is associated with an increased incidence of falls and fractures *[see Warnings and Precautions (5.2, 5.3)]*.

Seizures

- Inform patients that ERLEADA has been associated with an increased risk of seizure. Discuss conditions that may predispose to seizures and medications that may lower the seizure threshold. Advise patients of the risk of engaging in any activity where sudden loss of consciousness could cause serious harm to themselves or others. Inform patients to contact their healthcare provider right away if they experience a seizure *[see Warnings and Precautions (5.4)]*.

Severe Cutaneous Adverse Reactions (SCARs)

- Inform patients that ERLEADA has been associated with SCARs (including SJS/TEN and DRESS), which can be life-threatening or fatal. Advise patients to stop taking ERLEADA and contact their healthcare provider or seek medical attention right away if they experience signs or symptoms of SCARs *[see Warnings and Precautions (5.5)]*.

Rash

- Inform patients that ERLEADA is associated with rashes and to inform their healthcare provider if they develop a rash *[see Adverse Reactions (6.1, 6.2)]*.

Dosage and Administration

- Inform patients receiving concomitant gonadotropin-releasing hormone (GnRH) analog therapy that they need to maintain this treatment during the course of treatment with ERLEADA.

- Instruct patients to take their dose at the same time each day (once daily). ERLEADA can be taken with or without food. Each tablet should be swallowed whole. Do not crush or split tablets *[see Dosage and Administration (2.1)]*.
- Instruct patients who cannot swallow tablets whole to follow the instructions for the prescribed strength of ERLEADA tablets for alternate methods of administration *[see Dosage and Administration (2.3)]*.
- Instruct patients on administration of the ERLEADA 240 mg tablet through a feeding tube *[see Dosage and Administration (2.3)]*.
- Inform patients that in the event of a missed daily dose of ERLEADA, they should take their normal dose as soon as possible on the same day with a return to the normal schedule on the following day. The patient should not take extra tablets to make up the missed dose *[see Dosage and Administration (2.1)]*.

Embryo-Fetal Toxicity

- Inform patients that ERLEADA can be harmful to a developing fetus. Advise male patients with female partners of reproductive potential to use effective contraception during treatment and for 3 months after the last dose of ERLEADA. Advise male patients to use a condom if having sex with a pregnant woman *[see Warnings and Precautions (5.6)]*.

Infertility

- Advise male patients that ERLEADA may impair fertility and not to donate sperm during therapy and for 3 months following the last dose of ERLEADA *[see Use in Specific Populations (8.3)]*.

Manufactured for:
Janssen Products, LP
Horsham, PA 19044, USA

For patent information: www.janssenpatents.com

© 2019, 2023 Janssen Pharmaceutical Companies

PATIENT INFORMATION

ERLEADA® (er lee'dah) (apalutamide)

tablets

What is ERLEADA?

ERLEADA is a prescription medicine used for the treatment of prostate cancer:
- that has spread to other parts of the body and still responds to a medical or surgical treatment that lowers testosterone, OR
- that has not spread to other parts of the body and no longer responds to a medical or surgical treatment that lowers testosterone.

It is not known if ERLEADA is safe and effective in females. It is not known if ERLEADA is safe and effective in children.

Before taking ERLEADA, tell your healthcare provider about all your medical conditions, including if you:
- have a history of heart disease
- have high blood pressure
- have diabetes
- have abnormal amounts of fat or cholesterol in your blood (dyslipidemia)
- have a history of seizures, brain injury, stroke, or brain tumors
- are pregnant or plan to become pregnant. ERLEADA can cause harm to your unborn baby and loss of pregnancy (miscarriage).
- have a partner who is pregnant or may become pregnant.
  - Males who have female partners who are able to become pregnant should use effective birth control (contraception) during treatment and for 3 months after the last dose of ERLEADA.
  - Males should use a condom during sex with a pregnant female.

Talk with your healthcare provider if you have questions about birth control.

- are breastfeeding or plan to breastfeed. It is not known if ERLEADA passes into breast milk.

Tell your healthcare provider about all the medicines you take, including prescription and over- the-counter medicines, vitamins, and herbal supplements. ERLEADA can interact with many other medicines.

You should not start or stop any medicine before you talk with the healthcare provider that prescribed ERLEADA.

Know the medicines you take. Keep a list of them with you to show to your healthcare provider and pharmacist when you get a new medicine.

How should I take ERLEADA?

- Take ERLEADA exactly as your healthcare provider tells you.
- Do not stop taking your prescribed dose of ERLEADA without talking with your healthcare provider first.
- Take your prescribed dose of ERLEADA 1 time a day, at the same time each day.
- Take ERLEADA with or without food.
- Swallow ERLEADA tablets whole. Do not crush or split the tablets. If you cannot swallow ERLEADA tablets whole, see the "Instructions for Use" for detailed instructions on how to prepare and take a dose of ERLEADA by mouth. ERLEADA comes in 2 different strengths (60 mg and 240 mg). Follow the instructions for your prescribed strength of ERLEADA.
- If you have a feeding tube, the ERLEADA 240 mg tablet can be given through a feeding tube. See the "Instructions for Use" for detailed instructions on how to prepare and give a dose of ERLEADA through a feeding tube (8 French or larger).
- If you miss a dose of ERLEADA, take your normal dose as soon as possible on the same day. Return to your normal schedule on the following day. You should not take extra tablets to make up the missed dose.

- You should start or continue a gonadotropin-releasing hormone (GnRH) analog therapy during your treatment with ERLEADA unless you have had a surgery to lower the amount of testosterone in your body (surgical castration).
- If you take too much ERLEADA, call your healthcare provider or go to the nearest hospital emergency room.

What are the possible side effects of ERLEADA?

ERLEADA may cause serious side effects including:

- Heart disease, stroke, or mini-stroke. Bleeding in the brain or blockage of the arteries in the heart or in part of the brain have happened in some people during treatment with ERLEADA and can lead to death. Your healthcare provider will monitor you for signs and symptoms of heart or brain problems during your treatment with ERLEADA. Call your healthcare provider or get medical help right away if you get:
    - chest pain or discomfort at rest or with activity
    - shortness of breath
    - numbness or weakness of the face, arm, or leg, especially on one side of the body
    - trouble talking or understanding
    - trouble seeing in one or both eyes
    - dizziness, loss of balance or coordination, or trouble walking
- Fractures and falls. ERLEADA treatment can cause bones and muscles to weaken and may increase your risk for falls and fractures. Falls and fractures have happened in people during treatment with ERLEADA. Your healthcare provider will monitor your risks for falls and fractures during treatment with ERLEADA.
- Seizure. Treatment with ERLEADA may increase your risk of having a seizure. You should avoid activities where a sudden loss of consciousness could cause serious harm to yourself or others. Tell your healthcare provider right away if you have a loss of consciousness or seizure. Your healthcare provider will stop ERLEADA if you have a seizure during treatment.
- Severe skin reactions. Treatment with ERLEADA may cause severe skin reactions that can be life-threatening or may lead to death. Stop taking ERLEADA and get medical help right away if you develop any of these signs or symptoms of a severe skin reaction:

- severe rash or rash that continues to get worse
- fever or flu-like symptoms
- swollen lymph nodes
- blisters or sores in the mouth, throat, nose, eyes, or genital area
- blistering or peeling of the skin The most common side effects of ERLEADA include:

- feeling very tired
- joint pain
- rash. Tell your healthcare provider if you get a rash.
- decreased appetite
- fall
- weight loss
- high blood pressure
- hot flash
- diarrhea
- fracture Your healthcare provider may reduce your dose, temporarily stop, or permanently stop treatment with ERLEADA if you have certain side effects.

ERLEADA may cause fertility problems in males, which may affect the ability to father children. Talk to your healthcare provider if you have concerns about fertility. Do not donate sperm during treatment with ERLEADA and for 3 months after the last dose of ERLEADA.

Tell your healthcare provider if you have any side effect that bothers you or that does not go away.

These are not all the possible side effects of ERLEADA.

Call your doctor for medical advice about side effects. You may report side effects to FDA at 1- 800-FDA-1088.

How should I store ERLEADA?

- Store ERLEADA at room temperature between 68 °F to 77 °F (20 °C to 25 °C).
- ERLEADA comes in a child-resistant bottle.
- Store ERLEADA in the original package to protect from light and moisture.
- The bottle of ERLEADA contains a desiccant packet to help keep your medicine dry (protect it from moisture). Do not throw away (discard) the desiccant.

Keep ERLEADA and all medicines out of the reach of children.

General information about the safe and effective use of ERLEADA.

Medicines are sometimes prescribed for purposes other than those listed in a Patient Information leaflet. Do not use ERLEADA for a condition for which it was not prescribed. Do not give ERLEADA to other people, even if they have the same symptoms that you have. It may harm them. If you would like more information, talk with your healthcare provider. You can ask your healthcare provider or pharmacist for information about ERLEADA that is written for health professionals.

What are the ingredients in ERLEADA?

Active ingredient: apalutamide

Inactive ingredients:

240 mg film-coated tablets: colloidal anhydrous silica, croscarmellose sodium, hydroxypropyl methylcellulose-acetate succinate, silicified microcrystalline cellulose, and magnesium stearate.

The coating contains glyceryl monocaprylocaprate, iron oxide black, polyvinyl alcohol, talc, titanium dioxide, and vinyl alcohol grafted copolymer.

60 mg film-coated tablets: colloidal anhydrous silica, croscarmellose sodium, hydroxypropyl methylcellulose-acetate succinate, magnesium stearate, microcrystalline cellulose, and silicified microcrystalline cellulose. The coating contains iron oxide black, iron oxide yellow, polyethylene glycol, polyvinyl alcohol, talc, and titanium dioxide.

Manufactured for: Janssen Products, LP, Horsham, PA 19044, USA

For patent information: www.janssenpatents.com

© 2019, 2023 Janssen Pharmaceutical Companies

For more information, call Janssen Products, LP at 1-800-526-7736 (1-800-JANSSEN) or go to www.erleada.com.
This Patient Information has been approved by the U.S. Food and Drug Administration. Re

INSTRUCTIONS FOR USE

ERLEADA® (er lee'dah)

(apalutamide)

tablets

This Instructions for Use contains information on how to prepare and give a dose of ERLEADA tablets if you cannot swallow ERLEADA tablets whole or if you have a feeding tube. Read this Instructions for Use before you prepare and take or give the first dose of ERLEADA, and each time you get a refill. Ask your healthcare provider or pharmacist if you have any questions.

Important information you need to know before preparing a dose of ERLEADA:

- ERLEADA comes in 2 different strengths, 60 mg tablets and 240 mg tablets. Please find the instructions below that refer to your prescribed ERLEADA strength for how to prepare and take ERLEADA tablets if you cannot swallow tablets whole.
- ERLEADA 240 mg tablet can be prepared and given through a feeding tube 8 French or larger.

Preparing and taking ERLEADA if you cannot swallow tablets whole:

Preparing and taking ERLEADA 60 mg tablets by mixing with applesauce:

Step 1. Place your entire prescribed dose of ERLEADA tablets in a container that contains 4 ounces (120 mL) of applesauce and stir. Do not crush or split the tablets.

Step 2. Wait 15 minutes and stir the mixture again.

Step 3. Wait another 15 minutes and stir the mixture until the tablets are well mixed with no chunks remaining.

Step 4. Swallow the mixture right away using a spoon.

Step 5. Rinse the container with 2 ounces (60 mL) of water and drink the water mixture right away.

Step 6. Repeat the rinse with 2 ounces (60 mL) of water one more time to make sure that you take your full dose of ERLEADA.

Swallow all the applesauce and medicine mixture within 1 hour of preparation. Do not store ERLEADA that is mixed with applesauce.

Preparing and taking ERLEADA 240 mg tablet by placing the tablet in non-carbonated water then mixing with orange juice, applesauce, or more non-carbonated water:

Step 1. Place the whole ERLEADA tablet in a cup. Do not crush or split the tablet.

Step 2. Add about 2 teaspoons (10 mL) of non-carbonated water to make sure that the tablet is completely covered in water.

Step 3. Wait 2 minutes until the tablet is broken up and spread out, then stir the mixture.

Step 4. Add 2 tablespoons (30 mL) of orange juice, applesauce, or non-carbonated water to the cup and stir the mixture.

Step 5. Swallow the mixture right away.

Step 6. Rinse the cup with enough non-carbonated water to make sure that you take your full dose of ERLEADA and drink it right away.

Do not store ERLEADA that is mixed with non-carbonated water, orange juice, or applesauce for later use.

Preparing and giving ERLEADA 240 mg tablet through a feeding tube 8 French or larger:

Step 1. Remove the plunger out of the syringe (use at least a 20 mL syringe).

Step 2. Add one 240 mg tablet into the syringe body (barrel) and place the plunger back in the syringe. Do not crush or split the tablet.

Step 3. Withdraw 10 mL of non-carbonated water into the syringe.

Step 4. Wait 10 minutes and then shake the syringe very well (vigorously) to break the tablet apart completely.

Step 5. Attach the syringe to the feeding tube and give the mixture right away.

Step 6. Withdraw non-carbonated water into the same syringe and flush through the feeding tube. Repeat Step 6 until no pieces of tablet are left in the syringe or feeding tube.

How should I store ERLEADA?

- Store ERLEADA at room temperature between 68 °F to 77 °F (20 °C to 25 °C).
- ERLEADA comes in a child-resistant bottle.
- Store ERLEADA in the original package to protect from light and moisture.
- The bottle of ERLEADA contains a desiccant packet to help keep your medicine dry (protect it from moisture). Do not throw away (discard) the desiccant.

Keep ERLEADA and all medicines out of the reach of children.

Manufactured for: Janssen Products, LP, Horsham, PA 19044, USA
For patent information: www.janssenpatents.com
© 2019, 2023 Janssen Pharmaceutical Companies For more information, call Janssen Products, LP at 1-800-526-7736 (1-800-JANSSEN) or go to www.erleada.com.

This Instructions for Use has been approved by the U.S. Food and Drug Administration.

Issued: 02/2023

One skilled in the art will recognize that, to be valid and meaningful, any comparison of real-world evidence and clinical trial results requires that the data sets (real-world evidence and clinical trial results) match all parameters defined in the clinical trial including, patient characteristics (e.g. patient baseline characteristics, PC staging, and comorbidities) and dosing parameters (e.g. duration, dosage amount, dosing regimen, adherence, and concomitant active moieties).

The invention claimed is:

1. A tablet comprising an intragranular phase and an extragranular phase, wherein the intragranular phase comprises:

a solid dispersion comprising

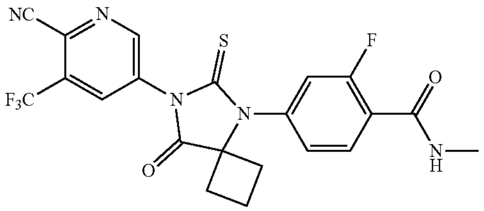 [SMILES: CNC(=O)c1ccc(N2C(=S)N(c3cnc(C#N)c(C(F)(F)F)c3)C(=O)C23CCC3)cc1F]

(apalutamide) and hydroxypropyl methylcellulose acetate succinate (HPMCAS), and a pharmaceutically acceptable carrier comprising a glidant and a disintegrant, wherein the solid dispersion is present at equal or greater than 80 w/w % relative to the total weight of the tablet.

2. The tablet of claim 1, wherein the solid dispersion is present at about 82.4 w/w % relative to the total weight of the tablet.

3. The tablet of claim 1, wherein the tablet comprises about 960 mg of the solid dispersion.

4. The tablet of claim 1, wherein the tablet comprises about 240 mg of apalutamide.

5. The tablet of claim 1, wherein the weight-by-weight ratio of apalutamide to HPMCAS in the solid dispersion is in the range of 1:1 to 1:5.

6. The tablet of claim 1, wherein the weight-by-weight ratio of apalutamide to HPMCAS in the solid dispersion is 1:3.

7. The tablet of claim 1, wherein apalutamide is present in amorphous form in the solid dispersion.

8. The tablet of claim 1, wherein the solid dispersion is a solid solution.

9. The tablet of claim 1, wherein the HPMCAS is HPMCAS granular grade.

10. The tablet of claim 1, wherein the solid dispersion is obtainable by spray drying.

11. The tablet of claim 1, wherein the solid dispersion is in particulate form.

12. The tablet of claim 1, wherein the pharmaceutically acceptable carrier further comprises one or more of a filler and a lubricant.

13. The tablet of claim 12, wherein:

the glidant is colloidal anhydrous silica, the disintegrant is croscarmellose sodium, the filler is silicified microcrystalline cellulose, and the lubricant is magnesium stearate.

14. The tablet of claim 13, wherein the tablet does not comprise a dry binder.

15. The tablet of claim 1, wherein the intragranular phase comprises about 0.4 w/w % glidant and about 3.0 w/w % disintegrant, wherein the w/w % is relative to the total weight of the tablet.

16. The tablet of claim 1, wherein the extragranular phase comprises a filler, a glidant, a disintegrant, and a lubricant.

17. The tablet of claim 16, wherein the extragranular phase comprises about 10.3 w/w % filler, about 0.4 w/w % glidant, about 3.0 w/w % disintegrant, and about 0.5 w/w % lubricant, wherein the w/w % is relative to the total weight of the tablet.

18. A tablet comprising an intragranular phase and an extragranular phase, wherein the intragranular phase comprises:

a solid dispersion comprising

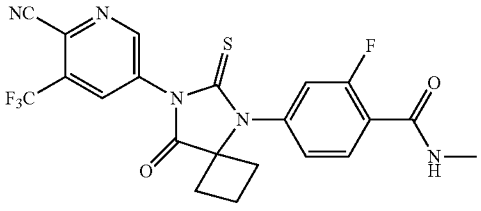 [SMILES: CNC(=O)c1ccc(N2C(=S)N(c3cnc(C#N)c(C(F)(F)F)c3)C(=O)C23CCC3)cc1F]

(apalutamide) and hydroxypropyl methylcellulose acetate succinate (HPMCAS), colloidal anhydrous silica, and croscarmellose sodium, and wherein the extragranular phase comprises:

silicified microcrystalline cellulose colloidal anhydrous silica, croscarmellose sodium, and magnesium stearate, and wherein the solid dispersion is present at equal or greater than 80 w/w % relative to the total weight of the tablet.

19. The tablet of claim 18, wherein the tablet has the following composition:

| Component | w/w (%) |
|---|---|
| Intragranular phase | |
| Spray Dried Powder comprising apalutamide and HPMCAS at a 1:3 ratio by weight | 82.40 |
| Colloidal Anhydrous Silica | 0.40 |
| Croscarmellose Sodium | 3.00 |
| Extragranular phase | |
| Silicified Microcrystalline Cellulose | 10.28 |
| Colloidal Anhydrous Silica | 0.40 |
| Croscarmellose Sodium | 3.00 |
| Magnesium Stearate | 0.50 |

wherein the tablet optionally further comprises a coating.

20. The tablet of claim 18, wherein apalutamide is present in amorphous form in the solid dispersion.

21. The tablet of claim 20, wherein the solid dispersion is a solid solution.

22. The tablet of claim 18, wherein the tablet comprises a coating.

23. The tablet of claim 22, wherein the coating is a polyvinyl alcohol-polyethylene glycol (PVA-PEG) copolymer.

24. A method of treating prostate cancer comprising administering to a subject in need thereof a therapeutically effective amount of a tablet of claim 1.

* * * * *